(12) United States Patent
Wang et al.

(10) Patent No.: US 6,900,323 B2
(45) Date of Patent: May 31, 2005

(54) ANTIVIRAL AZAINDOLE DERIVATIVES

(75) Inventors: Tao Wang, Middletown, CT (US);
Owen B. Wallace, Zionsville, IN (US);
Zhongxing Zhang, Madison, CT (US);
Nicholas A. Meanwell, East Hampton, CT (US); John A. Bender, Rocky Hill, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/621,139

(22) Filed: Jul. 16, 2003

(65) Prior Publication Data
US 2004/0023982 A1 Feb. 5, 2004

Related U.S. Application Data

(60) Division of application No. 10/268,350, filed on Oct. 10, 2002, now Pat. No. 6,632,819, which is a division of application No. 09/912,710, filed on Jul. 25, 2001, now Pat. No. 6,476,034, which is a continuation-in-part of application No. 09/765,189, filed on Jan. 18, 2001, now abandoned.
(60) Provisional application No. 60/184,004, filed on Feb. 22, 2000.

(51) Int. Cl.$^7$ ............................................. C07D 471/04
(52) U.S. Cl. ...................................................... 546/113
(58) Field of Search ......................................... 546/113

(56) References Cited

U.S. PATENT DOCUMENTS

| | | | |
|---|---|---|---|
| 5,023,265 A | | 6/1991 | Scherlock et al. |
| 5,124,327 A | | 6/1992 | Greenlee et al. |
| 5,413,999 A | | 5/1995 | Vacca et al. |
| 5,424,329 A | | 6/1995 | Boschelli et al. |
| 5,681,959 A | * | 10/1997 | Bishop et al. .............. 546/113 |
| 5,811,432 A | | 9/1998 | Marfat et al. |
| 2003/0069266 A1 | * | 4/2003 | Wang et al. ................. 514/300 |
| 2003/0236277 A1 | * | 12/2003 | Kadow et al. .............. 514/300 |
| 2004/0006090 A1 | * | 1/2004 | Kadow et al. ........... 514/253.04 |
| 2004/0063744 A1 | * | 4/2004 | Wang et al. ................. 514/300 |
| 2004/0063746 A1 | * | 4/2004 | Regueiro-Ren et al. ..... 514/300 |
| 2004/0110785 A1 | * | 6/2004 | Wang et al. ................. 514/300 |

FOREIGN PATENT DOCUMENTS

| | | |
|---|---|---|
| EP | 0379314 A1 | 7/1990 |
| EP | 0484071 A2 | 5/1992 |
| EP | 0530907 A1 | 3/1993 |
| WO | WO 93/01181 | 1/1993 |
| WO | WO 95/04742 | 2/1995 |
| WO | WO 96/11929 | 4/1996 |
| WO | WO 00/76521 A1 | 12/2000 |

OTHER PUBLICATIONS

H. Hotoda, "Small–Molecule Inhibitors of HIV–1 Entry Via Chemokine Receptors," Drugs of the Future, 24(12), pp. 1355–1362, 1999.

J. G. Sodroski, "HIV–1 Entry Inhibitors in the Side Pocket," Cell, 99, pp. 243–246, 1999.

W. S. Blair, et al, "HIV–1 Entry—An Expanding Portal for Drug Discovery," Drug Discovery Today, 5(5), pp. 183–194, 2000.

B. A. Larder, et al, "Multiple Mutations in HIV–1 Reverse Transcriptase Confer High–Level Resistance to Zidovudine (AZT)," Science, 246, pp. 1155–1158, 1989.

R. M. Gulick, "Curent Antiretroviral Therapy: An Overview," Quality of Life Research, 6, pp. 471–474, 1997.

D. R. Kuritzkes, "HIV Resistance to Current Therapies," Antiviral Therapy, 2 (Supplement 3), pp. 61–67, 1997.

S. Morris–Jones, et al, "Antiretroviral Therapies in HIV–1 Infection," Expert Opinion on Investigational Drugs, 6(8), pp. 1049–1061, 1997.

R. F. Schinazi, et al, "Mutations in Retroviral Genes Associated with Drug resistance," International Antiviral News, 5(8), pp. 129–142, 1997.

J. P. Vacca, et al, "Clinically Effective HIV–1 Protease Inhibitors," Drug Discovery Today, 2(7), pp. 261–272, 1997.

D. Flexner, "HIV–Protease Inhibitors," Drug Therapy, 338(18), pp. 1281–1292, 1998.

B. Berkhout, "HIV–1 Evolution Under Pressure of Protease Inhibitors: Climbing the Stairs of Viral Fitness," J. Biomed. Sci., 6, pp. 298–305, 1999.

S. Ren, et al, "Development of HIV Protease Inhibitors: A Survey," Progress in Drug Research, 51, pp. 1–31, 1998.

O. S. Pedersen, et al, "Non–Nucleoside Reverse Transcriptase Inhibitors: the NNRTI Boom," Antiviral Chemistry & Chemotherapy, 10, pp. 285–314, 1999.

E. De Clercq, "The Role of Non–Nucleoside Reverse Transcriptase Inhibitors (NNRTIs) in the Therapy of HIV–1 Infection," Antiviral Research, 38, pp. 153–179, 1998.

E. De Clercq, "Perspectives of Non–Nucleoside Reverse Transcriptase Inhibitors (NNRTIs) in the Therapy of HIV–1 Infection," IL Farmaco, 54, pp. 26–45, 1999.

M. Font, et al, "Indoles and Pyridazino[4,5–b]Indoles as Nonnucleoside Analog Inhibitors of HIV–1 Reverse Transcriptase," Eur. J. Med. Chem., 30, pp. 963–971, 1995.

D. L. Romero, et al, J. Med. Chem., 36, pp. 1505–1508, 1993.

S. D. Young, et al, "2–Heterocyclic Indole–3–Sulfones as Inhibitors of HIV–1 Reverse Transcriptase," Bioorganic & Medicinal Chemistry Letters, 5(5), pp. 491–496, 1995.

M. J. Genin, et al, "Synthesis and Bioactivity of Novel Bis(Heteroaryl)Piperazine (BHAP) Reverse Transcriptase Inhibitors: Structure–Activity Relationships and Increased Metabolic Stability of Novel Substituted Pyridine Analogs," J. Med. Chem., 39, pp. 5267–5275, 1996.

(Continued)

Primary Examiner—Emily Bernhardt
(74) Attorney, Agent, or Firm—Samuel J. DuBoff

(57) ABSTRACT

The invention comprises novel azaindole intermediate compounds useful in the preparation of compounds of the class of azaindole piperazine diamide derivatives, composition thereof and their use as anti-viral agents, and particularly for treating HIV infection.

2 Claims, No Drawings

OTHER PUBLICATIONS

R. Silvestri, et al, Antiviral Chemistry & Chemotherapy, 9, pp. 139–148, 1998.

A. Fredenhagen, et al, "Semicochliodinol A and B: Inhibitors of HIV–1 Protease and EGF–R Protein Tyrosine Kinase Related to Asterriquinones Produced by the Fungus *Chrysosporium merdarium*," Journal of Antibiotics, 50(5), pp. 395–401, 1997.

M. Kato, et al, "New 5–HT$_3$ (Serotonin–3) Receptor Antagonists. IV. Synthesis and Structure–Activity Relationships of Azabicycloalkaneacetamide Derivatives," Chem. Pharm. Bull, 43(8), pp. 1351–1357, 1995.

V. Levacher, et al, "Broadening in the Scope of NADH Models by Using Chiral and Non Chiral Pyrrolo [2,3–b] Pyridine Derivatives," Tetrahedron, 47(3), pp. 429–440, 1991.

I. Mahadevan, et al, "Synthesis of Pyrrolopyridines (Azaindoles)," J. Heterocyclic Chem., 29, pp. 359–367, 1992.

D. Hands, et al, "Convenient Method for the Preparation of 5–, 6– and 7–Azaindoles and Their Derivatives," Synthesis, pp. 877–882, 1996.

D. Dobson, et al, "The Synthesis of 7–Alkoxyindoles," Synthetic Communications, 21(5), pp. 611–617, 1991.

T. Sakamoto, et al, "Condensed Heteroaromatic Ring Systems, XII. Synthesis of Indole Derivatives from Ethyl 2–Bromocarbanilates," Chem. Pharm. Bull., 35(5), pp. 1823–1828, 1987.

L. P. Shadrina, et al, "Reactions of Organomagnesium Derivatives of 7–Aza– and Benzoindoles with Diethyl Oxalate and the Reactivity of Ethoxalylindoles," Khim. Geterotsikl. Soedin., 9, pp. 1206–1209, 1987 (Russian).

T. V. Sycheva, et al, "Some Reactions of 5–Cyano–6–Chloro–7–Azaindoles and Lactam–Lactim Tautomerism in 5–Cyano–6–Hydroxy–7–Azaindolines," Khim. Geterotsikl. Soedin., 1, pp. 100–106, 1987 (Russian).

H. Li, et al, "3–(Diethoxyphosphoryloxy)–1,2,3–Benzotriazin–4(3H)–one (DEPBT): A New Coupling Reagent with Remarkable Resistance to Racemization," Organic Letters, 1(1), PP. 91–93, 1999.

M. Desai, et al, "A Convenient Preparation of 1–Aroylpiperazines," Organic Preparations and Procedures Int., 8(2), pp. 85–86, 1976.

M. Adamczyk, et al, "Synthesis of Procainamide Metabolites N–Acetyl Desethylprocainamide and Desethylprocainamide," Organic Preparations and Procedures Int., 28(4), pp. 470–474, 1996.

K. Rossen, et al, "Asymmetric Hydrogenation of Tetrahydropyrazines: Synthesis of (S)–Piperazine–2–Tert–Butylcarboxamide, an Intermediate in the Preparation of the HIV Protease Inhibitor Indinavir," Tetrahedron Letters, 36(36), pp. 6419–6422, 1995.

T. Wang, et al, "Benzoylatin of Dianions: Preparation of Monobenzoylated Derivatives of Symmetrical Secondary Diamines," J. Org. Chem., 64, pp. 7661–7662, 1999.

T. Wang, et al, "Regioselective Monobenzoylation of Unsymmetrical Piperazines," J. Org. Chem., 65, pp. 4740–4742, 2000.

N. Harada, et al, "Synthesis and Antitumor Activity of Quaternary Salts of 2–(2'–Oxoalkoxy)–9–Hydroxyellipticines," Chem. Pharm. Bull., 45(1), pp. 134–137, 1997.

I. Antonini, et al, "Synthesis of 4–Amino–1–β–D–Ribofuranosyl–1H–Pyrrolo[2,3–b]Pyridine (1–Deazatubercidin) as a Potential Antitumor Agent," J. Med. Chem., 25, pp. 1258–1261, 1982.

S. W. Schneller, et al, J. Org. Chem., 45, pp. 4045–4048, 1980.

M. Wozniak, et al, "Amination of 4–Nitroquinoline with Liquid Methylamine/Potassium Permanganate," Chemistry of Heterocyclic Compounds, 34(7), pp. 837–840, 1998.

S. Shiotani, et al, J. Heterocyclic. Chem., 34, pp. 901–907, 1997.

S. Minakata, et al, "Regioselective Functionalization of 1H–Pyrrolo[2,3–b]Pyridine Via Its N–Oxide," Synthesis, pp. 661–663, 1992.

L. H. Klemm, et al, "Chemistry of Theinopyridines, XXIV. Two Transformations of Thieno[2,3–b]Pyridine 7–Oxide (1)," J. Heterocyclic Chem., 13, pp. 1197–1200, 1976.

S. Shiotani, et al, "Furopyridines. XXXIII [1]. Synthesis and Reactions of Chloropyridine Derivatives of Furo[2,3–b]–,–[2,3–c]–and–[3,2–c]Pyridine," J. Heterocyclic Chem., 34, pp. 925–929, 1997.

M. Hayashida, et al, "Deoxygenative 2–Alkoxylation of Quinoline 1–Oxide," Heterocycles, 31(7), pp. 1325–1331, 1990.

Y. Miura, et al, "Synthesis of 2,3–Fused Quinolines From 3–Substituted Quinoline 1–Oxides, Part 1.," Heterocycles, 34(5), pp. 1055–1063, 1992.

M. A. Solekhova, et al, "A New Reaction of Reductive Amination of Quinoline N–Oxide with 2–Aminopyridine," Zh. Org. Khim., 32, p. 956, 1996 (Russian).

J. B. Regnouf de Vains, et al, "New Symmetric and Unsymmetric Polyfunctionalized 2,2'Bipyridines," J. Heterocyclic Chem., 31, pp. 1069–1077, 1994.

Y. Miura, et al, "Synthesis of 2,3–Fused Quinolines from 3–Substituted Quinoline 1–Oxides, Part II.," Heterocycles, 36(5), pp. 1005–1016, 1993.

V. E. Profft, et al, "Uber 4–Merkaptoverbindungendes 2–Methylpyridins," J. Prakt. Chem., 283(11), pp. 22–34, 1960 (German).

R. Nesi, et al, "A New One Step Synthetic Approach to the Isoxazolo[4,5–b]Pyridine System," Synthetic Communications, 22(16), pp. 2349–2355, 1992.

A. Walser, et al, "Quinazolines and 1,4–Benzodiazepines. 75. 7–Hydroxyaminobenzodiazepines and Derivatives," J. Med. Chem., 19(12), pp. 1378–1381, 1976.

G. Barker, et al, "Benzopyrones. Part I. 6–Amino– and 6–Hydroxy–2–Substituted Chromones," J. Chem. Soc., pp. 2230–2233, 1970.

N. R. Ayyangar, et al, "An Alternate Synthesis of 3,4–Diaminobenzophenone and of Mebendazole," Org. Prep. Proced. Int., 23(5), pp. 627–631, 1991.

I. Mahadevan, et al, "Ambident Heterocyclic Reactivity: The Alkylation of Pyrrolopyridines (Azaindoles, Diazaindenes)," Tetrahedron, 49(33), pp. 7337–7352, 1993.

T. Sakamoto, et al, "Palladium–Catalyzed Cyanation of Aryl and Heteroaryl Iodides with Copper(I)Cyanide," J. Chem. Soc., Perkin Trans. 1, pp. 2323–2326, 1999.

F. Halley, et al, "Synthesis of 5–Cyanoindazole and 1–Methyl and 1–Aryl–5–Cyanoindazoles," Synthetic Communications, 27(7), pp. 1199–1207, 1997.

S. Yamaguchi, et al, "The Synthesis of Benzofuroquinolines. X. Some Benzofurol[3,2–c]lsoquinoline Deravitives," J. Heterocyclic Chem., 32, pp. 1517–1519, 1995.

D. J. Funhoff, et al, "Cyclo[d.e.d.e.e.d.e.d.e.e.]Decakisbenzene, a New Cycloarene," Angew Chem., Int. Ed. Engl., 25(8), pp. 742–744, 1986.

V. Klimesova, et al, "Potential Antifungal Agents. Synthesis and Activity of 2–Alkylthiopyridine–4–Carbothioamides," Eur. J. Med. Chem., 31, pp. 389–395, 1996.

A. R. Katritzky, et al, "Synthesis and Reactivity of 2,6–Diamino–4–Methyl–3–Pyridinecarbonitrile," J. Heterocyclic Chem., 32, pp. 979–984, 1995.

M. Miletin, et al, "Synthesis of Some Anilides of 2–Alkyl–4–Pyridinecarboxylic Acids and Their Photosynthesis–Inhibiting Activity," Collect. Czech. Chem. Commun., 62, pp. 672–678, 1997.

S. Shiotani, et al, "Furopyridines. XVII[1]. Cyanation, Chlorination and Nitration of Furo[3,2–b]Pyridine N–Oxide," J. Heterocyclic Chem., 33, pp. 1051–1056, 1996.

A. El Hadri, et al, "A Convenient Synthesis of cis–4–(Sulfomethyl)–Piperidine–2–Carboxylic Acid: NMR Assignment," J. Heterocyclic Chem., 30, pp. 631–635, 1993.

F. R. Heirtzler, "Preparation of Non–Symmetrical 2,3–bis–(2,2'–Oligopyridyl)Pyrazines Via 1,2–Disubstituted Ethanones," SYNLETT., 8, pp. 1203–1206, 1999.

T. Norrby, et al, "Regioselective Functionalization of 2,2'–Bipyridine and Transformations into Unsymmetric Ligands for Coordination Chemistry," Acta Chem. Scand., 52, pp. 77–85, 1998.

Sitsun'van, Borisova, E. Ya, et al, Zh Org Khim., 31, pp. 1169–1172, 1995 (Russian).

S. H. Reich, et al, "Structure–Based Design and Synthesis of Substituted 2–Butanols as Nonpeptidic Inhibitors of HIV Protease: Secondary Amide Series," J. Med. Chem., 39, pp. 2781–2794, 1996.

Salfetnikova, Yu. N., et al, Zh. Org. Khim., 34, pp. 888–894, 1998 (Russian).

A. R. Oki, et al, "An Efficient Preparation of 4,4'–Dicarboxy–2,2'–Bipyridine," Synthetic Communications, 25(24), pp. 4093–4097, 1995.

N. Garelli, et al, "Synthesis of New Amphiphilic Perfluoroalkylated Bipyridines," J. Org. Chem., 57, pp. 3046–3051, 1992.

J. Koyama, et al, "Diels–Alder Reaction of 1,2,3–Triazine with Aldehyde Enamine," Heterocycles, 38(7), pp. 1595–1600, 1994.

M. Yasuda, et al, J. Heterocyclic Chem., 24, pp. 1253–1260, 1987.

R. Levine, et al, "The Relative Reactivities of the Isomeric Methyl Pyridinecarboxylates in the Acylation of Certain Ketones. The Synthesis of β–Diketones Containing Pyridine Rings," J. Am. Chem. Soc., 73, pp. 5614–5616, 1951.

M. Z. Hoemann, et al, "Solid–Phase Synthesis of Substituted Quinoline and Isoquinoline Derivatives Using Heterocyclic N–Oxide Chemistry," Tetrahedron Letters, 39, pp. 4749–4752, 1998.

M. H. Norman, et al, "Synthesis and Evaluation of Heterocyclic Carboxamides as Potential Antipsychotic Agents," J. Med. Chem., 39, pp. 4692–4703, 1996.

B. S. Jursic, et al, "A Simple Preparation of Amides from Acids and Amines by Heating of Their Mixture," Synthetic Communications, 23(19), pp. 2761–2770, 1993.

L. Strekowski, et al, "Synthesis and Structure–DNA Binding Relationship Analysis of DNA Triple–Helix Specific Intercalators," J. Med. Chem., 39, pp. 3980–3983, 1996.

G. Shi, et al, "Metalated Fluoropyridines and Fluoroquinolines as Reactive Intermediates: New Ways for Their Regioselective Generation," Tetrahedron, 50(4), pp. 1129–1134, 1994.

G. K. Chen, et al, J. Virol., 68(2), pp. 654–860, 1994.

G. J. Clark et al, "Synthetic Uses of the Sequential Ring Positional Reactivity in Pyridine–3–of and Derivatives," Aust. J. Chem., 34, pp. 927–932, 1981.

H. J. Anderson, et al, "Pyrrole Chemistry, XXII. A "One–Pot" Synthesis of Some 4–Acylpyrrole–2–Carboaldehydes From Pyrrole," Can. J. Chem., 58, pp. 2527–2530, 1980.

H. Suzuki, et al, "A General Synthetic Route for 1–Substituted 4–Oxygenated β–Carbolines (Synthetic Studies on Indoles and Related Compounds 41)," Tetrahedron, 53(5), pp. 1593–1606, 1997.

* cited by examiner

ANTIVIRAL AZAINDOLE DERIVATIVES

CROSS-REFERENCE TO RELATED APPLICATIONS

This is a Divisional application of application Ser. No. 10/268,350 filed Oct. 10, 2002, now U.S. Pat. No. 6,632,819; which is a Divisional application of application Ser. No. 09/912,710 filed Jul. 25, 2001, now U.S. Pat. No. 6,476,034; which is a continuation-in-part application of U.S. Non-Provisional Application Ser. No. 09/765,189 filed Jan. 18, 2001, now bandoned, which claims the benefit of U.S. Provisional Application Serial No. 60/184,004 filed Feb. 22, 2000.

BACKGROUND OF THE INVENTION

1. Field of the Invention

This invention provides compounds having drug and bio-affecting properties, their pharmaceutical compositions and method of use. In particular, the invention is concerned with azaindole piperazine diamide derivatives that possess unique antiviral activity. More particularly, the present invention relates to compounds useful for the treatment of HIV and AIDS.

2. Background Art

HIV-1 (human immunodeficiency virus-1) infection remains a major medical problem, with an estimated 33.6 million people infected worldwide. The number of cases of HIV and AIDS (acquired immunodeficiency syndrome) has risen rapidly. In 1999, 5.6 million new infections were reported, and 2.6 million people died from AIDS. Currently available drugs for the treatment of HIV include six nucleoside reverse transcriptase (RT) inhibitors (zidovudine, didanosine, stavudine, lamivudine, zalcitabine and abacavir), three non-nucleoside reverse transcriptase inhibitors (nevirapine, delavirdine and efavirenz), and five peptidomimetic protease inhibitors (saquinavir, indinavir, ritonavir, nelfinavir and amprenavir). Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present (Larder and Kemp; Gulick; Kuritzkes; Morris-Jones et al; Schinazi et al; Vacca and Condra; Flexner; Berkhout and Ren et al; (Ref. 6–14)). Therefore, novel anti-HIV agents exhibiting distinct resistance patterns, and favorable pharmacokinetic as well as safety profiles are needed to provide more treatment options.

Currently marketed HIV-1 drugs are dominated by either nucleoside reverse transcriptase inhibitors or peptidomimetic protease inhibitors. Non-nucleoside reverse transcriptase inhibitors (NNRTIs) have recently gained an increasingly important role in the therapy of HIV infections (Pedersen & Pedersen, Ref. 15). At least 30 different classes of NNRTI have been described in the literature (De Clercq, Ref. 16) and several NNRTIs have been evaluated in clinical trials. Dipyridodiazepinone (nevirapine), benzoxazinone (efavirenz) and bis(heteroaryl) piperazine derivatives (delavirdine) have been approved for clinical use. However, the major drawback to the development and application of NNRTIs is the propensity for rapid emergence of drug resistant strains, both in tissue cell culture and in treated individuals, particularly those subject to monotherapy. As a consequence, there is considerable interest in the identification of NNRTIs less prone to the development of resistance (Pedersen & Pedersen, Ref. 15).

Several indole derivatives including indole-3-sulfones, piperazino indoles, pyrazino indoles, and 5H-indolo[3,2-b][1,5]benzothiazepine derivatives have been reported as HIV-1 reverse transcriptase inhibitors (Greenlee et al, Ref. 1; Williams et al, Ref. 2; Romero et al, Ref. 3; Font et al, Ref. 17; Romero et al, Ref. 18; Young et al, Ref. 19; Genin et al, Ref. 20; Silvestri et al, Ref. 21). Indole 2-carboxamides have also been described as inhibitors of cell adhesion and HIV infection (Boschelli et al, U.S. Pat. No. 5,424,329, Ref. 4). Finally, 3-substituted indole natural products (Semicochliodinol A and B, didemethylasterriquinone and isocochliodinol) were disclosed as inhibitors of HIV-1 protease (Fredenhagen et al, Ref. 22).

Structurally related aza-indole amide derivatives have been disclosed previously (Kato et al, Ref. 23; Levacher et al, Ref. 24; Mantovanini et al, Ref. 5(a); Cassidy et al, Ref. 5(b); Scherlock et al, Ref. 5(c)). However, these structures differ from those claimed herein in that they are aza-indole mono-amides rather than unsymmetrical aza-indole piperazine diamide derivatives, and there is no mention of the use of these compounds for treating antiviral infections, particularly HIV. Nothing in these references can be construed to disclose or suggest the novel compounds of this invention and their use to inhibit HIV infection.

REFERENCES CITED

Patent Documents
1. Greenlee, W. J.; Srinivasan, P. C. Indole reverse transcriptase inhibitors. U.S. Pat. No. 5,124,327.
2. Williams, T. M.; Ciccarone, T. M.; Saari, W. S.; Wai, J. S.; Greenlee, W. J.; Balani, S. K.; Goldman, M. E.; Theohrides, A. D. Indoles as inhibitors of HIV reverse transcriptase. European Patent 530907.
3. Romero, D. L.; Thomas, R. C.; Preparation of substituted indoles as anti-AIDS pharmaceuticals. PCT WO 93/01181.
4. Boschelli, D. H.; Connor, D. T.; Unangst, P. C. Indole-2-carboxamides as inhibitors of cell adhesion. U.S. Pat. No. 5,424,329.
5. (a) Mantovanini, M.; Melillo, G.; Daffonchio, L. Tropyl 7-azaindol-3-ylcarboxyamides as antitussive agents. PCT WO 95/04742 (Dompe Spa). (b) Cassidy, F.; Hughes, I.; Rahman, S.; Hunter, D. J. Bisheteroaryl-carbonyl and carboxamide derivatives with 5HT 2C/2B antagonists activity. PCT WO 96/11929. (c) Scherlock, M. H.; Tom, W. C. Substituted 1H-pyrrolopyridine-3-carboxamides. U.S. Pat. No. 5,023,265.

Other Publications
6. Larder, B. A.; Kemp, S. D. Multiple mutations in the HIV-1 reverse transcriptase confer high-level resistance to zidovudine (AZT). *Science*, 1989, 246, 1155–1158.
7. Gulick, R. M. Current antiretroviral therapy: An overview. *Quality of Life Research*, 1997, 6, 471–474.
8. Kuritzkes, D. R. HIV resistance to current therapies. *Antiviral Therapy*, 1997, 2 (Supplement 3), 61–67.
9. Morris-Jones, S.; Moyle, G.; Easterbrook, P. J. Antiretroviral therapies in HIV-1 infection. *Expert Opinion on Investigational Drugs*, 1997, 6(8),1049–1061.

10. Schinazi, R. F.; Larder, B. A.; Mellors, J. W. Mutations in retroviral genes associated with drug resistance. *International Antiviral News*, 1997, 5,129-142,.
11. Vacca, J. P.; Condra, J. H. Clinically effective HIV-1 protease inhibitors. *Drug Discovery Today*, 1997, 2, 261–272.
12. Flexner, D. HIV-protease inhibitors. *Drug Therapy*, 1998, 338, 1281–1292.
13. Berkhout, B. HIV-1 evolution under pressure of protease inhibitors: Climbing the stairs of viral fitness. *J. Biomed. Sci.*, 1999, 6, 298–305.
14. Ren, S.; Lien, E. J. Development of HIV protease inhibitors: A survey. *Prog. Drug Res.*, 1998, 51, 1–31.
15. Pedersen, O. S.; Pedersen, E. B. Non-nucleoside reverse transcriptase inhibitors: the NNRTI boom. *Antiviral Chem. Chemother.* 1999, 10, 285–314.
16. (a) De Clercq, E. The role of non-nucleoside reverse transcriptase inhibitors (NNRTIs) in the therapy of HIV-1 infection. *Antiviral Research*, 1998, 38, 153–179. (b) De Clercq, E. Perspectives of non-nucleoside reverse transcriptase inhibitors (NNRTIs) in the therapy of HIV infection. IL. *Farmaco*, 1999, 54, 26–45.
17. Font, M.; Monge, A.; Cuartero, A.; Elorriaga, A.; Martinez-Irujo, J. J.; Alberdi, E.; Santiago, E.; Prieto, I.; Lasarte, J. J.; Sarobe, P. and Borras, F. Indoles and pyrazino[4,5-b]indoles as nonnucleoside analog inhibitors of HIV-1 reverse transcriptase. *Eur. J. Med. Chem.*, 1995, 30, 963–971.
18. Romero, D. L.; Morge, R. A.; Genin, M. J.; Biles, C.; Busso, M,; Resnick, L.; Althaus, I. W.; Reusser, F.; Thomas, R. C and Tarpley, W. G. Bis(heteroaryl) piperazine (BHAP) reverse transcriptase inhibitors: structure-activity relationships of novel substituted indole analogues and the identification of 1-[(5-methanesulfonamido-1H-indol-2-yl)-carbonyl]-4-[3-[1-methylethyl)amino]-pyridinyl]piperazine momomethansulfonate (U-90152S), a second generation clinical candidate. *J. Med. Chem.*, 1993, 36, 1505–1508.
19. Young, S. D.; Amblard, M. C.; Britcher, S. F.; Grey, V. E.; Tran, L. O.; Lumma, W. C.; Huff, J. R.; Schleif, W. A.; Emini, E. E.; O'Brien, J. A.; Pettibone, D. J. 2-Heterocyclic indole-3-sulfones as inhibitors of HIV-reverse transcriptase. *Bioorg. Med. Chem. Lett.*, 1995, 5, 491–496.
20. Genin, M. J.; Poel, T. J.; Yagi, Y.; Biles, C.; Althaus, I.; Keiser, B. J.; Kopta, L. A.; Friis, J. M.; Reusser, F.; Adams, W. J.; Olmsted, R. A.; Voorman, R. L.; Thomas, R. C. and Romero, D. L. Synthesis and bioactivity of novel bis(heteroaryl)piperazine (BHAP) reverse transcriptase inhibitors: structure-activity relationships and increased metabolic stability of novel substituted pyridine analogs. *J. Med. Chem.*, 1996, 39, 5267–5275.
21. Silvestri, R.; Artico, M.; Bruno, B.; Massa, S.; Novellino, E.; Greco, G.; Marongiu, M. E.; Pani, A.; De Montis, A and La Colla, P. Synthesis and biological evaluation of 5H-indolo[3,2-b][1,5]benzothiazepine derivatives, designed as conformationally constrained analogues of the human immunodeficiency virus type 1 reverse transcriptase inhibitor L-737,126. *Antiviral Chem. Chemother.* 1998, 9, 139–148.
22. Fredenhagen, A.; Petersen, F.; Tintelnot-Blomley, M.; Rosel, J.; Mett, H and Hug, P. J. Semicochliodinol A and B: Inhibitors of HIV-1 protease and EGF-R protein Tyrosine Kinase related to Asterriquinones produced by the fungus *Chrysosporium nerdarium. Antibiotics*, 1997, 50, 395–401.
23. Kato, M.; Ito, K.; Nishino, S.; Yamakuni, H.; Takasugi, H. New 5-HT$_3$ (Serotonin-3) receptor antagonists. IV. Synthesis and structure-activity relationships of azabicycloalkaneacetamide derivatives. *Chem. Pharm. Bull.*, 1995, 43, 1351–1357.
24. Levacher, V.; Benoit, R.; Duflos, J; Dupas, G.; Bourguignon, J.; Queguiner, G. Broadening the scope of NADH models by using chiral and non chiral pyrrolo [2,3-b]pyridine derivatives. *Tetrahedron*, 1991, 47, 429–440.
25. (a) Mahadevan, I; Rasmussen, M. Synthesis of pyrrolopyridines (Azaindoles). *J. Het. Chem.*, 1992, 29, 359–367. (b) Hands, D.; Bishop, B.; Cameron, M.; Edwards, J. S.; Cottrell, I. F.; Wright, S. H. B. A convient method for the preparation of 5-, 6- and 7-azaindoles and their derivatives. *Synthesis*, 1996, 877–882. (c) Dobson, D.; Todd, A.; Gilmore, J. The Synthesis of 7-Alkoxyindoles. *Synth. Commun.* 1991, 21, 611–617.
26 Sakamoto, T; Kondo, Y; Iwashita, S; Yamanaka, H Condensed Heteroaromatic Ring Systems. XII. Synthesis of Indole Derivatives from Ethyl 2-Bromocarbanilates. *Chem. Pharm. Bull.* 1987, 35, 1823–1828
27. Shadrina, L. P.; Dormidontov, Yu. P.; Ponomarev, V, G.; Lapkin, I. I. Reactions of organomagnesium derivatives of 7-aza- and benzoindoles with diethyl oxalate and the reactivity of ethoxalylindoles. *Khim. Geterotsikl. Soedin.*, 1987, 1206–1209.
28. Sycheva, T. V.; Rubtsov, N. M.; Sheinker, Yu. N.; Yakhontov, L. N. Some reactions of 5-cyano-6-chloro-7-azaindoles and lactam-lactim tautomerism in 5-cyano-6-hydroxy-7-azaindolines. *Khim. Geterotsikl. Soedin.*, 1987, 100–106.
29. Li, H.; Jiang, X.; Ye, Y.-H.; Fan, C.; Romoff, T.; Goodman, M. 3(Diethoxyphosphoryloxy)-1,2,3-benzotriazin-4(3H)-one (DEPBT): A new coupling reagent with remarkable resistance to racemization. *Organic Lett.*, 1999, 1, 91–93.
30. (a) Desai, M.; Watthey, J. W. H.; Zuckerman, M. A convenient preparation of 1-aroylpiperazines. *Org. Prep. Proced. Int.*, 1976, 8, 85–86. (b) Adamczyk, M.; Fino, J. R. Synthesis of procainamide metabolites. N-acetyl desethylprocainamide and desethylprocainamide. *Org. Prep. Proced. Int.* 1996, 28, 470–474. (c) Rossen, K.; Weissman, S. A.; Sager, J.; Reamer, R. A.; Askin, D.; Volante, R. P.; Reider, P. J. Asymmetric Hydrogenation of tetrahydropyrazines: Synthesis of (S)-piperazine 2-tert-butylcarboxamide, an intermediate in the preparation of the HIV protease inhibitor Indinavir. *Tetrahedron Lett.*, 1995, 36, 6419–6422. (d) Wang, T.; Zhang, Z.; Meanwell, N. A. Benzoylation of Dianions: Preparation of mono-Benzoylated Symmetric Secondary Diamines. *J. Org. Chem.*, 1999, 64, 7661–7662. (e) Wang, T.; Zhang, Z.; Meanwell, N. A. Regioselective mono-Benzoylation of Unsymmetrical Piperazines. *J. Org. Chem.* 2000, 65, 4740–4742.
31. Harada, N.; Kawaguchi, T.; Inoue, I.; Ohashi, M.; Oda, K.; Hashiyama, T.; Tsujihara, K. Synthesis and antitumor activity of quaternary salts of 2-(2'-oxoalkoxy)-9-hydroxyellipticines. *Chem. Pharm. Bull.*, 1997, 45, 134–137.
32. Antonini, I.; Claudi, F.; Cristalli, G.; Franchetti, P.; Crifantini, M.; Martelli, S. Synthesis of 4-amino-1-□β-D-ribofuranosyl-1H-pyrrolo[2,3-b]pyridine (1-Deazatubercidin) as a potential antitumor agent. *J. Med. Chem.*, 1982, 25, 1258–1261.
33. (a) Schneller, S. W.; Luo, J.-K. Synthesis of 4-amino-1H-pyrrolo[2,3-b]pyridine (1,7-Dideazaadenine) and 1H-pyrrolo[2,3-b]pyridin-4-ol (1,7-Dideazahypoxanthine). *J. Org. Chem.*, 1980, 45, 4045–4048. (b)

Wozniak, M.; Grzegozek, M. Amination of 4-nitroquinoline with liquid methylamine/Potassium Permanganate *Chemistry of Heterocyclic Compounds* 1998, 837–840.

34. Shiotani, S.; Tanigochi, K. Furopyridines. XXII [1]. Elaboration of the C-substitutents alpha to the heteronitrogen atom of furo[2,3-b]-, -[3.2-b]-, -[2.3-c]- and -[3,2-c]pyridine. *J. Heterocyclic. Chem.*, 1997, 34, 901–907.

35. Minakata, S.; Komatsu, M.; Ohshiro, Y. Regioselective functionalization of 1H-pyrrolo[2,3-b]pyridine via its N-oxide. *Synthesis*, 1992, 661–663.

36. Klemm, L. H.; Hartling, R. Chemistry of thienopyridines. XXIV. Two transformations of thieno[2,3-b] pyridine 7-oxide (1). *J. Heterocyclic Chem.*, 1976, 13, 1197–1200.

37. Shiotani, S.; Taniguchi, K. Furopyridunes. XXIII [1]. Synthesis and Reactions of Chloropyridine Derivatives of Furo[2,3-b]-, -[2,3-c]- and -[3,2-c]pyridine. *J. Heterocyclic Chem.* 1997, 34, 925–929.

38. Hayashida, M.; Honda, H.; Hamana, M. Deoxygenative 2-Alkoxylation of Quinoline 1-Oxide. *Heterocycles* 1990, 31, 1325–1331.

39. Miura, Y.; Takaku, S.; Fujimura, Y.; Hamana, M. Synthesis of 2,3-Fused quinolines from 3-Substituted Quinoline 1-Oxide. Part 1. *Heterocycles* 1992, 34, 1055–1063.

40. Solekhova, M. A.; Kurbatov, Yu. V. A New Reaction of Reductive Amination of Quinoline N-Oxide with 2-Aminopyridine. *Zh. Org. Khim.* 1996, 32, 956.

41. (a) Regnouf De Vains, J. B.; Papet, A. L.; Marsura, A. New symmetric and unsymmetric polyfunctionalized 2,2'-bipyridines. *J. Het. Chem.*, 1994, 31, 1069–1077. (b) Miura, Y.; Yoshida, M.; Hamana, M. Synthesis of 2,3-fused quinolines from 3-substituted quinoline 1-oxides. Part II, *Heterocycles*, 1993, 36, 1005–1016. (c) Profft, V. E.; Rolle, W. Uber 4-merkaptoverbindungendes 2-methylpyridins. *J. Prakt. Chem.*, 1960, 283 (11), 22–34.

42. Nesi, R.; Giomi, D.; Turchi, S.; Tedeschi, P., Ponticelli, F. A new one step synthetic approach to the isoxazolo[4,5-b]pyridine system. *Synth. Comm.*, 1992, 22, 2349–2355.

43. (a) Walser, A.; Zenchoff, G.; Fryer, R. I. Quinazolines and 1,4-benzodiazepines. 75. 7-Hydroxyaminobenzodiazepines and derivatives. *J. Med. Chem.*, 1976, 19, 1378–1381. (b) Barker, G.; Ellis, G. P. Benzopyrone. Part I. 6-Amino- and 6-hydroxy-2-subtituted chromones. *J. Chem. Soc.*, 1970, 2230–2233.

44. Ayyangar, N. R.; Lahoti, R J.; Daniel, T. An alternate synthesis of 3,4-diaminobenzophenone and mebendazole. *Org. Prep. Proced. Int.*, 1991, 23, 627–631.

45. Mahadevan, I.; Rasmussen, M. Ambident heterocyclic reactivity: The alkylation of pyrrolopyridines (azaindoles, diazaindenes). *Tetrahedron*, 1993, 49, 7337–7352.

46. (a) Sakamoto, T.; Ohsawa, K. Palladium-catalyzed cyanation of aryl and heteroaryl iodides with copper(I) cyanide. *J. Chem. Soc, Perkin Trans* 1 1999, 2323–2326. (b) Halley, F.; Sava, X. Synthesis of 5-cyanoindazole and 1-methyl and 1-aryl-5-cyanoindazoles. *Synth. Commun.* 1997, 27, 1199–1207. (c) Yamaguchi, S.; Yoshida, M.; Miyajima, I.; Araki, T.; Hirai, Y. The Synthesis of Benzofuroquinolines. X. Some Benzofuro[3,2-c]isoquinoline Derivatives. *J. Heterocyclic Chem.* 1995, 32, 1517–1519. (d) Funhoff, D. J. H.; Staab, H. A. Cyclo [d.e.d.e.e.d.e.e.]decaakisbenzene, a New Cycloarene. *Angew Chem., Int. Ed. Engl.* 1986, 25, 742.

47. Klimesova, V.; Otcenasek, M.; Waisser, K. Potential antifungal agents. Synthesis and activity of 2-alkylthiopyridine-4-carbothioamides. *Eur. J. Med. Chem.* 1996, 31, 389–395.

48. Katritzky, A.; Rachwal, S.; Smith, T. P.; Steel, P. J. Synthesis and Reactivity of 2,6-Diamino-4-methyl-3-pyridinecarbonitrile. *J. Heterocyclic Chem.* 1995, 32, 979–984.

49. (a) Miletin, M.; Harti, J.; Machacek, M. Synthesis of Some Anides of 2-Alkyl-4-pyridinecarboxylic Acids and Their Photosynthsis-Inhibiting Activity. *Collect. Czech. Chem. Commun.* 1997, 62, 672–678. (b) Shiotani, S.; Taniguchi, K. Furopyridines. XVII [1]. Cyanation, Chlorination and Nitration of Furo[3,2-b]pyridine N-Oxide. *J. Heterocyclic Chem.* 1996, 33, 1051–1056. (c) El Hadri, A.; Leclerc, G. A Convenient Synthesis of cis-4-(Sulfomethyl)-piperidine-2-carboxylic Acid: NMR Assignment. *J. Heterocyclic Chem.* 1993, 30, 631–635.

50. (a) Heirtzler, F. R. Preparation of Non-Symmetrical 2,3-Bis-(2,2'-oligopyridyl)pyrazines via 1,2-Disubstituted Ethanones. *Synlett.* 1999, 1203–1206. (b) Norrby, T.; Roerje, A.; Zhang, L.; Aakermark, B. Regioselective Functionalization of 2,2'-Bipyridine and Transformations into Unsymmetric Ligands for Coordination Chemistry. *Acta Chem. Scand.* 1998, 52, 77–85.

51. (a) Sitsun'van; Borisova, E. Ya.; Golovkov, P. V.; Burdelev, O. T.; Guzeneva, N. A.; Cherkashin, M. I.; Tolstikov, G. A. *Zh Org Khim* 1995, 31, 1169–1172. (b) Reich, S. H.; Melnick, M.; Pino, M. J.; Fuhry, M. A. M.; Trippe, A. J.; Appelt, K.; Davies, J. F. II; Wu, B.-W.; Musick, L. Structure-Based Design and Synthesis of Substituted 2-Butanols as Nonpeptidic Inhibitors of HIV Protease: Secondary Amide Series. *J. Med. Chem.* 1996, 39, 2781–2794. (c) Salfetnikova, Yu. N.; Vasil'ev, A. V.; Rudenko, A. P. *Zh. Org. Khim.* 1998, 34, 888–894.

52. (a) Oki, A. R.; Morgan, R. J. An Efficient Preparation of 4,4'-Dicarboxy-2,2'-bipyridine. *Synth. Commun.* 1995, 25, 4093–4097. (b) Garelli, N.; Vierling, P. Synthesis of New Amphiphilic Perfluoroalkylated Bipyridines. *J. Org. Chem.* 1992, 57, 3046–3051. (c) Koyama, J.; Ogura, T.; Tagahara, K. Diels-Alder Reaction of 1,2,3-Triazine with Aldehyde Enamine. *Heterocycles* 1994, 38, 1595–1600.

53. (a) Yasuda, M.; Boger, D. L. Streptonigrin and Lavendacymin Partial Structures. Preparation of 7-Amino-2-(2'-pyridyl)quinoline-5,8-quinone-6'-carboxylic Acid: A Probe for the Minium, Potent Pharmacophore of the Naturally Occurring Antitumor-Antibiotics. *J. Heterocyclic Chem.* 1987, 24, 1253–1260. (b) Levine, R.; Sneed, J. K. The Relative Reactivities of the Isomeric Methyl Pyridinecarboxylate in the Acylation of Certain Ketones. The Synthesis of □-Diketones Containing Pyridine Rings. *J. Am. Chem. Soc.* 1951, 73, 5614–5616. (c) Hoemann, M. Z.; Melikian-Badalian, A.; Kumarave, G.; Hauske, J. R. Solid-Phase Synthesis of Substituted Quinoline and Isoquinoline Derivatives Using Heterocyclic N-oxide Chemistry. *Tetrahedron Lett.* 1998, 39, 4749–4752.

54. (a) Norman, M. H.; Navas, F. III; Thompson, J. B.; Rigdon, G. C. Synthesis and Evaluation of Heterocyclic Carboxamides as Potential Antipsychotic Agents. *J. Med. Chem.* 1996, 39, 4692–4703. (b) Jursic, B. S.; Zdravkovski, Z. A Simple Preparation of Amides from Acids and Amines by Heating of Their Mixture. *Synth. Commun.* 1993, 23, 2761–2770. (c) Strekowski, L.; Gulevich, Y.; Baranowski, T. C.; Parker, A. N.; Kiselyov, A. S.; Lin, S.-Y.; Tanious, F. A.; Wilson, W. D. Synthesis and Structure-DNA Binding Relationship Analysis of DNA Triple-Helix Specific Intercalators. *J. Med. Chem.* 1996, 39, 3980–3983. (d) Shi, G.; Takagishi, S.; Schlosser, M. Metalated Fluoropyridines and Fluoroquinolines as Reactive Intermediates: New Ways for Their Regioselective Generation. *Tetrahedron* 1994, 50, 1129–1134.

55. Chen, B. K.; Saksela, K.; Andino, R.; Baltimore, D. Distinct modes of human immunodeficiency type 1 proviral latency revealed by superinfection of nonproductively infected cell lines with recombinant luciferase-encoding viruses. *J. Virol.*, 1994, 68, 654–660.
56. Clark, G. J.; Deady, L. W. "Synthetic Uses of the Sequential Ring Positional Reactivity in Pyridin-3-ol and Derivatives" *Aust. J. Chem.* 1981, 34, 927–932.
57. Anderson, H. J.; Loader, C. E.; Foster, A. "Pyrrole chemistry. XXII. A "one-pot" synthesis of some 4-acylpyrrole-2-carboaldehydes from pyrrole" *Can. J. Chem.* 1980, 58, 2527–2530.
58. Suzuki, H.; Iwata, C.; Sakurai, K.; Tokumoto, K.; Takahashi, H.; Hanada, M.; Yokoyama, Y.; Murakami, Y. "A General Synthetic Route for 1-Substituted 4-Oxygenated β-Carbolines (Synthetic Studies on Indoles and Related Compounds 41)" *Tetrahedron*, 1997, 53(5), 1593–1606.
59. Marfat, A.; and Robinson, R. P.; "Azaoxindole Derivatives" U.S. Pat. No. 5,811,432 1998.

SUMMARY OF THE INVENTION

The present invention comprises compounds of Formula I, or pharmaceutically acceptable salts thereof, which are effective antiviral agents, particularly as inhibitors of HIV.

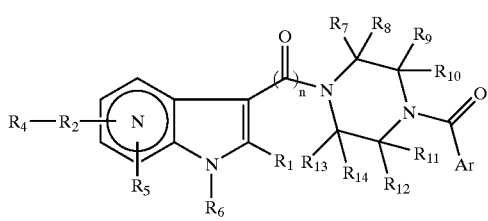

wherein:

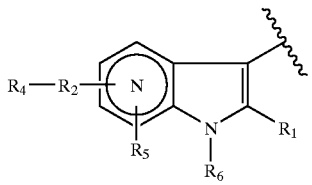

is selected from the group consisting of

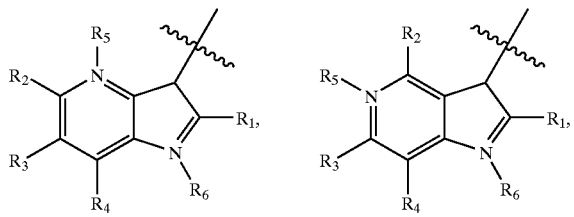

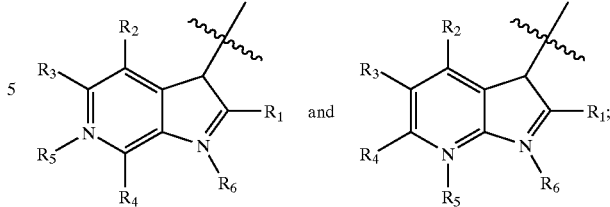

$R_1$, $R_2$, $R_3$, $R_4$ are each independently selected from the group consisting of H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl, halogen, CN, phenyl, nitro, $OC(O)R_{15}$, $C(O)R_{15}$, $C(O)OR_{16}$, $C(O)NR_{17}R_{18}$, $OR_{19}$, $SR_{20}$ and $NR_{21}R_{22}$;

$R_{15}$, is independently selected from the group consisting of H, $C_1$–$C_6$ alkyl, $C_3$–$C_6$ cycloalkyl, $C_2$–$C_6$ alkenyl and $C_4$–$C_6$ cycloalkenyl;

$R_{16}$, $R_{19}$, and $R_{20}$ are each independently selected from the group consisting of H, $C_1$–$C_6$ alkyl, $C_{1-6}$ alkyl substituted with one to three halogen atoms, $C_3$–$C_6$ cycloalkyl, $C_2$–$C_6$ alkenyl, $C_4$–$C_6$ cycloalkenyl, and $C_3$–$C_6$ alkynyl; provided the carbon atoms which comprise the carbon-carbon triple bond of said $C_3$–$C_6$ alkynyl are not the point of attachment to the oxygen or sulfur to which $R_{16}$, $R_{19}$, or $R_{20}$ is attached;

$R_{17}$ and $R_{18}$ are each independently selected from the group consisting of H, $C_1$–$C_6$ alkyl, $C_3$–$C_6$ cycloalkyl, $C_3$–$C_6$ alkenyl, $C_4$–$C_6$ cycloalkenyl and $C_3$–$C_6$ alkynyl; provided the carbon atoms which comprise the carbon-carbon double bond of said $C_3$–$C_6$ alkenyl or the carbon-carbon triple bond of said $C_3$–$C_6$ alkynyl are not the point of attachment to the nitrogen to which $R_{17}$ and $R_{18}$ is attached;

$R_{21}$ and $R_{22}$ are each independently selected from the group consisting of H, OH, $C_1$–$C_6$ alkyl, $C_3$–$C_6$ cycloalkyl, $C_3$–$C_6$ alkenyl, $C_5$–$C_6$ cycloalkenyl, $C_3$–$C_6$ alkynyl and $C(O)R_{23}$; provided the carbon atoms which comprise the carbon-carbon double bond of said $C_3$–$C_6$ alkenyl, $C_4$–$C_6$ cycloalkenyl, or the carbon-carbon triple bond of said $C_3$–$C_6$ alkynyl are not the point of attachment to the nitrogen to which $R_{21}$ and $R_{22}$ is attached;

$R_{23}$ is selected from the group consisting of H, $C_1$–$C_6$ alkyl, $C_3$–$C_6$ cycloalkyl, $C_2$–$C_6$ alkenyl, $C_4$–$C_6$ cycloalkenyl, and $C_2$–$C_6$ alkynyl;

$R_5$ is $(O)_m$, wherein m is 0 or 1;

n is 1 or 2;

$R_6$ is selected from the group consisting of H, $C_1$–$C_6$ alkyl, $C_3$–$C_6$ cycloalkyl, $C_4$–$C_6$ cycloalkenyl, $C(O)R_{24}$, $C(O)OR_{25}$, $C(O)NR_{26}R_{27}$, $C_3$–$C_6$ alkenyl and $C_3$–$C_6$ alkynyl; provided the carbon atoms which comprise the carbon-carbon double bond of said $C_3$–$C_6$ alkenyl or the carbon-carbon triple bond of said $C_3$–$C_6$ alkynyl are not the point of attachment to the nitrogen to which $R_6$ is attached;

$R_{24}$ is selected from the group consisting of H, $C_1$–$C_6$ alkyl, $C_3$–$C_6$ cycloalkyl, $C_3$–$C_6$ alkenyl, $C_4$–$C_6$ cycloalkenyl, and $C_3$–$C_6$ alkynyl;

$R_{25}$ is selected from the group consisting of $C_1$–$C_6$ alkyl, $C_3$–$C_6$ cycloalkyl, $C_2$–$C_6$ alkenyl, $C_4$–$C_6$ cycloalkenyl, and $C_3$–$C_6$ alkynyl; provided the carbon atoms which comprise the carbon-carbon triple bond of said $C_3$–$C_6$ alkynyl are not the point of attachment to the oxygen to which $R_{25}$ is attached;

$R_{26}$ and $R_{27}$ are each independently selected from the group consisting of H, $C_1$–$C_6$ alkyl, $C_3$–$C_6$ cycloalkyl, $C_3$–$C_6$ alkenyl, $C_5$–$C_6$ cycloalkenyl, and $C_3$–$C_6$ alkynyl; provided the carbon atoms which comprise the carbon-carbon double bond of said $C_3$–$C_6$ alkenyl, $C_5$–$C_6$ cycloalkenyl, or the carbon-carbon triple bond of said $C_3$–$C_6$ alkynyl are not the point of attachment to the nitrogen to which $R_{26}$ and $R_{27}$ are attached;

$R_7$, $R_8$, $R_9$, $R_{10}$, $R_{11}$, $R_{12}$, $R_{13}$, and $R_{14}$ are each independently selected from the group consisting of H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl, $CR_{28}R_{29}OR_{30}$, $C(O)R_{31}$, $CR_{32}(OR_{33})OR_{34}$, $CR_{35}NR_{36}R_{37}$, $C(O)OR_{38}$, $C(O)NR_{39}R_{40}$, $CR_{41}R_{42}F$, $CR_{43}F_2$ and $CF_3$;

$R_{28}$, $R_{29}$, $R_{30}$, $R_{31}$, $R_{32}$, $R_{35}$, $R_{41}$, $R_{42}$ and $R_{43}$ are each independently selected from the group consisting of H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl and $C(O)R_{44}$;

$R_{33}$, $R_{34}$ and $R_{38}$ are each independently selected from the group consisting of H, $C_1$–$C_6$ alkyl, $C_3$–$C_6$ cycloalkyl, $C_3$–$C_6$ alkenyl, $C_4$–$C_6$ cycloalkenyl, and $C_3$–$C_6$ alkynyl; provided the carbon atoms which comprise the carbon-carbon triple bond of said $C_3$–$C_6$ alkynyl are not the point of attachment to the oxygen to which $R_{34}$ and $R_{38}$ are attached;

$R_{36}$ and $R_{37}$ are each independently selected from the group consisting of H, $C_1$–$C_6$ alkyl, $C_3$–$C_6$ cycloalkyl, $C_3$–$C_6$ alkenyl, $C_4$–$C_6$ cycloalkenyl, and $C_3$–$C_6$ alkynyl; provided the carbon atoms which comprise the carbon-carbon triple bond of said $C_3$–$C_6$ alkynyl are not the point of attachment to the nitrogen to which $R_{36}$ and $R_{37}$ are attached;

$R_{39}$ and $R_{40}$ are each independently selected from the group consisting of H, $C_1$–$C_6$ alkyl, $C_3$–$C_6$ cycloalkyl, $C_2$–$C_6$ alkenyl, $C_4$–$C_6$ cycloalkenyl, and $C_3$–$C_6$ alkynyl; provided the carbon atoms which comprise the carbon-carbon triple bond of said $C_3$–$C_6$ alkynyl are not the point of attachment to the nitrogen to which $R_{39}$ and $R_{40}$ are attached;

$R_{44}$ is selected from the group consisting of H, $C_1$–$C_6$ alkyl, $C_3$–$C_6$ cycloalkyl, $C_2$–$C_6$ alkenyl, $C_4$–$C_6$ cycloalkenyl, and $C_2$–$C_6$ alkynyl;

Ar is selected from the group consisting of

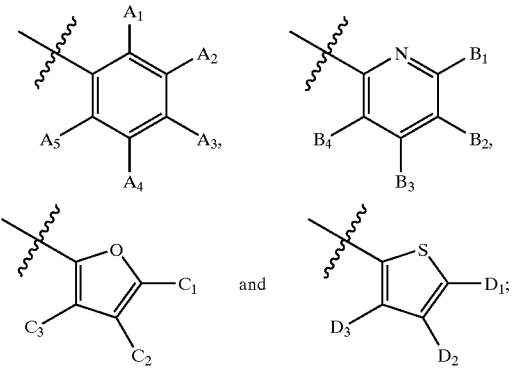

$A_1$, $A_2$, $A_3$, $A_4$, $A_5$, $B_1$, $B_2$, $B_3$, $B_4$, $C_1$, $C_2$, $C_3$, $D_1$, $D_2$, and $D_3$ are each independently selected from the group consisting of H, CN, halogen, $NO_2$, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl, $OR_{45}$, $NR_{46}R_{47}$, $SR_{48}$, $N_3$ and CH(—N=N—)—$CF_3$;

$R_{45}$ is selected from the group consisting of H, $C_1$–$C_6$ alkyl, $C_3$–$C_6$ cycloalkyl, $C_2$–$C_6$ alkenyl, $C_4$–$C_6$ cycloalkenyl and $C_3$–$C_6$ alkynyl; provided the carbon atoms which comprise the carbon-carbon triple bond of said $C_3$–$C_6$ alkynyl are not the point of attachment to the oxygen to which $R_{45}$ is attached;

$R_{46}$ and $R_{47}$ are each independently selected from the group consisting of H, $C_1$–$C_6$ alkyl, $C_3$–$C_6$ cycloalkyl, $C_3$–$C_6$ alkenyl, $C_5$–$C_6$ cycloalkenyl, $C_3$–$C_6$ alkynyl and $C(O)R_{50}$; provided the carbon atoms which comprise the carbon-carbon double bond of said $C_5$–$C_6$ alkenyl, $C_4$–$C_6$ cycloalkenyl, or the carbon-carbon triple bond of said $C_3$–$C_6$ alkynyl are not the point of attachment to the nitrogen to which $R_{46}$ and $R_{47}$ are attached;

$R_{48}$ is selected from the group consisting of H, $C_1$–$C_6$ alkyl, $C_3$–$C_6$ cycloalkyl, $C_2$–$C_6$ alkenyl, $C_4$–$C_6$ cycloalkenyl, $C_3$–$C_6$ alkynyl and $C(O)R_{49}$; provided the carbon atoms which comprise the carbon-carbon triple bond of said $C_3$–$C_6$ alkynyl are not the point of attachment to the sulfur to which $R_{48}$ is attached;

$R_{49}$ is $C_1$–$C_6$ alkyl or $C_3$–$C_6$ cycloalkyl; and $R_{50}$ is selected from the group consisting of H, $C_1$–$C_6$ alkyl, and $C_3$–$C_6$ cycloalkyl.

Preferred are compounds of Formula I or pharmaceutically acceptable salts thereof wherein $R_2$–$R_4$ is independently H, —$OCH_3$, —$OCH_2CF_3$, —OiPr, —OnPr, halogen, CN, $NO_2$, $C_1$–$C_6$ alkyl, NHOH, $NH_2$, Ph, $SR_{20}$, or $N(CH_3)_2$.

Also preferred are compounds of Formula I wherein one or two of $R_7$–$R_{14}$ is independently methyl and the other substituents are hydrogen.

Also preferred are compounds of Formula I wherein one of $A_1$–$A_5$, $B_1$–$B_4$, $C_1$–$C_3$ or $D_1$–$D_3$ are either hydrogen, halogen, or amino and the remaining substituents are hydrogen.

Also preferred are compounds of the formula below:

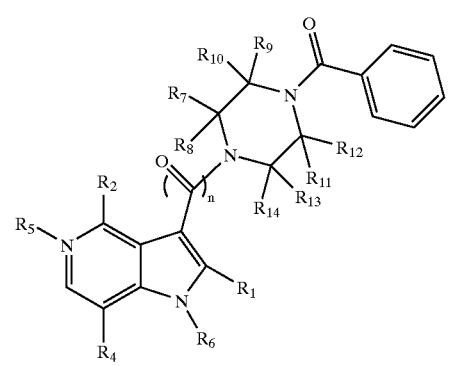

wherein:

$R_2$ is H, F, Cl, Br, OMe, CN, or OH;

$R_4$ is $C_1$–$C_6$ alkyl, $C_2$–$C_6$ alkenyl, $C_3$–$C_6$ cycloalkyl, $C_5$–$C_6$ cycloalkenyl, Cl, OMe, CN, OH, $C(O)NH_2$, C(O)NHMe, C(O)NHEt, Ph or —$C(O)CH_3$;

n is 2;

$R_8$, $R_9$, $R_{10}$, $R_{11}$, $R_{12}$, $R_{13}$ and $R_{14}$ are each independently H or CH3, provided up to two of these substituents may be methyl;

$R_1$ is hydrogen;

$R_5$ is unsubstituted; and $R_6$ is hydrogen or methyl.

A most preferred aspect of the invention are compounds or pharmaceutically acceptable salts thereof of the Formula

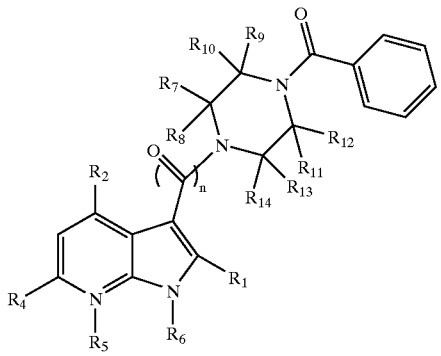

wherein:

R$_2$ is H, —OCH$_3$, —OCH$_2$CF$_3$, —OPr, halogen, CN, NO$_2$, or NHOH;

R$_4$ is H, -halogen, —CN, or hydroxy;

One or two members of R$_7$–R$_{14}$ is methyl and the remaining members are hydrogen;

n is 2;

R$_1$ is hydrogen;

R$_5$ is (O)$_m$, where is O; and

R$_6$ is hydrogen, methyl, or allyl.

Another most preferred aspect of the invention are compounds of the formula below wherein:

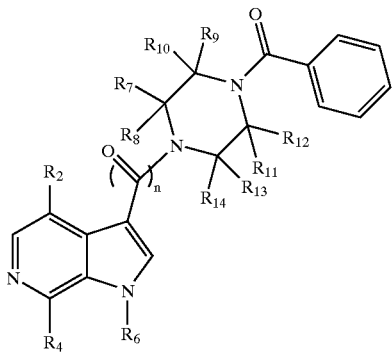

wherein:

R$_2$ is selected from the group consisting of H, F, Cl, Br, OMe, CN, and OH;

R$_4$ is selected from the group consisting of H, C$_1$–C$_6$ alkyl, C$_2$–C$_6$ alkenyl, C$_3$–C$_6$ cycloalkyl, C$_5$–C$_6$ cycloalkenyl, Cl, OMe, CN, OH, C(O)NH$_2$, C(O)NHMe, C(O)NHEt, phenyl and —C(O)CH$_3$;

n is 2;

R$_8$, R$_9$, R$_{10}$, R$_{11}$, R$_{12}$, R$_{13}$, and R$_{14}$ are each independently H or CH$_3$, provided 0–2 of the members of the group R$_8$, R$_9$, R$_{10}$, R$_{11}$, R$_{12}$, R$_{13}$, and R$_{14}$ may be CH$_3$ and the remaining members of the group R$_8$, R$_9$, R$_{10}$, R$_{11}$, R$_{12}$, R$_{13}$, and R$_{14}$ are H; and R$_6$ is H or CH$_3$.

Another most preferred aspect of the inventions are compounds of formula:

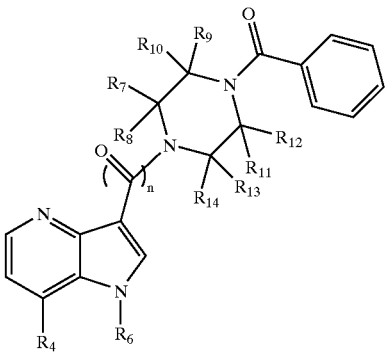

wherein:

R$_4$ is selected from the group consisting of H, C$_1$–C$_6$ alkyl, C$_2$–C$_6$ alkenyl, C$_3$–C$_6$ cycloalkyl, C$_5$–C$_6$ cycloalkenyl, Cl, OMe, CN, OH, C(O)NH$_2$, C(O)NHMe, C(O)NHEt, phenyl and —C(O)CH$_3$;

n is 2;

R$_8$, R$_9$, R$_{10}$, R$_{11}$, R$_{12}$, R$_{13}$, and R$_{14}$ are each independently H or CH$_3$, provided 0–2 of the members of the group R$_8$, R$_9$, R$_{10}$, R$_{11}$, R$_{12}$, R$_{13}$, and R$_{14}$ may be CH$_3$ and the remaining members of the group R$_8$, R$_9$, R$_{10}$, R$_{11}$, R$_{12}$, R$_{13}$, and R$_{14}$ are H; and R$_6$ is H or CH$_3$.

Since the compounds of the present invention, may possess asymmetric centers and therefore occur as mixtures of diastereomers and enantiomers, the present invention includes the individual diastereoisomeric and enantiomeric forms of the compounds of Formula I.

Another embodiment of the invention is a pharmaceutical composition which comprises an antiviral effective amount of a compound of Formula I.

Another embodiment of the present invention is a method for treating mammals infected with a virus, wherein said virus is HIV, comprising administering to said mammal an antiviral effective amount of a compound of Formula I.

Another embodiment of the present invention is a method for treating mammals infected with a virus, such as HIV, comprising administering to said mammal an antiviral effective amount of a compound of Formula I in combination with an antiviral effective amount of an AIDS treatment agent selected from the group consisting of: (a) an AIDS antiviral agent; (b) an anti-infective agent; (c) an immunomodulator; and (d) HIV entry inhibitors.

DETAILED DESCRIPTION OF THE INVENTION

The preparative procedures and anti-HIV-1 activity of the novel azaindole piperazine diamide analogs of Formula I are summarized below. The definition of various terms follow.

The term "C$_{1-6}$ alkyl" as used herein and in the claims (unless the context indicates otherwise) means straight or branched chain alkyl groups such as methyl, ethyl, propyl, isopropyl, butyl, isobutyl, t-butyl, amyl, hexyl and the like. Similarly, "C$_{1-6}$ alkenyl" or "C$_{1-6}$ alkynyl" includes straight or branched chain groups.

"Halogen" refers to chlorine, bromine, iodine or fluorine.

Physiologically acceptable salts and prodrugs of compounds disclosed herein are within the scope of this invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

In the method of the present invention, the term "antiviral effective amount" means the total amount of each active component of the method that is sufficient to show a meaningful patient benefit, i.e., healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with HIV infection.

The present invention is also directed to combinations of the compounds with one or more agents useful in the treatment of AIDS. For example, the compounds of this invention may be effectively administered, whether at periods of pre-exposure and/or post-exposure, in combination with effective amounts of the AIDS antivirals, immunomodulators, antiinfectives, or vaccines, such as those in the following table.

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |
| Amprenivir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin | Adria Laboratories | ARC |

-continued

| Drug Name | Manufacturer | Indication |
|---|---|---|
| LM 427 | (Dublin, OH) Erbamont (Stamford, CT) | |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266) (-)6-Chloro-4-(S)-cyclopropylethynyl-4(S)-trifluoro-methyl-1,4-dihydro-2H-3,1-benzoxazin-2-one, STOCRINE | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in |

-continued

| Drug Name | Manufacturer | Indication |
|---|---|---|
| | | combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246, 738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal Meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT Therapy |
| Recombinant Human | Serono | AIDS-related |

| Drug Name | Manufacturer | Indication |
|---|---|---|
| Growth Hormone | | wasting, cachexia |
| Megestrol Acetate | Bristol-Myers Squibb | Treatment of Anorexia assoc. W/AIDS |
| Testosterone | Alza, Smith Kline | AIDS-related wasting |
| Total Enteral Nutrition | Norwich Eaton Pharmaceuticals | Diarrhea and malabsorption Related to AIDS |

Additionally, the compounds of the invention herein may be used in combination which include more than three anti HIV drugs. Combinations of four or even five HIV drugs are being investigated and the compounds of this invention would be expected to be a useful component of such combinations.

Additionally, the compounds of the invention herein may be used in combination with another class of agents for treating AIDS which are called HIV entry inhibitors. Examples of such HIV entry inhibitors are discussed in DRUGS OF THE FUTURE 1999, 24(12), pp. 1355–1362; CELL, Vol. 9, pp. 243–246, Oct. 29, 1999; and DRUG DISCOVERY TODAY, Vol. 5, No. 5, May 2000, pp. 183–194.

It will be understood that the scope of combinations of the compounds of this invention with AIDS antivirals, immunomodulators, anti-infectives, HIV entry inhibitors or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridylmethyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Finally a new protease inhibitor, BMS-232632, which is currently undergoing clinical trials may become a preferred inhibitor. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

Parent azaindoles such as 4-azaindole, 5-azaindole, 6-azaindole, or 7-azaindole are prepared by the methods described in the literature (Mahadevan et al, Ref. 25(a)) or Hands et. al. Ref 25 (b) are available from commercial sources (7-azaindole from Aldrich Co.). This reference and similar references show some examples of substituted aza indoles. Chemist skilled in the art can recognize that the general methodology can be extended to azaindoles which have different substituents in the starting materials. Azaindoles are also prepared via the routes described in Scheme 1 and Scheme 2.

Scheme 1

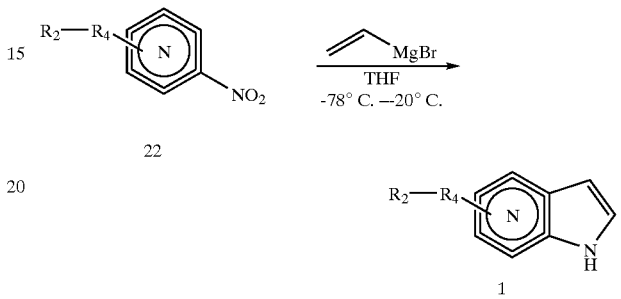

In Scheme 1, the Bartoli indole synthesis (Dobson et al, Ref. 25 (C)) is extended to prepare substituted azaindoles. Nitropyridine 22 was reacted with an excess of vinyl magnesium bromide at −78° C. After warming up to −20° C., the reaction provides the desired azaindole 1. Generally these temperature ranges are optimal but in specific examples may be varied usually by no more than 20° C. but occasionally by more in order to optimize the yield. The vinyl magnesium bromide may be obtained commercially as a solution in tetrahydrofuran or sometimes more optimally may be prepared fresh from vinyl bromide and magnesium using literature procedures which are well known in the art. Vinyl magnesium chloride can also be used in some examples.

Scheme 2

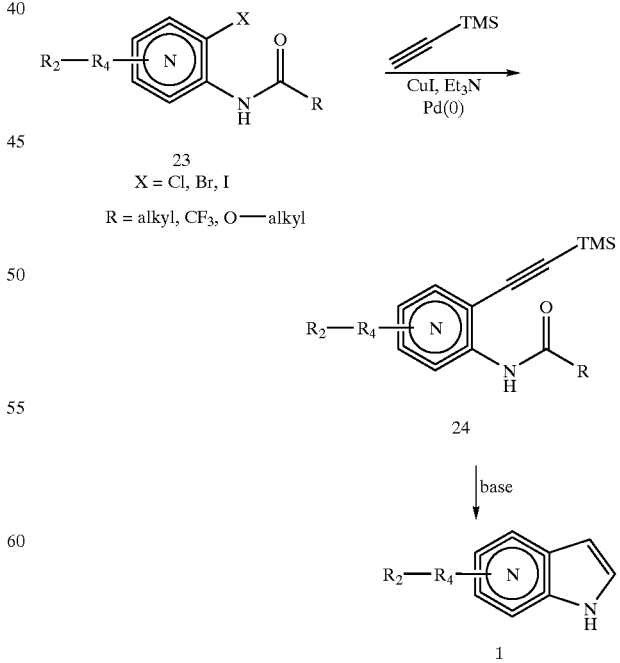

In Scheme 2, acetylene is coupled onto a halo-pyridine 23 using a Pd (0) catalyst to furnish 24. Subsequent treatment with base effects cyclization of 24 to afford azaindole 1(Sakamoto et al, Ref. 26). Suitable bases for the second step include sodium methoxide or other sodium, lithium, or potassium alkoxide bases.

General procedures to prepare azaindole piperazine diamide 5 of Formula I are described in Scheme 3 and Scheme 4.

Scheme 3

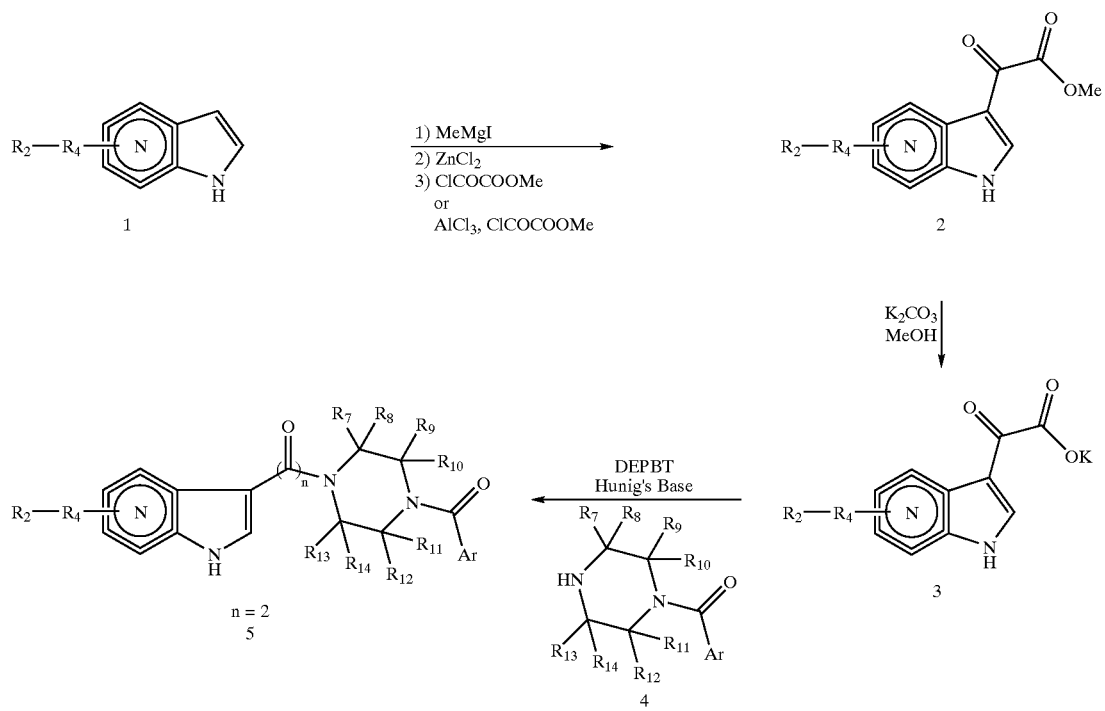

An azaindole 1, was reacted with MeMgI (methyl magnesium iodide) and $ZnCl_2$ (zinc chloride), followed by the addition of ClCOCOOMe (methyl chlorooxoacetate) to afford aza-indole glyoxyl methyl ester 2 (Shadrina et al, Ref. 27). Alternatively, compound 2 can be prepared by reaction of aza-indole 1 with an excess of ClCOCOOMe in the presence of $AlCl_3$ (aluminum chloride) (Sycheva et al, Ref. 28). Hydrolysis of the methyl ester 2 affords a potassium salt 3 which is coupled with monobenzoylated piperazine derivatives 4 in the presence of DEPBT (3-(diethoxyphosphoryloxy)-1,2,3-benzotriazin-4(3H)-one) and N,N-diisopropylethylamine, commonly known as Hunig's base, to provide azaindole piperazine diamide 5 (Li et al, Ref. 29). The mono-benzoylated piperazine derivatives 4 can be prepared according to well established procedures such as those described by Desai et al, Ref. 30(a), Adamczyk et al, Ref. 30(b), Rossen et al, Ref. 30(c), and Wang et al, 30(d) and 30(e).

Scheme 4

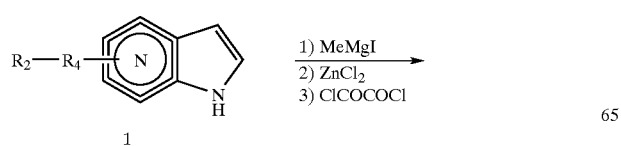

-continued

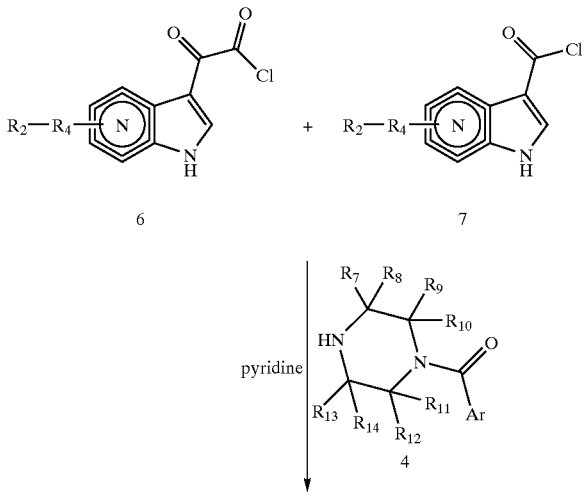

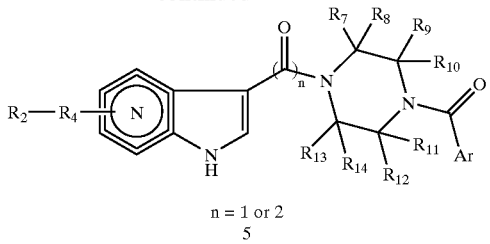

n = 1 or 2
5

An alternative method for the preparation of 5 involves treating an azaindole 1, obtained by procedures described in the literature or from commercial sources, with MeMgI and ZnCl$_2$, followed by the addition of ClCOCOCl (oxalyl chloride) in either THF (tetrahydrofuran) or ether to afford a mixture of desired products, glyoxyl chloride 6 and acyl chloride 7, Scheme 4. The resulting mixture of glyoxyl chloride 6 and acyl chloride 7 is then coupled with mono-benzoylated piperazine derivatives 4 under basic conditions to afford product 5 as a mixture of two compounds (n=1 and 2).

General routes for further functionalizing azaindole rings are shown in Schemes 5. It should be recognized that the symbol Rx is meant to represent a general depiction of the remaining substituents from R$_4$-R$_2$ which are on the azaindole ring. As depicted in Scheme 5, the azaindole can be oxidized to the corresponding N-oxide derivative 8 by using mCPBA (meta-Chloroperbenzoic Acid) in acetone or DMF (Dimethylformamide ) (eq. 1, Harada et al, Ref. 31 and Antonini et al, Ref. 32). The N-oxide 8 can be converted to a variety of substituted azaindole derivatives by using well documented reagents such as phosphorus oxychloride (POCl$_3$) (eq. 2, Schneller et al, Ref. 33(a)) or phosphorus tribromide (eq. 2, Wozniak et al, Ref. 33(b)), Grignard reagents RMgX (R=alkyl, X=Cl, Br or I) (eq. 4, Shiotani et al, Ref. 34), trimethylsilyl cyanide (TMSCN) (eq. 5, Minakata et al, Ref. 35), Ac$_2$O (eq. 6, Klemm et al, Ref. 36), thiol via a sodium thiolate or other thiolates (eq. 7, Shiotani et al, Ref. 37), alcohol via metal alkoxides as in ref 37 or (eq. 8, Hayashida et al, Ref. 38), and amine (eq. 9, using ammonia or an amine in the presence of TsCl in chloroform/water as in Miura et al, Ref. 39; or under similar conditions but with 10% aq NaOH also included as in Solekhova et al, Ref. 40). Under such conditions (respectively), a chlorine or bromine atom, nitrile group, alkyl group, hydroxyl group, thiol group, alkoxy group and amino group can be introduced to the pyridine ring. Similarly, tetramethylamonnium fluoride (Me$_4$NF) transforms N-oxides 8 to fluoro-azaindoles (eq. 3). Further standard modification of OH group will provide alkoxy functionality as well (eq. 6).

Schem 5

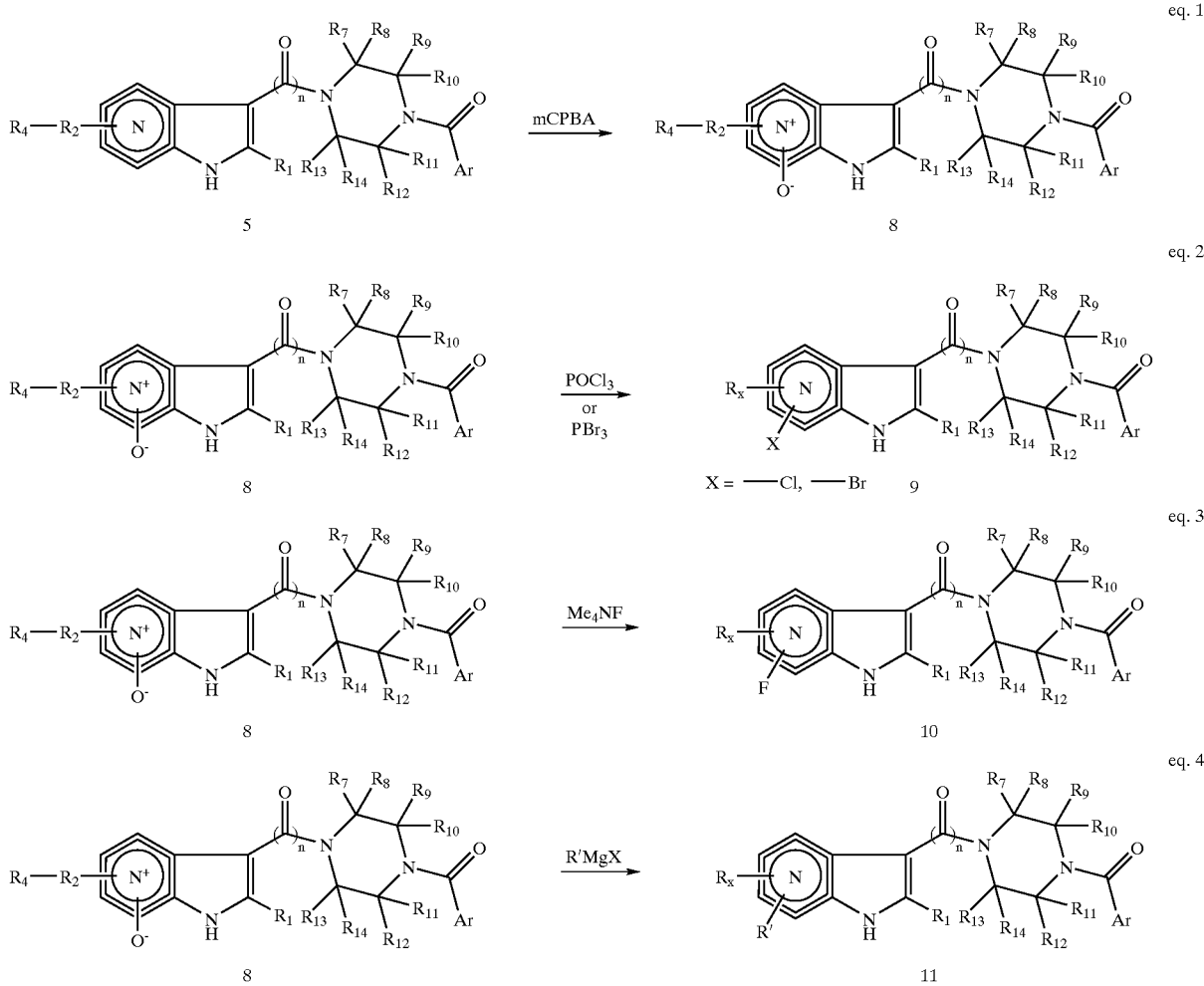

-continued
eq. 5
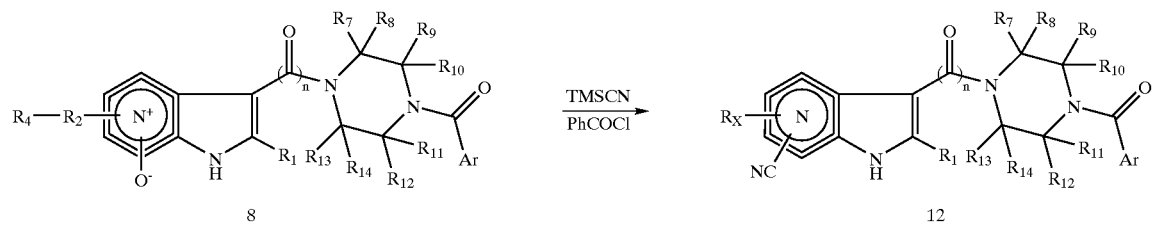
eq. 6
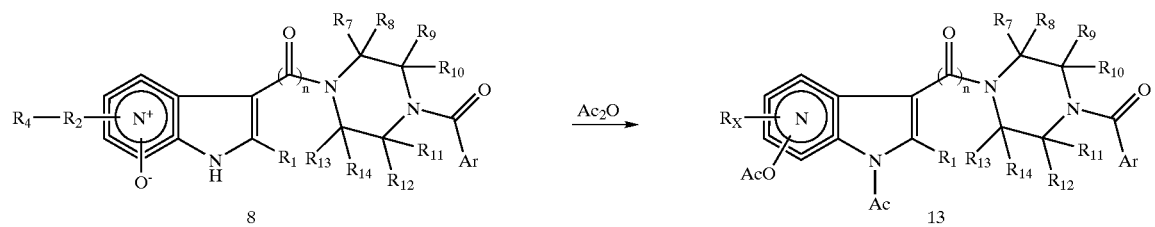
eq. 7
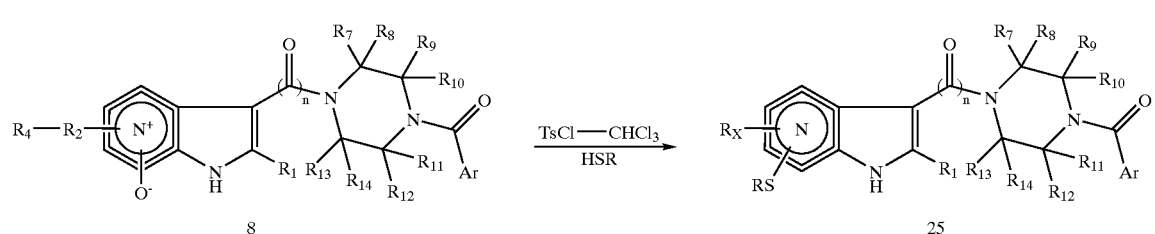
eq. 8
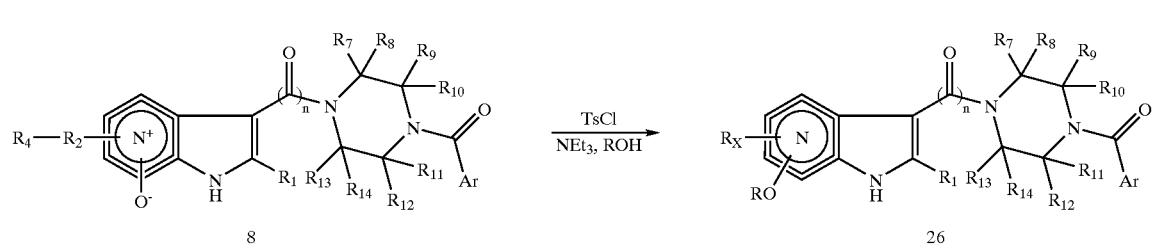
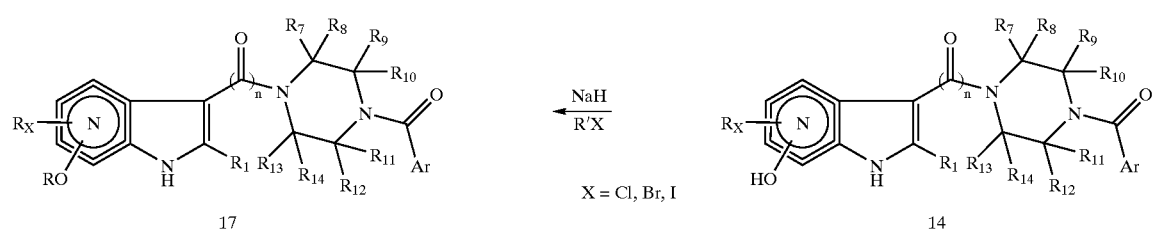

-continued eq. 9

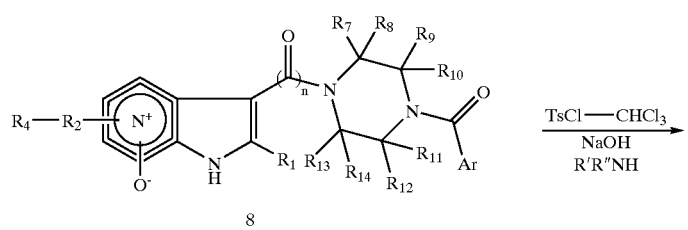

8

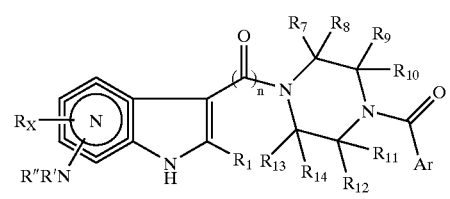

27

Nitration of azaindole N-oxides results in introduction of a nitro group to azaindole ring, as shown in Scheme 6 (eq. 10, Antonini et al, Ref. 32). The nitro group can subsequently be displaced by a variety of nucleophilic agents, such as OR, $NR^1R^2$ or SR, in a well established chemical fashion (eq. 11, Regnouf De Vains et al, Ref. 41(a), Miura et al, Ref. 41(b), Profft et al, Ref. 41(c)). The resulting N-oxides 16 are readily reduced to the corresponding azaindole 17 using phosphorus trichloride ($PCl_3$) (eq. 12, Antonini et al, Ref. 32 and Nesi et al, Ref. 42) or other reducing agents. Similarly, nitro-substituted N-oxide 15 can be reduced to the azaindole 18 using phosphorus trichloride (eq. 13). The nitro group of compound 18 can be reduced to either a hydroxylamine (NHOH) (eq. 14, Walser et al, Ref. 43(a) and Barker et al, Ref. 43(b)) or an amino ($NH_2$) group (eq. 15, Nesi et al, Ref. 42 and Ayyangar et al, Ref. 44) by carefully selecting different reducing conditions.

Scheme 6 eq. 10

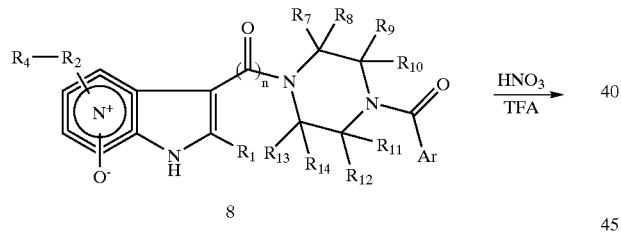

8

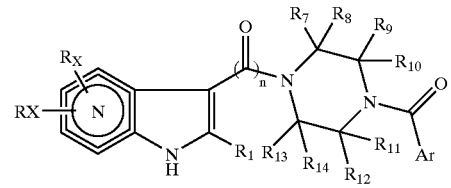

17

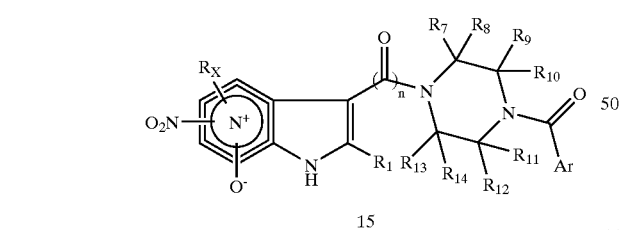

15 eq. 11

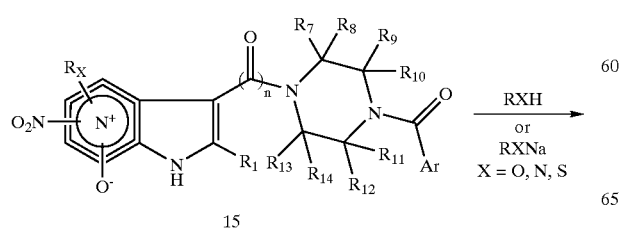

15

-continued

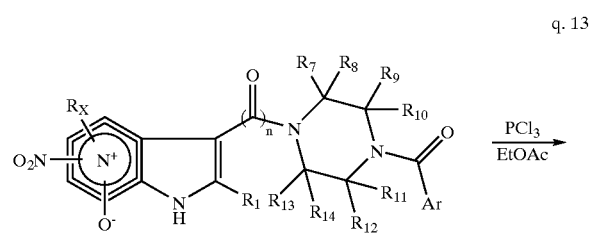

16 eq. 12

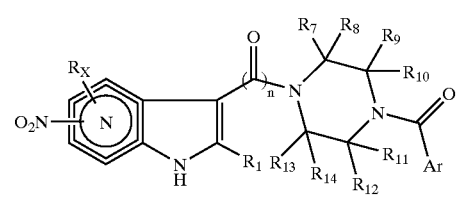

15 q. 13

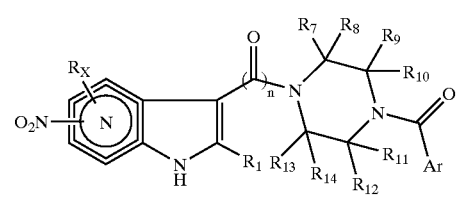

18 eq. 14

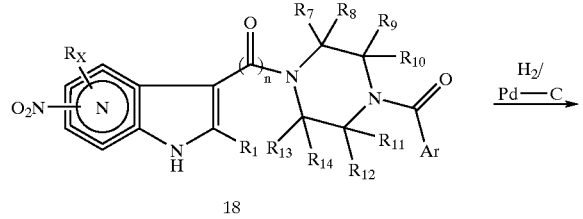

18

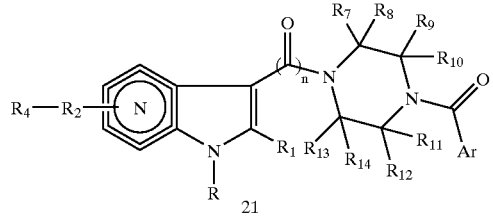

21

Halides can be converted to a variety of functionalities such as a nitrile (eq. 17), an amino group (eq. 18), and or an alkoxy group (eq. 19) (Scheme 8) using well established procedures. Examples of these types of transformations as depicted in eq.17 are shown in Sakamoto et al (Ref. 46 (a)) in which a copper cyanide is used to form a nitrile from a halide, Halley et al (Ref. 46 (b)) which provides nitriles via copper I cyanide in DMF, Yamaguchi et al (Ref. 46 (c)), Funhoff et al (Ref. 46 (d)) uses CuCN in NMP, Shiotani et al (Ref. 37). Typically the reaction of CuCN to displace a halide requires heating. Temperatures such as 145° C. for 18 h have been found to be preferred but these conditions may be varied. The temperature may be raised or lowered by up to 100° C. and reaction times may vary from as little 30 minutes to as long as 80 h depending on reaction temperature and substrate. As an alternative to Eq. 17, Klimesova et al uses a primary amide precursor (which can come from the carboxylic acid as described elsewhere) and phosphorus oxy chloride to generate a nitrile (Ref. 47) and Katritzky et al (Ref.48). As shown in eq 18 halides can be displaced with amines or ammonia. Some example conditions are contained in Shiotani et. al. reference 37 and in Katritzky et.al. reference 48. For example heating the halide 9 in an excess of a primary or secondary amine as solvent at a temperature of reflux (or between 20° C. and 200° C.) will result in displacement of the halide to provide amines 27. In the instance of ammonia or volatile amines, a pressure reactor as described in in Katritzky et.al. reference 48 can be utilized to carry out the reaction without losing the volatile amine during heating. The reactions may be monitored by TLC or or liquid chromatography and the reaction temperature increased until reaction is observed. Cosolvents such as dioxane or pyridine may be utilized when the amine is costly. An alternative method would employ the modified palidium catalysis methods of Hartwig (Yale) or Buchwald (MIT) to effect displacement under milder conditions. As shown in eq. 19 of Scheme 8, alkoxides may be used to displace halogens in 9 and provide ethers 26. Typically this transformation is best carried out by adding sodium to a solution of the parent alcohol to generate an alkanoate. Alternatively a strong base such as NaH, or $NaN(SiMe_3)_2$ may be employed. The corresponding lithium or potassium bases or metals may also be utilized. Usually, an excess of base with respect to the halide to be displaced is employed. Between two and twenty equivalents of alkanoate are usually used with ten being preferred. The reaction is carried out at reflux or a temperature of between 30° C. and 200° C. Typically approximately 80° C. is useful. The reaction may take from four to eighty hours to reach completion with times between 12 and 48 hours being typical. As described above for eq.18, the reaction progress may be monitored. Typical conditions for displacement with sodium methoxide in methanol are provided in Shiotani et.al. reference 37 in the general procedure used for the preparation of examples 5a,5c, and 6 of the reference.

eq. 15

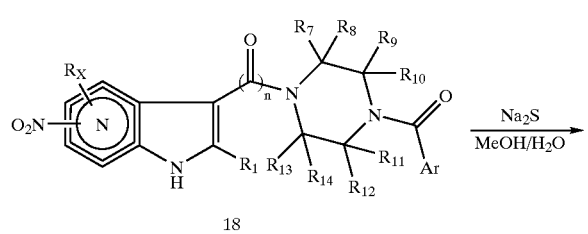

18

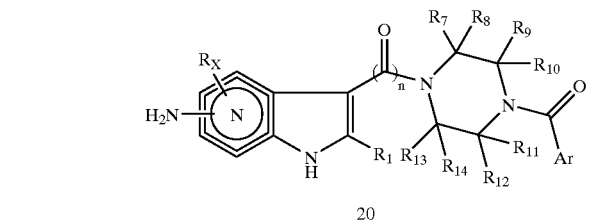

20

The alkylation of the nitrogen atom at position 1 of the azaindole derivatives can be achieved using NaH as the base, DMF as the solvent and an alkyl halide or sulfonate as alkylating agent, according to a procedure described in the literature (Mahadevan et al, Ref. 45) (eq. 16, Scheme 7).

Scheme 7 eq. 16

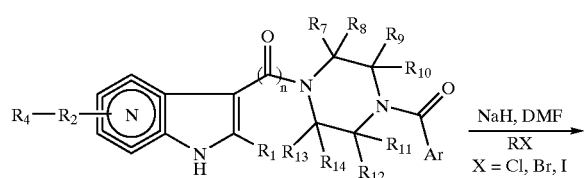

5

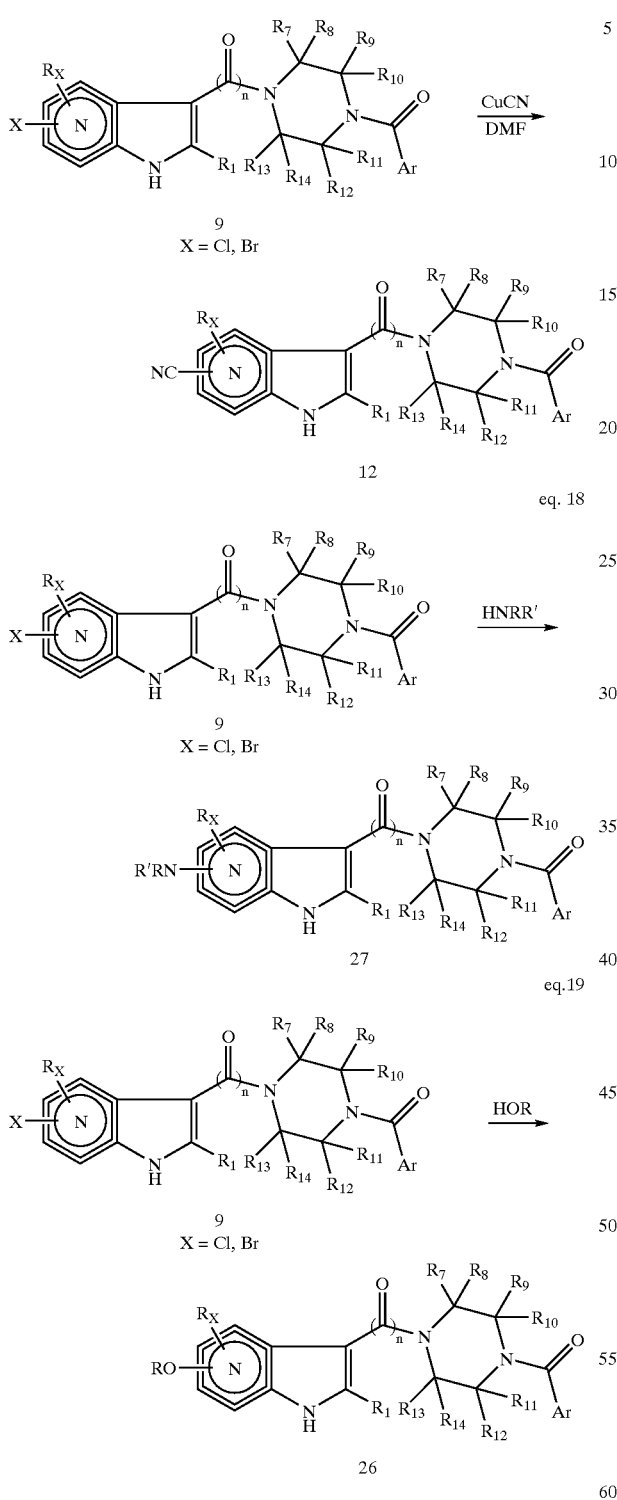

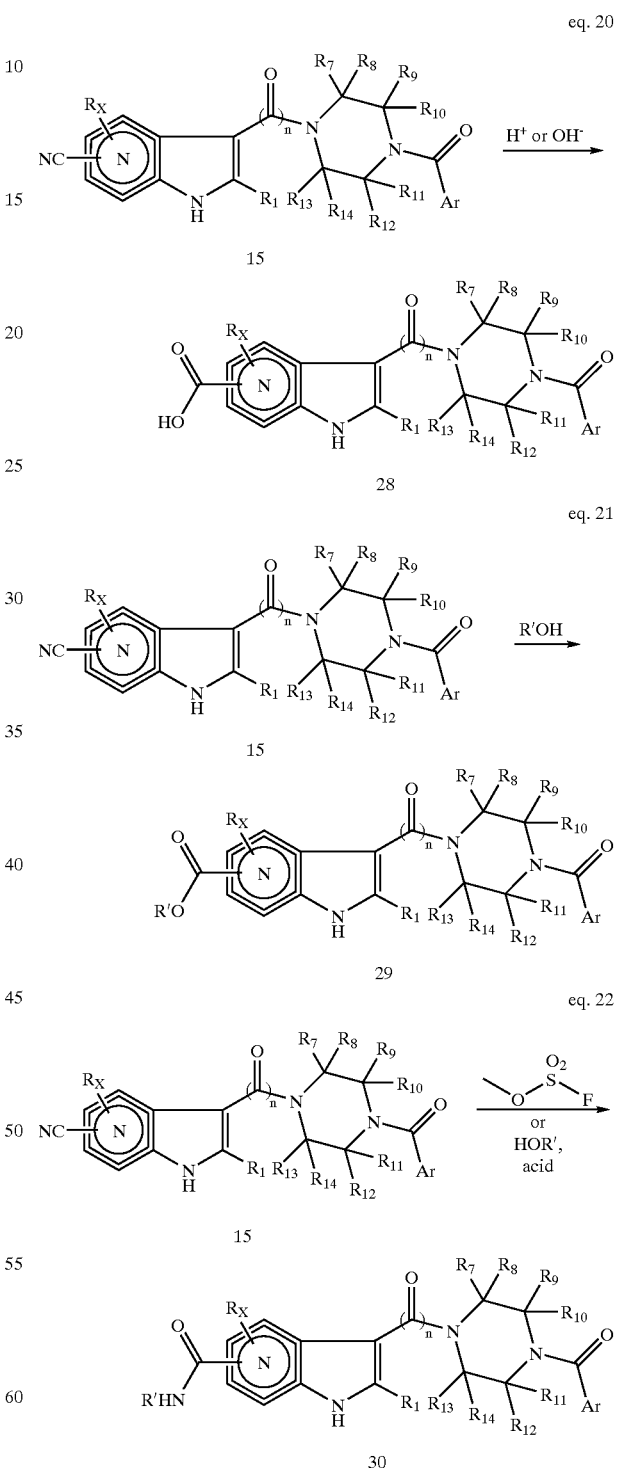

as in Norrby et al, Ref. 50 (b)). The nitrile group can be converted to an amide 30 (eq. 22, using sulfuric acid as in Sitsun'Van et al, Ref. 51 (a); or using acetic acid, tertbutanol, sulfuric acid, and acetonitrile as in Reich et al, 51 (b); or using $MeOS(O)_2F$ as in Salfetnikova et al, 51 (c)).

The nitrile group can be converted to a carboxylic acid 28 (eq. 20, using aqueous sodium hydroxide in ethanol as in Miletin et al, Ref. 49 (a); or using KOH in aqueous ethanol as in Shiotani et al, Ref. 49 (b); or using 6N HCl as in El Hadri et al, Ref 49 (c)). The nitrile group can be converted to an ester 29 (eq. 21, using sodium methoxide in methanol as in Heirtzler et al, Ref 50 (a); or using HCl in methanol In Scheme 10, the methyl group on the pyridine ring can be also oxidized to a carboxylic acid 28 using $K_2Cr_2O_7$ in 98% sulfuric acid as in (eq. 23, Oki et al, Ref. 52 (a); or using Chromium trioxide in conc sulfuric acid as in Garelli et al, Ref. 52 (b); or using selenium dioxide in pyridine as in Koyama et al, Ref. 52 (c)). The carboxylic acid may be transformed to an ester 29 using HCl in 10% methanol as in (eq. 24, Yasuda et al, Ref. 53 (a); or using thionyl chloride followed by a sodium alkyl alkoxide as in Levine et al, 53 (b); or using an alcohol and PyBOP in NMM, DMAP, and DMF as in Hoemann, 53 (c)). ). The carboxylic acid may be transformed to an amide 30 using aqueous KOH followed by oxalyl chloride in benzene followed by triethylamine in dichloromethane as in (eq. 25, Norman et al, Ref. 54 (a); or by heating an amine with the acid as in Jursic et al, 54 (b); or by coupling an amine to the acid with N,N-carbonyldiimidazole Strekowski et al, 54 (c); or by using oxalyl chloride in diethylether and an amine as in Shi et al, 54 (d)).

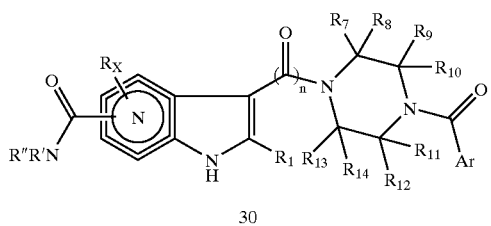

An alternative strategy for the synthesis of compounds containing varied substituents Ar is shown in Scheme 11. The benzamide moiety of the diamide 5 can be selectively hydrolyzed using to give intermediate 31. Coupling of amine 31 with with other carboxylic acids under DEBPT and base using conditions described above for earlier couplings, provides other novel diamides 5.

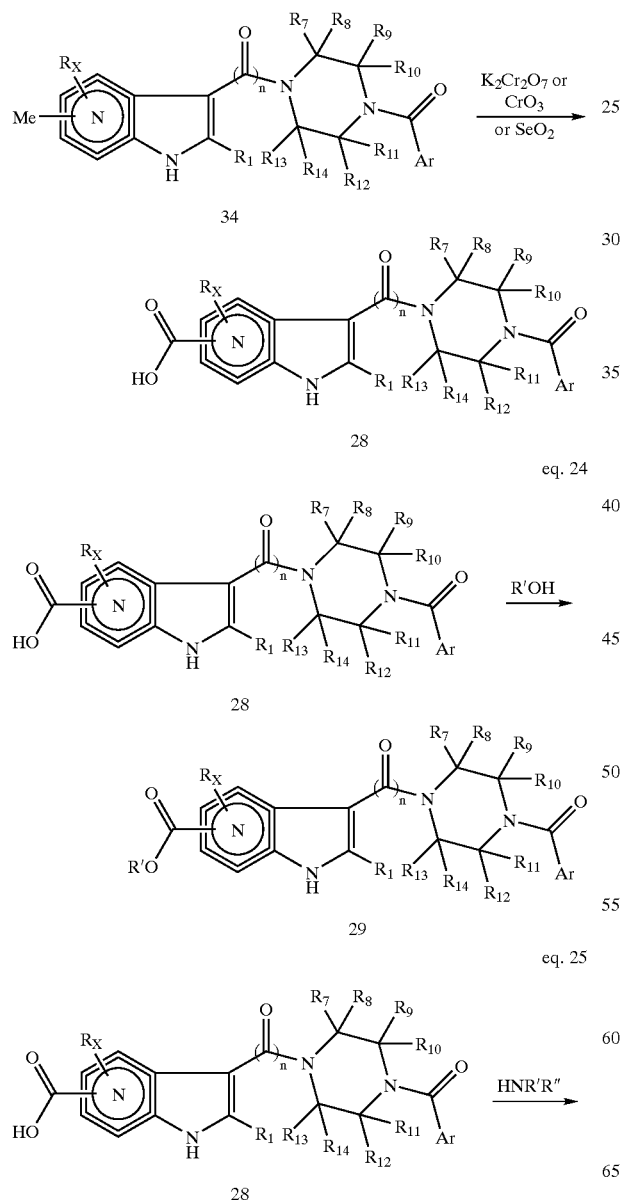

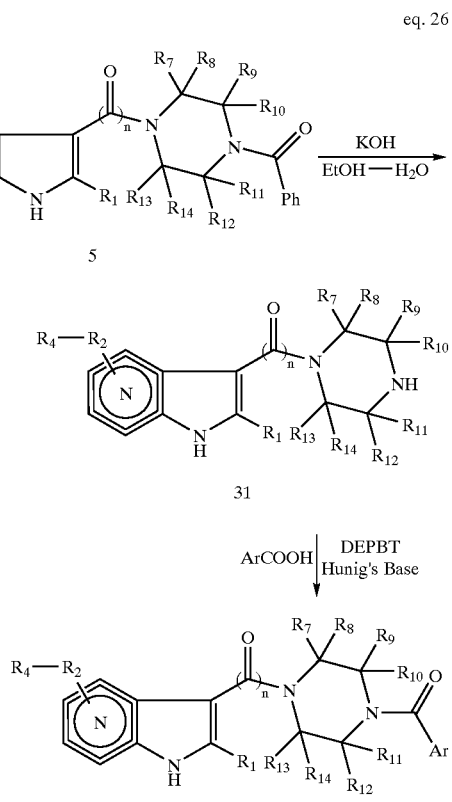

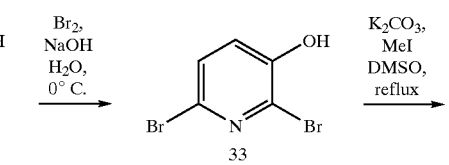

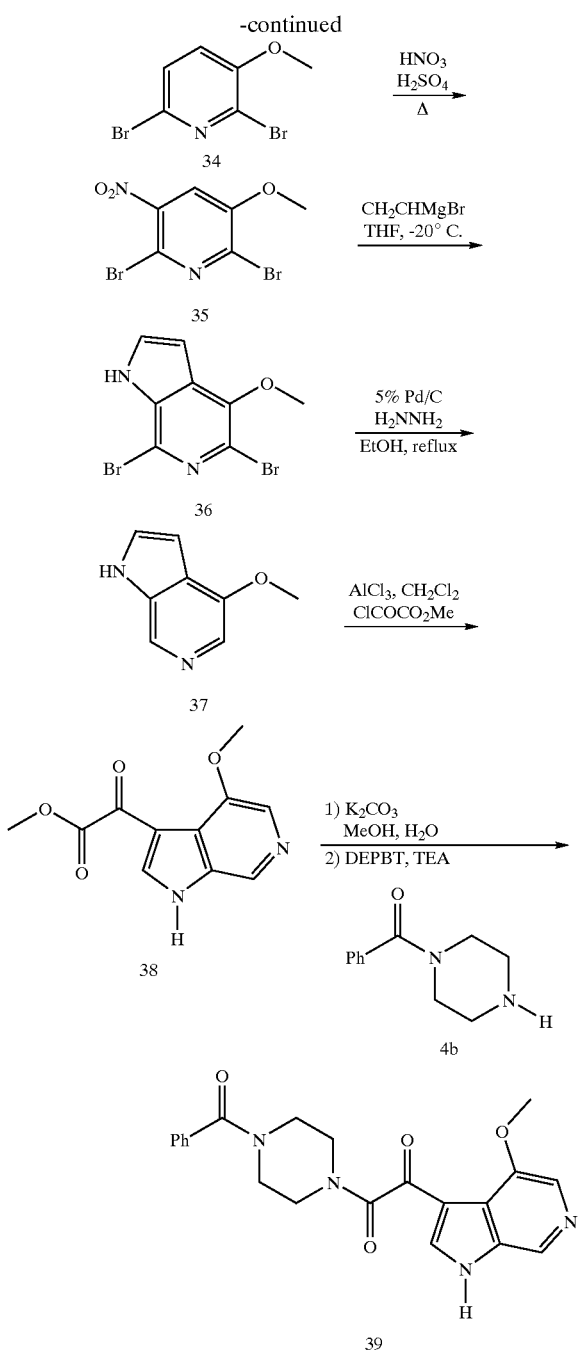

for preparing compound 39 and other compounds of formula I, an alternative route which is depicted in Scheme 13 was developed for preparing such compounds. Pyrrole 40 was prepared via the method described in Anderson, H. J., reference 57; Hydrolysis of ester 40 using standard conditions such as potassium hydroxide in ethanol at ambient temperature for ~2 h or until completion provided potassium 2-pyrrolecarboxaldehyde-4-oxoacetate. A solution of this carboxylate salt, N-benzoylpiperazine hydrochloride, 3-(diethoxyphosphoryloxy)-1,2,3-benzotriazin-4(3H)-one and triethylamine in DMF was stirred for approximately one day or until completion to provide after workup and crystallization amide 41. Amide/aldehyde 41 was stirred as a slurry in EtOH for a short time of from 1 to 60 min., cooled to 0° C. (or between −15 and 20°) and then was stirred with glycine methyl ester hydrochloride, triethylamine (or alternatively Hunig's base, 2,6-Lutidine, or no base), and sodium cyanoborohydride to provide amine 42. This transformation could also be carried out using aldehyde 41, glycine methyl ester hydrochloride, and sodium triacetoxy borohydride in either dichloromethane, tetrahydrofuran, or $C_1$–$C_4$ alcohol solvents. Alternatively, the free base of glycine methyl ester could be substituted in either procedure and a dehydrating agent such as molecular sieves could be employed in the reaction prior to addition of the borohydride reducing agent. Alternatively this transformation could be carried out by first protecting the pyrrole nitrogen with a benzoyl (from benzoyl chloride and tertiary amine) or benzyl moiety (benzyl bromide, NaH or DBU in THF). The protecting groups can be removed when desired using hydrolysis with aqueous base or hydrogenation respectively. The methyl ester 42 was hydrolyzed using potassium carbonate in methanol to provide after acidification with HCl the corresponding carboxylic acid. The acid was placed in anhydrous methanesulfonic acid containing phosphorus pentoxide which had been preheated for between 15 and 40 minutes and heated at approximately 110° (usually between 90 and 150°) for a short time of approximately 15 minutes but usually less than an hour and then poured over ice. Acylation or benzoylation of the product using for example modified Schotten-Bauman conditions (dichloromethane, potassium carbonate, and benzoyl chloride) provided ketone 43. Reaction with dimethoxy propane and anhydrous p-toluenesulfonic acid generates an intermediate enol ether which upon reaction with chloranil provided compound 39. The enol ether can alteratively be prepared using trimethyl ortho acetate and a sulfonic acid catalyst. Azaindoles such as 39 can be functionalized into nitriles which are versatile intermediates by oxidation to the N-oxide followed by reaction with DEPC and TEA or phosphorus oxychloride followed by CuCN in DMF. Details for reactions which convert 41 into 43–45 using these conditions on a similar substrate are described in reference 58 which is Suzuki, H.; Iwata, C.; Sakurai, K.; Tokumoto, K.; Takahashi, H.; Hanada, M.; Yokoyama, Y.; Murakami, Y., Tetrahedron, 1997, 53(5), 1593–1606. It should be apparent that in Schemes 12 and 13, 4b may be replaced with any of the substrates represented by formula 4 in Scheme 4. It should also be apparent that indole 37,39, 44, and 45 may be elaborated using appropriate chemistry described in the Schemes 5–11 herein which describe general methodology for functionalization of the azaindoles.

The preparation of compound 35 shown in Scheme 12 was carried out from commercially available 32 as described in Clark, G. J., Reference 56. The Bartoli methodology described in Scheme 1 was used to prepare 4-methoxy-6-azaindole 36. Reduction of the bromides using transfer hydrogenation provided the desired 4-methoxy indole 37. Compound 36 could be converted into a separable mixture of monobromides via selective lithium bromine exchange using t-Buli at cold temperatures of between −100 to −78° followed by a quench with ammonium chloride. The alternate methodology described in Scheme 3 for acylation with chloro methyl oxalate at the 3-position was applied to 37 as shown and provided intermediate 38. The methodology of Scheme 3 could then be followed to provide compound 39. While the methodology in Scheme 12 is the preferred route Scheme 13

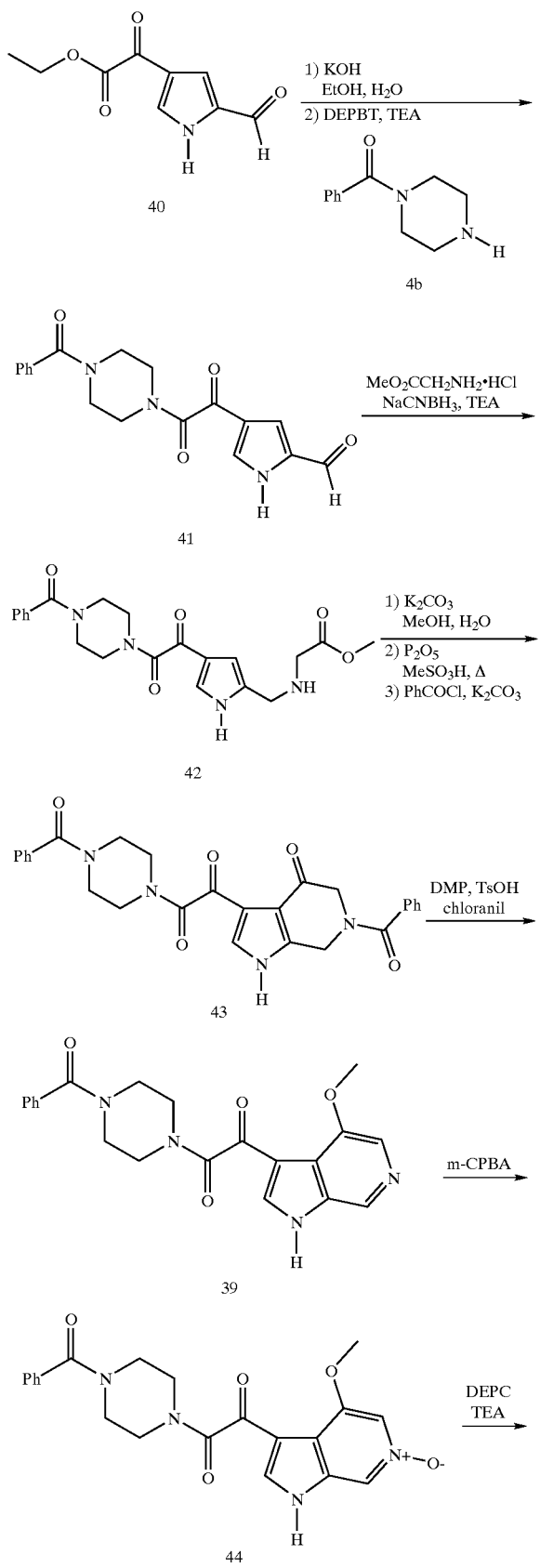

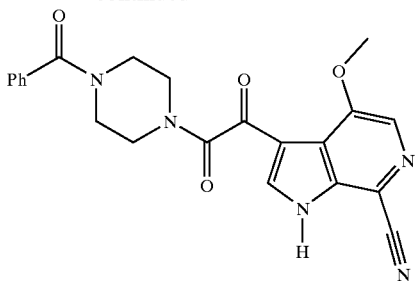

DEPBT = 3-(diethoxyphosphoryloxy)-1,2,3,-benzotriazin-4(3H)-one
DMP = 2,2-dimethoxypropane
DEPC = diethyl cyanophosphonate It should be noted that 2-chloro-5-fluoro-3-nitro pyridine may be prepared by the method in example 5B of reference 59 Marfat et.al. The chemistry in Schemes 1 and 3 to provide the derivative which corresponds to general formula 5 and has a 6-aza ring and $R_2$=F and $R_4$=Cl. In particular, reaction of 2-chloro-5-fluoro-3-nitro pyridine with 3 equivalents of vinyl Magnesium bromide using the typical conditions described herein will provide 4-fluoro-7-chloro-6-azaindole in high yield. Addition of this compound to a solution of aluminum trichloride in dichlorometane stirring at ambident temperature followed 30 minutes later with chloromethyl or chloroethyl oxalate provides an ester. Hydrolysis with KOH as in the standard procedures herein provides an acid salt which reacts with piperazines 4 (for example 1-benzoyl piperazine) in the presence of DEPBT under the standard conditions described herein to provide the compound 5 described just above. The compound with the benzoyl piperazine is N-(benzoyl)-N'-[(4-fluoro-7-chloro-6-azaindol-3-yl)-oxoacetyl]-piperazine and is compound 5av. The 7-chloro moiety in 5av can be utilized by the methods of this invention to provide the desired derivatives where $R_4$ is substituted according to the general claim. For example, exposure of 5av to sodium methoxide in refluxing methanol will provide the compound 5ay in which the 6-azaindole ring contains a 4-fluoro- and 7-methoxy substituent. Alternatively, the 4-fluoro-7-chloro-6-azaindole may be reacted with sodium methoxide and then carried through the sequence as above to provide N-(benzoyl)-N'-[(4-fluoro-7-methoxy-6-azaindol-3-yl)-oxoacetyl]-piperazine, 5ay. 4-fluoro-7-chloro-6-azaindole can also be reacted with CuCN/DMF as described in eq.17 to provide a 7-cyano intermediate which can be hydrolyzed to an acid as described in eq.21 Scheme 9 using HCl in MeOH at RT for 12 h followed by reflux to complete the reaction. The acid can be smoothly converted to to a methly ester by adding diazomethane in ether to a stitting solution of the acid in diazometane at ambient temperature or lower. These are the standard conditions for using diazomethane which is conveniently generated as a solution in diethyl ether from Diazald® based on instructions which come with a kit from Aldrich Chemical Co. The methyl ester may be carried through the acylation using oxalyl chloride as shown in Scheme 4, followed by coupling with a piperazine (benzoyl piperazine for example) to generate the corresponding 4-fluoro-7-carbomethoxy-6-azaindole which upon addition to a solution of methylamine in water would provide 5az which is N-(benzoyl)-N'-[(4-fluoro-7-(N-methylcarboxamido)-6-azaindol-3-yl)-oxoacetyl]-piperazine. The same sequences of chemistry described above for 4-fluoro-7-chloroindole may be carried out using 7-chloro-4azaindole and (R)-3-methyl-N-benzoylpiperazine 4a to provide 5abc which is (R)-N-(benzoyl)-3-methyl-N'-[(7-methoxy-4-azaindol-3-yl)-oxoacetyl]-piperazine or 5abd which is (R)-N-(benzoyl)-3-methyl-N'-[(7-(N-methyl-carboxamido)-4-azaindol-3-yl)-oxoacetyl]-piperazine. The starting 7-chloro-4-aza-indole is compound 1I and its prepartion is described as in example in the experimental section.

It should be clear that in addition to compounds 5a–5abd compounds 8, 11–30, 39, 44, and 45 are all compounds of formula I and are within the scope of the invention.

Detailed descriptions of many of the preparations of piperazine analogs of compounds of this invention and conditions for carrying out the general reactions described herein are described in PCT WO 00/76521 published Dec. 21, 2000.

In the general routes for substituting the azaindole ring described above, each process can be applied repeatedly and combinations of these processes are permissible in order to provide azaindoles incorporating multiple substituents. The application of such processes provides additional compounds of Formula I.

Antiviral Activity

The antiviral activity of compounds was determined in HeLa CD4 CCR5 cells infected by single-round infectious HIV-1 reporter virus in the presence of compound at concentrations $\leq 10$ μM. The virus infection was quantified 3 days after infection by measuring luciferase expression from integrated viral DNA in the infected cells (Chen et al, Ref. 55). The percent inhibition for each compound was calculated by quantifying the level of luciferase expression in cells infected in the presence of each compound as a percentage of that observed for cells infected in the absence of compound and subtracting such a determined value from 100. Compounds exhibiting anti-viral activity without appreciable toxicity at concentrations $\leq 10$ μM are presented in Table I.

TABLE I

| Compd # | n | $R_{7-14}$ | Average % inhibition at or <10 μM |
|---|---|---|---|
| 5a | 2 | $R_{7-13}$ = H, $R_{14}$ = (R)—Me | >99% |
| 5b | 2 | $R_{7-8}$ = $R_{10-14}$ = H, $R_9$ = Et | 90% |
| 5c | 1 | $R_{7-8}$ = $R_{10-14}$ = H, $R_9$ = Et | 80% |
| 5d | 2 | $R_{7-14}$ = H | 98% |
| 5e | 2 | $R_{7-8}$ = $R_{10-14}$ = H, $R_9$ = Me | 80% |
| 5f | 2 | $R_{7-13}$ = H, $R_{14}$ = (S)—Me | 80% |
| 5g | 2 | $R_{7-13}$ = H, $R_{14}$ = Et | 70% |
| 5h | 2 | $R_{7-12}$ = H, $R_{13}$ = $R_{14}$ = Me | 80% |
| 5i | 2 | $R_{7-8}$ = $R_{10-13}$ = H, $R_9$ = $R_{14}$ = Me | 89% |

TABLE I-continued

| Compound # | R | $R_{14}$ | Average % inhibition at or <10 μM |
|---|---|---|---|
| 5j | H | H | 90% |
| 5k | H | (R)—Me | >99% |
| 5l | H | (R)—Me | >99% |
| 5n | H | (R)—Me | 93% |

| Compound # | Ave. % inhibition at or <10 μM |
|---|---|
| 5m | 60% |

TABLE I-continued

| Compound # | R$_2$ | Average % inhibition at or <10 μM |
|---|---|---|
| 8a | H | 90% |
| 15a | NO$_2$ | 70% |
| 16a | OMe | >99% |
| 16d | OEt | 88% |
| 16e | SPr | 50% |

| Comp # | R$_2$ | R$_4$ | R$_{14}$ | Average % inhibition at or <10 μM |
|---|---|---|---|---|
| 9a | Cl | H | (R)—Me | >99% |
| 9b | H | Cl | (R)—Me | >99% |
| 10a | NO$_2$ | F | (R)—Me | >99% |
| 11a | H (when R$_4$ = Me), Me (when R$_4$ = H) | Me (when R$_2$ = H), H (when R$_2$ = Me) | (R)—Me | 99% |
| 11b | H (when R$_4$ = Ph), Ph (when R$_4$ = H) | Ph (when R$_2$ = H), H (when R$_2$ = Ph) | (R)—Me | 85% |
| 11c | H (when R$_4$ = vinyl), Vinyl (when R$_4$ = H) | Vinyl (when R$_2$ = H), H (when R$_2$ = Vinyl) | (R)—Me | 48% |
| 12a | H | CN | (R)—Me | >99% |
| 14a | H | OH | (R)—Me | >99% |
| 17a | OMe | H | (R)—Me | >99% |
| 17d | OMe | H | (S)—Me | 98% |
| 17e | OMe | H | Me | 94% |
| 17b | OCH$_2$CF$_3$ | H | (R)—Me | 99% |
| 17c | O-i-Pr | H | (R)—Me | >99% |
| 18a | NO$_2$ | H | (R)—Me | 80% |
| 19a | NHOH | H | (R)—Me | 98% |
| 20a | NH$_2$ | H | (R)—Me | 95% |
| 17f | H | PrS | (R)—Me | >99% |

| Compound # | Average % inhibition at or <10 μM |
|---|---|
| 13a | >99% |

| Compound # | R | Average % inhibition at or <10 μM |
|---|---|---|
| 21a | Me | 70% |
| 21b | —CH2—CH=CH2 | 95% |

| Compound # | R | R$_{14}$ | Average % inhibition at or <10 μm |
|---|---|---|---|
| 5p | H | H | 40% |
| 5r | H | (R)—Me | >99% |
| 5s | H | (S)—Me | 56% |

TABLE I-continued

| | | | |
|---|---|---|---|
| 5q | H | Me | 97% |
| 5t | Cl | H | >99% |
| 5u | Cl | (R)—Me | 99% |
| 5v | OMe | (R)—Me | >99% |
| 27c | NMe$_2$ | (R)—Me | 63% |

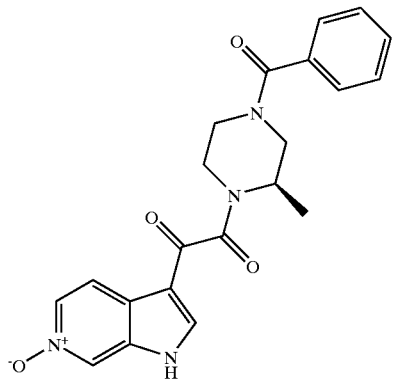

| Compound # | Average % inhibition at or <10 μm |
|---|---|
| 8b | 91% |

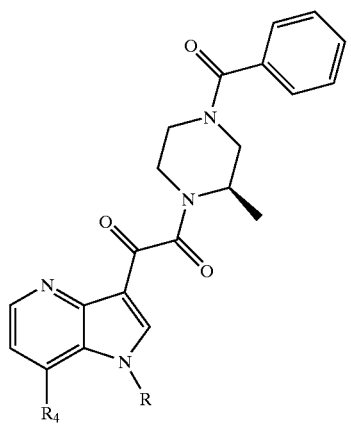

| Compound # | R$_4$ | R | Average % inhibition at or <10 μm |
|---|---|---|---|
| 5w | H | H | 98% |
| 5x | Me | H | 99% |
| 5y | Cl | H | >99% |
| 5z | OMe | Me | 97% |

Experimental Procedures

Biology

In Table I and hereafter, the following definitions apply.

"μM" means micromolar;

"ml" or "mL" means milliliter;

"μl" means microliter;

"mg" means milligram;

"nM" means nanomolar

"a" refers to percent inhibition data as representing the mean values of at least two experiments with duplicate determinations in each experiment.

The materials and experimental procedures used to obtain the results reported in Table I are described below.

Cells:

Virus production—Human embryonic Kidney cell line, 293, propagated in Dulbecco's Modified Eagle Medium (Life Technologies, Gaithersburg, Md.) containing 10% fetal Bovine serum (FBS, Sigma, St. Louis, Mo.).

Virus infection—Human epithelial cell line, HeLa, expressing the HIV-1 receptors CD4 and CCR5 was propagated in Dulbecco's Modified Eagle Medium (Life Technologies, Gaithersburg, Md.) containing 10% fetal Bovine serum (FBS, Sigma, St. Louis, Mo.) and supplemented with 0.2 mg/ml Geneticin (Life Technologies, Gaithersburg, Md.) and 0.4 mg/ml Zeocin (Invitrogen, Carlsbad, Calif.).

Virus—Single-round infectious reporter virus was produced by co-transfecting human embryonic Kidney 293 cells with an HIV-1 envelope DNA expression vector and a proviral cDNA containing an envelope deletion mutation and the luciferase reporter gene inserted in place of HIV-1 nef sequences (Chen et al, Ref. 55). Transfections were performed using lipofectAMINE PLUS reagent as described by the manufacturer (Life Technologies, Gaithersburg, Md.).

Experiment

1. Compound was added to HeLa CD4 CCR5 cells plated in 96 well plates at a cell density of 5×10$^4$ cells per well in 100 μl Dulbecco's Modified Eagle Medium containing 10% fetal Bovine serum at a concentration of <20 μM.
2. 100 μl of single-round infectious reporter virus in Dulbecco's Modified Eagle Medium was then added to the plated cells and compound at an approximate multiplicity of infection (MOI) of 0.01, resulting in a final volume of 200 μl per well and a final compound concentration of <10 μM.
3. Samples were harvested 72 hours after infection.
4. Viral infection was monitored by measuring luciferase expression from viral DNA in the infected cells using a luciferase reporter gene assay kit (Roche Molecular Biochemicals, Indianapolis, Ind.). Infected cell supernatants were removed and 50 μl of Dulbecco's Modified Eagle Medium (without phenol red) and 50 μl of luciferase assay reagent reconstituted as described by the manufacturer (Roche Molecular Biochemicals, Indianapolis, Ind.) was added per well. Luciferase activity was then quantified by measuring luminescence using a Wallac microbeta scintillation counter.
5. The percent inhibition for each compound was calculated by quantifying the level of luciferase expression in cells infected in the presence of each compound as a percentage of that observed for cells infected in the absence of compound and subtracting such a determined value from 100.

Method for Extrapolating % Inhibition at 10 μM

The data in Table 1 was obtained using the general procedures above and by the following methods. Data is not reported for all compounds since data for all the compounds is reported by the alternate method in Table 2. The percent inhibition for each compound was calculated by quantifying the level of luciferase expression in cells infected in the presence of compound as a percentage of that observed for cells infected in the absence of compound and subtracting such a determined value from 100. For compounds tested at concentrations less than 10 μM, the percent inhibition at 10 μM was determined by extrapolation using the XLfit curve fitting feature of the Microsoft Excel spreadsheet software. Curves were obtained from 10 data points (% inhibition determined at 10 concentrations of compound) by using a four parameter logistic model (XLfit model 205: $y=A+((B-A)/(1+((C/x)^D)))$, where, A=minimum y, B=maximum y, C=log EC$_{50}$, D=slope factor, and x and y are known data values. Extrapolations were performed with the A and B parameters unlocked.

Biological Data Expressed as an $EC_{50}$

Table 2 presents the data for the compounds grouped based on their $EC_{50}$ which provides an additional method for comparing the antiviral potency of the compounds of this invention. These values were calculated by the following method. The effective concentration for fifty percent inhibition ($EC_{50}$) was calculated with the Microsoft Excel XLfit curve fitting software. For each compound, curves were generated from percent inhibition calculated at 10 different concentrations by using a four paramenter logistic model (model 205).

TABLE 2

Biological Data Expressed as $EC_{50}s$

| Compounds* with $EC_{50}s$ | Compounds with $EC_{50}s > 1$ $\mu M$ but $<5$ $\mu M$ | Compounds with EC50 $< 1$ $\mu M$ |
|---|---|---|
| >0.4 μM: 5ac. >0.5 μM: 5m, 5p, 5s, 5ab, 5ad, 5ae, 16b, 16c, 16h, 17f, 17g, 17h. >5 μM: 5af, 5ag, 5ah, 8e, 11c, 16e, 17g, | 5h, 11b, 18a, | 5a, 5b, 5c, 5d, 5e, 5f, 5g, 5i, 5j, 5k, 5l, 5n, 5q, 5r, 5t, 5u, 5v, 5w, 5x, 5y, 5z, 5ai, 5ak, 5an, 5ao, 5ap, 8a, 8b, 9a, 9b, 10a, 11a, 12a, 13a, 15a, 16a, 16d, 17a, 17b, 17c, 17d, 17e, 19a, 20a, 21a, 21b, 27c, 39 |

*Some of these compounds were tested at a concentration lower than their $EC_{50}$ but showed some ability to cause inhibition and thus should be evaluated at a higher concentration to determine the exact $EC_{50}$. An approximate attempt to exclude compounds which did not show some potential for inhibition (those which might have an EC50 > 100 uM) was made.

Chemistry

All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

LC/MS Method (i.e., compounds identification)

| | |
|---|---|
| Column A: | YMC ODS-A S7 3.0 × 50 mm column |
| Column B: | PHX-LUNA C18 4.6 × 30 mm Column |
| Gradient: | 100% Solvent A/0% Solvent B to 0% Solvent A/ 100% Solvent B |
| Gradient time: | 2 minutes |
| Hold time: | 1 minute |
| Flow rate: | 5 ml/min |
| Detector Wavelength: | 220 nm |
| Solvent A: | 10% MeOH/90% $H_2O$/0.1% Trifluoroacetic Acid |
| Solvent B: | 10% $H_2O$/90% MeOH/0.1% Trifluoroacetic Acid |

Compounds purified by preparative HPLC were diluted in methanol (1.2 ml) and purified using the following methods on a Shimadzu LC-10A automated preparative HPLC system.

Preparative HPLC Method (i.e., Compound Purification)

Purification Method: Initial gradient (30% B, 70% A) ramp to final gradient (100% B, 0% A) over 20 minutes, hold for 3 minutes (100% B, 0% A)

| | |
|---|---|
| Solvent A: | 10% MeOH/90% $H_2O$/0.1% Trifluoroacetic Acid |
| Solvent B: | 10% $H_2O$/90% MeOH/0.1% Trifluoroacetic Acid |
| Column: | YMC C18 S5 20 × 100 mm column |
| Detector Wavelength: | 220 nm |

TYPICAL PROCEDURES AND CHARACTERIZATION OF SELECTED EXAMPLES

Typical Procedure for the Preparation of Compounds in Scheme 1

1) Preparation of Azaindole 1

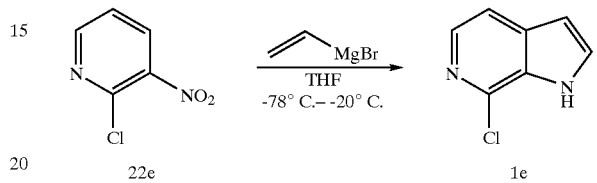

22e                                                 1e

Preparation of azaindole, Method A: Preparation of 7-Chloro-6-azaindole 1e: 2-Chloro-3-nitropyridine 22e (5.0 g) was dissolved in dry THF (200 ml). After the solution was cooled down to −78° C., an excess of vinyl magnesium bromide (1.0 M in THF, 100 ml) was added. Then, the reaction was left at −20° C. for eight hours before quenched with 20% $NH_4Cl$ (150 ml). The aqueous phase was extracted with EtOAc (3×150 ml). The combined organic layer was dried over $MgSO_4$. After filtration and concentration, the crude product was purified by silica gel column chromatography to afford 1.5 g of 7-chloro-6-azaindole 1e in 31% yield.

Summarized below is the characterization of compounds 1 with the following structures:

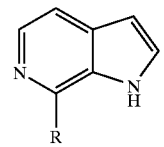

Compound 1e, R=Cl, 7-Chloro-6-azaindole: $^1$H NMR (500 MHz, $CD_3OD$) δ 7.84 (d, 1H, J=7.95 Hz), 7.76 (m, 2H), 6.61 (d, 1H, J=5.45 Hz). MS m/z: (M+H)$^+$ calcd for $C_7H_6ClN_2$: 153.02; found 152.93. HPLC retention time: 0.51 minutes (column A).

Compound 1f, R=OMe, 7-Methoxy-6-azaindole: MS m/z: (M+H)$^+$ calcd for $C_8H_9N_2O$: 149.07; found 149.00. HPLC retention time: 0.42 minutes (column A).

Characterization of compounds 1 with the following substructure prepared by the method above:

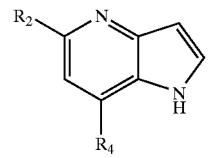

Compound 1g, $R_2$=H, $R_4$=Me, 7-Methyl-4-azaindole: MS m/z: (M+H)$^+$ calcd for $C_8H_9N_2$: 133.08; found 133.01. HPLC retention time: 0.34 minutes (column A).

Compound 1ak, $R_2$=Cl, $R_4$=Me, 5-Chloro-7-methyl-4-azaindole: MS m/z: (M+H)$^+$ calcd for $C_8H_8ClN_2$: 167.04;

found 166.99. HPLC retention time: 1.22 minutes (column B).

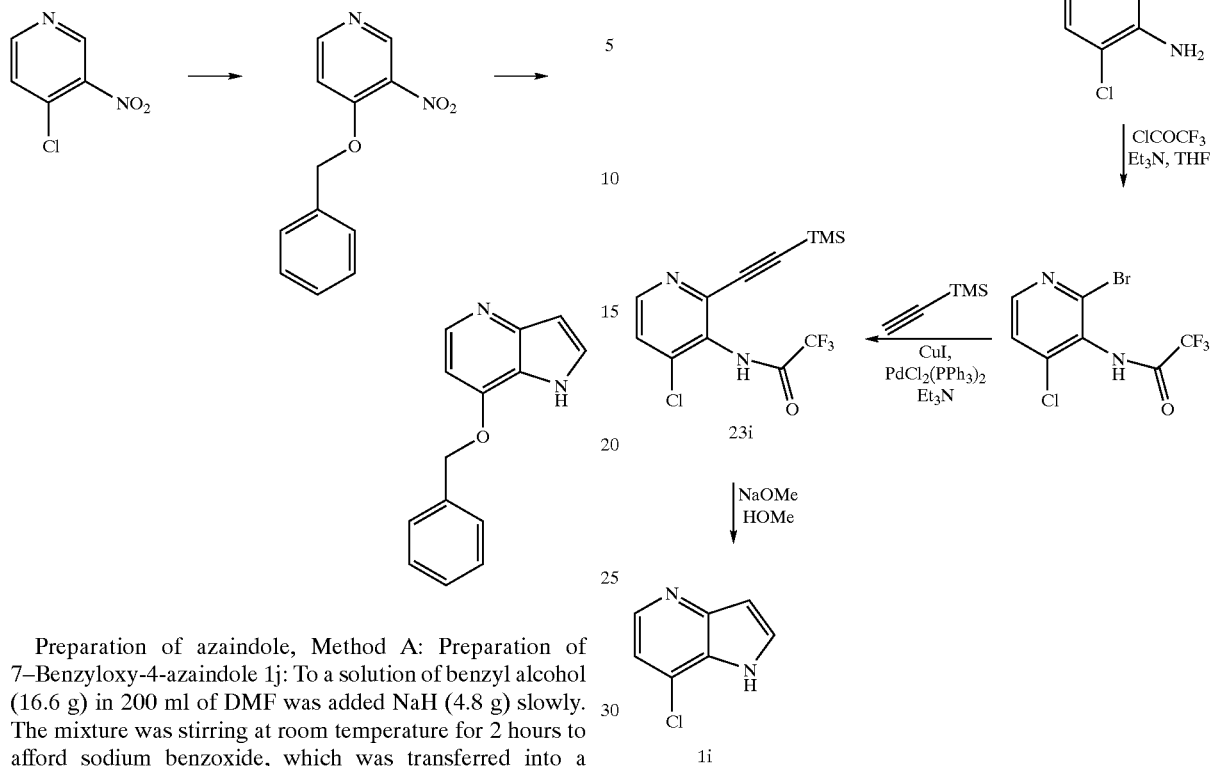

Preparation of azaindole, Method A: Preparation of 7–Benzyloxy-4-azaindole 1j: To a solution of benzyl alcohol (16.6 g) in 200 ml of DMF was added NaH (4.8 g) slowly. The mixture was stirring at room temperature for 2 hours to afford sodium benzoxide, which was transferred into a solution of 4-chloro-3-nitropyridine hydrochloride 22j (20 g) in DMF (100 ml). The resulting mixture was kept stirring for 10 hours before quenched with water. After DMF was removed under vaccum, the crude product was suspended in water and extracted with EtOAc (3×250 ml). The organic phase was dried over $MgSO_4$ and concentrated to give a residue, which was purified via recrystallization to afford 6.1 g of 4-benzoxy-3-nitropyridine 22j.

Characterization of Compound 22j:

4-benzyloxy-3-nitropyridine: MS m/z: $(M+H)^+$ calcd for $C_{12}H_{11}N_2O_3$: 231.08; found 231.06. HPLC retention time: 1.46 minutes (column A).

Preparation of compound 1j, 7-benzoxy-4-azaindole: The general procedure and conditions described for the Bartoli-type reaction used to prepare 1e were followed.

Characterization of Compound 1j:

Compound 1j, 7-benzyloxy-4-azaindole: $^1$H NMR (500 MHz, $CDCl_3$) δ 8.64 (b, 1H), 8.34 (d, 1H, J=5.35 Hz), 7.40 (m, 6H), 6.72 (d, 1H, J=3.25 Hz), 6.67 (d, 1H, J=5.45 Hz), 5.35 (s, 2H); $^{13}$C NMR (125 MHz, $CDCl_3$). δ 151.1, 147.9, 145.2, 135.8, 128.8, 128.6, 127.9, 126.3, 119.6, 103.9, 99.6, 70.2. MS m/z: $(M+H)^+$ calcd for $C_{14}H_{13}N_2O$: 225.10; found 225.03. HPLC retention time: 1.11 minutes (column A).

Preparation of azaindole, Typical example for Method B: Preparation of 7-chloro-4-azaindole 1i:

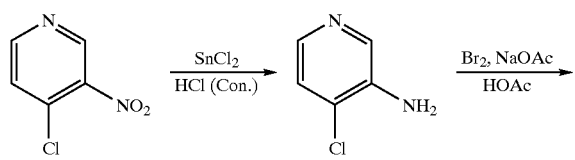

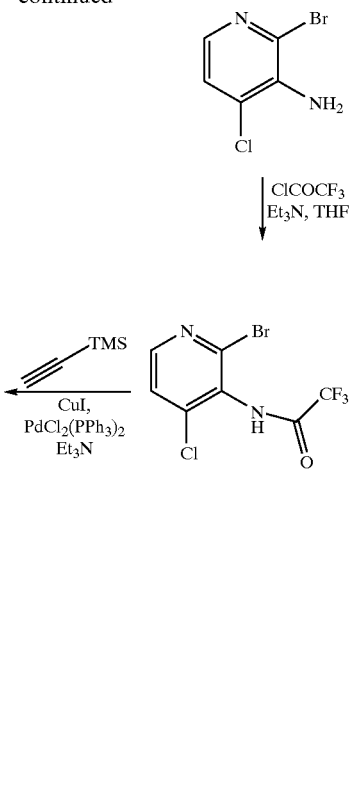

An excess of $SnCl_2$ (25 g) was cautiously added into a solution of 4-chloro-3-nitropyridine hydrochloride (5 g) in concentrated HCl and the reaction was stirred for 12 hours. Concentration under pressure provided a mixture, which was neutralized with 2N NaOH to pH 6–7. The aqueous phase was extracted with EtOAc (5×100 ml). The organic layers were then combined, dried over anhydrous $MgSO_4$ and concentrated in vacuo to give a crude product (2.2 g), which was 4-chloro-3-nitropyridine which was pure enough for direct use in further reactions.

7 g of the crude product from the previous step was dissolved in 200 ml of TFA. Then, 10.7 g of NBS was added into the mixed solution cautiously. After 8 hours, solvent was removed under vacuum. The residue was dissolved in 2N NaOH (200 ml) and aqueous layer was extracted with EtOAc (3×200 ml). The combined organic layer was dried over $MgSO_4$ and concentrated to provide a crude product with was purified via recrystallization in hexane to afford 5 g of 3-amino-2-bromo-4-chloropyridine.

Characterization of 3-amino-2-bromo-4-chloropyridine: MS m/z: $(M+H)^+$ calcd for $C_5H_5BrClN_2$: 206.93; found 206.86. HPLC retention time: 1.32 minutes (column B).

To a solution of 3-amino-2-bromo-4-chloropyridine in 250 ml of ether was added 8.4 g of trifluoroacetic anhydride at 0° C. 5.3 g of $Na_2CO_3$ was added 10 minutes later, and the reaction mixture was stirred at room temperature for 10 hours before the reaction was quenched with water (100 ml). The aqueous phase was extracted with EtOAc (3×150 ml). The combined organic layer was dried over $MgSO_4$ and concentrated to give a residue, which was purified by silica gel column chromatography to afford 3.7 g of compound 23i.

Characterization of Compound 23i:

2-Bromo-4-chloro-3-trifluoroacetaminopyridine: MS m/z: (M+H)+ calcd for $C_7H_4BrClF_3N_2O$: 302.90; found 302.91. HPLC retention time: 1.48 minutes (column B).

A mixture of compound 23i (0.9 g), trimethylsilylacetylene (0.49 g), Pd $Cl_2(PPh_3)_2$ (0.1 g) and CuI (0.05 g) in $Et_3N$ (1.5 ml) was heated to 100° C. in sealed tube for 10 hours. Then, solvent was removed under vaccum. The residue was partitioned between water (10 ml) and EtOAc (10 ml). Aqueous phase was extracted with EtOAc (2×10 ml). The combined organic layer was dried over $MaSO_4$ and concentrated under vaccum to provide a crude product 24i which was used in the further reaction without purification.

Characterization of Compound 24i:

Compound 24i, 4-Chloro-3-trifluoroacetamido-2-(trimethylsilylethynyl)pyridine: MS m/z: (M+H)+ calcd for $C_7H_4BrClF_3N_2O$: 321.04; found 320.99. HPLC retention time: 1.79 minutes (column B).

A mixture of compound 24i (0.28 g) and sodium ethoxide (0.30 ml) in 20 ml of ethanol was heated to reflux for 10 hours under nitrogen atmosphere. After solvent removed under vaccum, the residue was purified using Shimadzu automated preparative HPLC System to give compound 1i (0.1 g).

Characterization of Compound 1i:

Compound 1i, 7-Chloro-4-azaindole: $^1$H NMR (500 MHz, $CD_3OD$) δ 8.50 (d, 1H, J=6.20 Hz), 8.10 (d, 1H, J=3.20 Hz), 7.71 (d, 1H, J=6.30 Hz), 6.91 (d, 1H, J=3.25 Hz). MS m/z: (M+H)+ calcd for $C_7H_6ClN_2$: 153.02; found 152.90. HPLC retention time: 0.45 minutes (column A).

1) Preparation of Azaindole 3-Glyoxylmethyl Ester 2

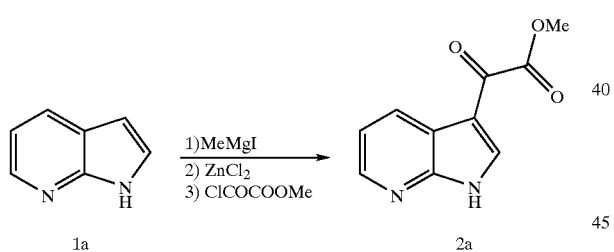

Acylation of azaindole, method A: Preparation of Methyl (7-azaindol-3-yl)-oxoacetate 2a: To a solution of 7-azaindole 1a (20.0 g, 0.169 mol) in dry $CH_2Cl_2$ (1000 ml), 62.1 ml of MeMgI (3.0M in $Et_2O$, 0.186 mol) was added at room temperature. The resulting mixture was stirred at room temperature for 1 hour before $ZnCl_2$ (27.7 g, 0.203 mol) was added. One hour later, methyl chlorooxoacetate (24.9 g, 0.203 mol) was injected into the solution dropwise. Then the reaction was stirred for 8 hours before being quenched with methanol.

After all solvents were evaporated, the residue was partitioned between ethyl acetate (500 ml) and $H_2O$ (300 ml). The aqueous phase was neutralized with saturated $Na_2CO_3$ to pH 6–6.5, and extracted with EtOAc (3×500 ml). The organic layers were then combined, washed with 0.1N HCl (3×200 ml), dried over anhydrous $MgSO_4$ and concentrated in vacuo to give a crude product 2a (14.3 g, 41.5%), which was pure enough for the further reactions.

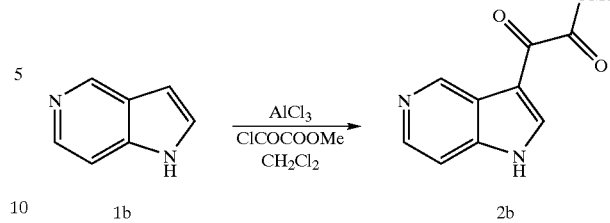

Acylation of azaindole, method B: Preparation of Methyl (5-azaindol-3-yl)-oxoacetate 2b: 5-Azaindole 1b (0.5 g, 4.2 mmol) was added to a suspension of $AlCl_3$ (2.8 g, 21.0 mmol) in $CH_2Cl_2$ (100 ml). Stirring was continued at room temperature for 1 hour before methyl chlorooxoacetate (2.5 g, 21.0 mmol) was added dropwise. The reaction was stirred for 8 hours. After 20 ml of MeOH was added cautiously to quench the reaction, solvents were removed under vaccum. The solid residue was purified by silica gel column chromatography (EtOAc/MeOH=10:1) to afford 0.6 g (70%) of the acylated product 2b.

Characterization of Compounds 2:

Compound 2a, Methyl (7-azaindol-3-yl)-oxoacetate: $^1$H NMR (300 MHz, DMSO-$d_6$) δ 8.60 (s, 1H), 8.47 (d, 1H, J=7.86 Hz), 8.40 (d, 1H, J=4.71 Hz), 7.34 (dd, 1H, J=7.86, 4.77 Hz), 3.99 (s, 3H); $^{13}$C NMR (75 MHz, DMSO-$d_6$) δ 178.7, 163.3, 149.0, 145.1, 138.8, 129.7, 119.0, 118.0, 111.2, 52.7. MS m/z: (M+H)+ calcd for $C_{10}H_9N_2O_3$: 205.06; found 205.04. HPLC retention time: 0.94 minutes (column A).

Compound 2b, Methyl (5-azaindol-3-yl)-oxoacetate: $^1$H NMR (500 MHz, $CD_3OD$) δ 9.61 (s, 1H), 9.02 (s, 1H), 8.59 (d, 1H, J=6.63 Hz), 8.15 (d, 1H, J=6.60 Hz), 4.00 (s, 3H); $^{13}$C NMR (125 MHz, $CD_3OD$) δ 178.9, 163.0, 145.6, 144.2, 138.3, 135.0, 124.7, 116.3, 112.1, 53.8. MS m/z: (M+H)+ calcd for $C_{10}H_9N_2O_3$: 205.06; found 205.04. HPLC retention time: 0.32 minutes (column A).

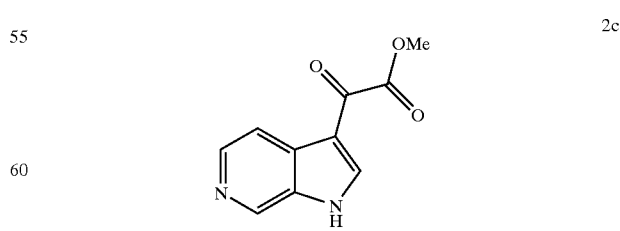

Compound 2c, Methyl (6-azaindol-3-yl)-oxoacetate: MS m/z: (M+H)+ calcd for $C_{10}H_9N_2O_3$: 205.06; found 205.14. HPLC retention time: 0.61 minutes (column A).

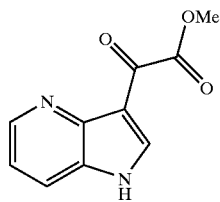

Compound 2d, Methyl (4-azaindol-3-yl)-oxoacetate: MS m/z: (M+H)+ calcd for $C_{10}H_9N_2O_3$: 205.06; found 204.99. HPLC retention time: 0.34 minutes (column A).

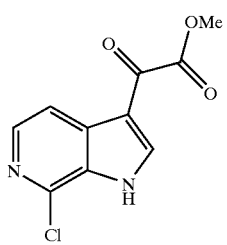

Compound 2e, Methyl (7-chloro-6-azaindol-3-yl)-oxoacetate: $^1$H NMR (500 MHz, DMSO-$d_6$) δ 8.66 (s, 1H), 8.17 (d, 1H, J=5.35 Hz), 8.05 (d, 1H, J=5.30 Hz), 3.91 (s, 3H); $^{13}$C NMR (125 MHz, DMSO-$d_6$) δ 178.4, 162.7, 141.3, 140.9, 134.6, 133.0, 130.1, 115.4, 113.0, 52.8. MS m/z: (M+H)+ calcd for $C_{10}H_8ClN_2O_3$: 239.02; found 238.97. HPLC retention time: 1.18 minutes (column A).

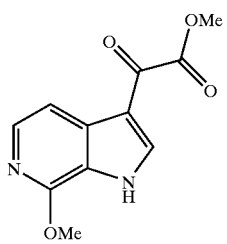

Compound 2f, Methyl (7-methoxy-6-azaindol-3-yl)-oxoacetate: MS m/z: (M+H)+ calcd for $C_{11}H_{11}N_2O_4$: 235.07; found 234.95. HPLC retention time: 0.95 minutes (column A).

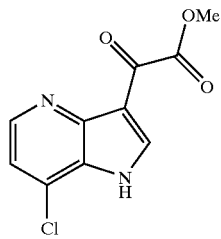

Compound 2 h, Methyl (7-chloro-4-azaindol-3-yl)-oxoacetate: MS m/z: (M+H)+ calcd for $C_{10}H_8ClN_2O_3$: 239.02; found 238.97. HPLC retention time: 0.60 minutes (column A).

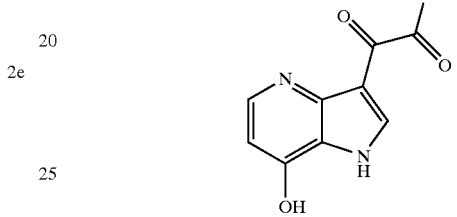

Compound 2i, Methyl (7-hydroxyl-4-azaindol-3-yl)-oxoacetate: MS m/z: (M+H)+ calcd for $C_{10}H_9N_2O_4$: 221.06; found 220.96. HPLC retention time: 0.76 minutes (column A).

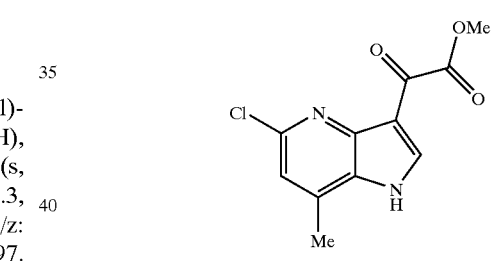

Compound 2ak, Methyl (5-chloro-7-methyl-4-azaindol-3-yl)-oxoacetate: MS m/z: (M+H)+ calcd for $C_{11}H_{10}ClN_2O_3$: 253.04; found 252.97. HPLC retention time: 1.48 minutes (column B).

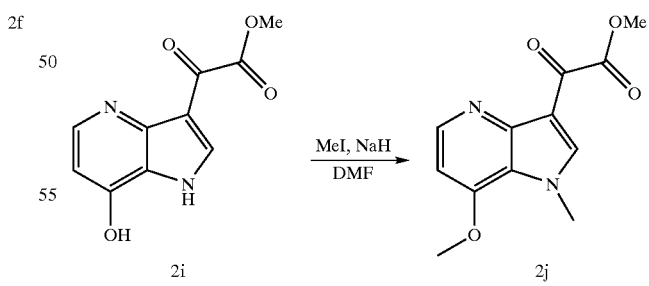

Preparation of compound 2j, Methyl (7-methoxyl-1-methyl-4-azaindol-3-yl)-oxoacetate: To a solution of compound 2i (27 mg) in 10 ml of dry DMF was added 4.4 mg of NaH. After 1 hour, 26 mg of MeI was added and the mixture was stirred at room temperature for 10 hours. DMF was then removed under vaccum to provide a crude product 2j which was used in the further reaction without purification.

Characterization of Compounds 2j:

Compound 2j, Methyl (7-methoxy-1-methyl-4-azaindol-3-yl)-oxoacetate: MS m/z: (M+H)+ calcd for $C_{12}H_{13}N_2O_4$: 249.09; found 249.33. HPLC retention time: 0.91 minutes (column A).

2) Preparation of Potassium Azaindole 3-Glyoxylate 3

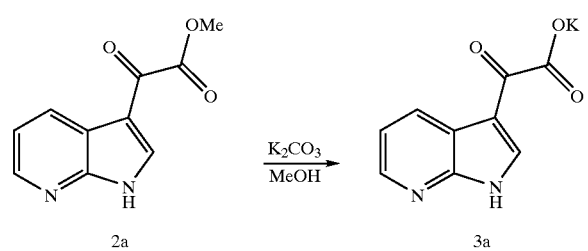

Preparation of Potassium (7-azaindol-3-yl)-oxoacetate 3a: Compound 2a (43 g, 0.21 mol) and $K_2CO_3$ (56.9 g, 0.41 mol) were dissolved in MeOH (200 ml) and $H_2O$ (200 ml). After 8 hours, product 3a precipitated out from the solution. Filtration afforded 43 g of compound 3a as a white solid in 90.4% yield.

Characterization of Compounds 3:

Compound 3a, Potassium (7-azaindol-3-yl)-oxoacetate: $^1$H NMR (300 MHz, DMSO-$d_6$) δ 8.42 (d, 1H, J=7.86 Hz), 8.26 (d, 1H, J=4.71 Hz), 8.14 (s, 1H), 7.18 (dd, 1H, J=7.86, 4.71 Hz); $^{13}$C NMR (75 MHz, DMSO-$d_6$) δ 169.4, 148.9, 143.6, 135.1, 129.3, 118.2, 117.5, 112.9. MS m/z: (M+H)+ of the corresponding acid of compound 3a (3a-K+H) calcd for $C_9H_7N_2O_3$: 191.05; found 190.97. HPLC retention time: 0.48 minutes (column A).

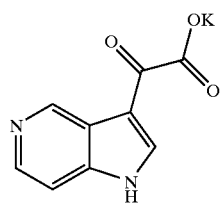

Compound 3b, Potassium (5-azaindol-3-yl)-oxoacetate: MS m/z: (M+H)+ of the corresponding acid of compound 3b (3b-K+H) calcd for $C_9H_7N_2O_3$: 191.05; found 191.02. HPLC retention time: 0.13 minutes (column A).

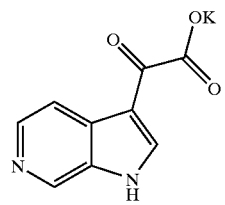

Compound 3c, Potassium (6-azaindol-3-yl)-oxoacetate: MS m/z: (M+H)+ of the corresponding acid of compound 3c (3c-K+H) calcd for $C_9H_7N_2O_3$: 191.05; found 190.99. HPLC retention time: 0.23 minutes (column A).

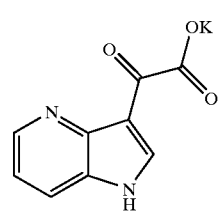

Compound 3d, Potassium (4-azaindol-3-yl)-oxoacetate: MS m/z: (M+H)+ of the corresponding acid of compound 3d (3d-K+H) calcd for $C_9H_7N_2O_3$: 191.05; found 190.87. HPLC retention time: 0.19 minutes (column A).

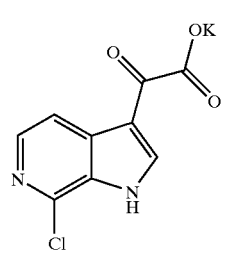

Compound 3e, Potassium (7-chloro-6-azaindol-3-yl)-oxoacetate: MS m/z: (M+H)+ of the corresponding acid of compound 3e (3e-K+H)+ calcd for $C_9H_6ClN_2O_3$: 225.01; found 224.99. HPLC retention time: 0.93 minutes (column A).

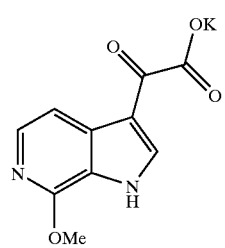

Compound 3f, Potassium (7-methoxy-6-azaindol-3-yl)-oxoacetate: MS m/z: (M+H)+ of the corresponding acid of compound 3f (3f-K+H)+ calcd for $C_{10}H_9N_2O_4$: 221.06; found 220.97. HPLC retention time: 0.45 minutes (column A).

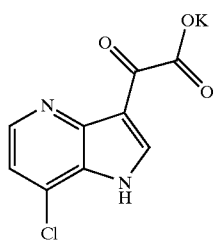

Compound 3 h, Potassium (7-chloro-4-azaindol-3-yl)-oxoacetate: MS m/z: (M+H)+ of the corresponding acid of compound 3h (3h-K+H)+ calcd for $C_9H_6ClN_2O_3$: 225.01; found 225.27. HPLC retention time: 0.33 minutes (column A).

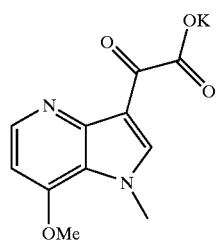

Compound 3j, Potassium (7-methoxyl-1-methyl-4-azaindol-3-yl)-oxoacetate: MS m/z: (M+H)+ of the corresponding acid of compound 3j (3j-K+H)+ calcd for $C_{11}H_{11}N_2O_4$: 235.07; found 235.01. HPLC retention time: 0.36 minutes (column A).

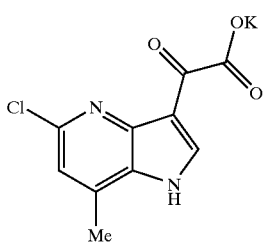

Compound 3ak, Potassium (5-chloro-7-methyl-4-azaindol-3-yl)-oxoacetate: MS m/z: (M+H)+ of the corresponding acid of compound 3ak (3ak-K+H)+ calcd for $C_{10}H_8ClN_2O_3$: 239.02; found 238.94. HPLC retention time: 1.24 minutes (column B).

1) Preparation of Azaindole Piperazine Diamide 5 Typical Procedure for the Preparation of Compounds in Scheme 3

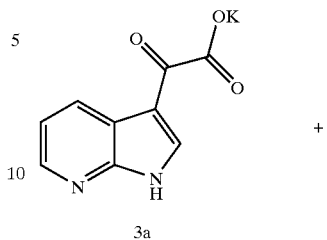

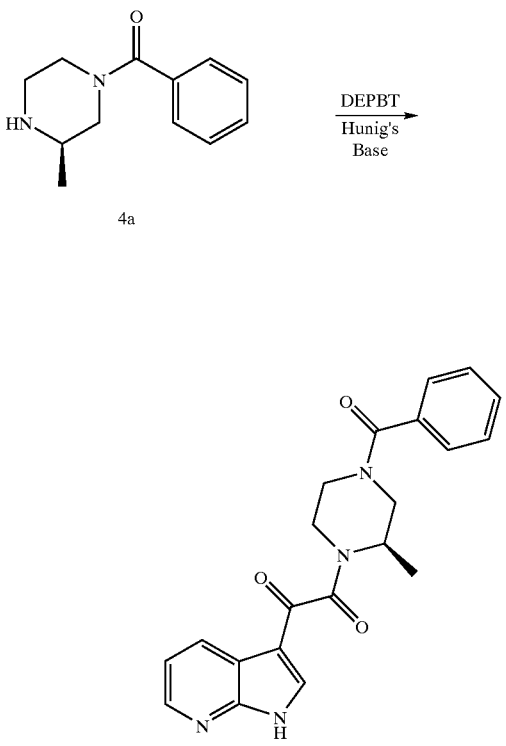

Preparation of (R)-N-(benzoyl)-3-methyl-N'-[(7-azaindol-3-yl)-oxoacetyl]-piperazine 5a: Potassium 7-azaindole 3-glyoxylate 3a (25.4 g, 0.111 mol), (R)-3-methyl-N-benzoylpiperazine 4a (22.7 g, 0.111 mol), 3-(diethoxyphosphoryloxy)-1,2,3-benzotriazin-4(3H)-one (DEPBT) (33.3 g, 0.111 mol) and Hunig's Base (28.6 g, 0.222 mol) were combined in 500 ml of DMF. The mixture was stirred at room temperature for 8 hours.

DMF was removed via evaporation at reduced pressure and the residue was partitioned between ethyl acetate (2000 ml) and 5% $Na_2CO_3$ aqueous solution (2×400 ml). The aqueous layer was extracted with ethyl acetate (3×300 ml). The organic phase combined and dried over anhydrous $MgSO_4$. Concentration in vacuo provided a crude product, which was purified by silica gel column chromatography with EtOAc/MeOH (50:1) to give 33 g of product 5a in 81% yield.

Typical Procedure for the Preparation of Compounds in Scheme 4

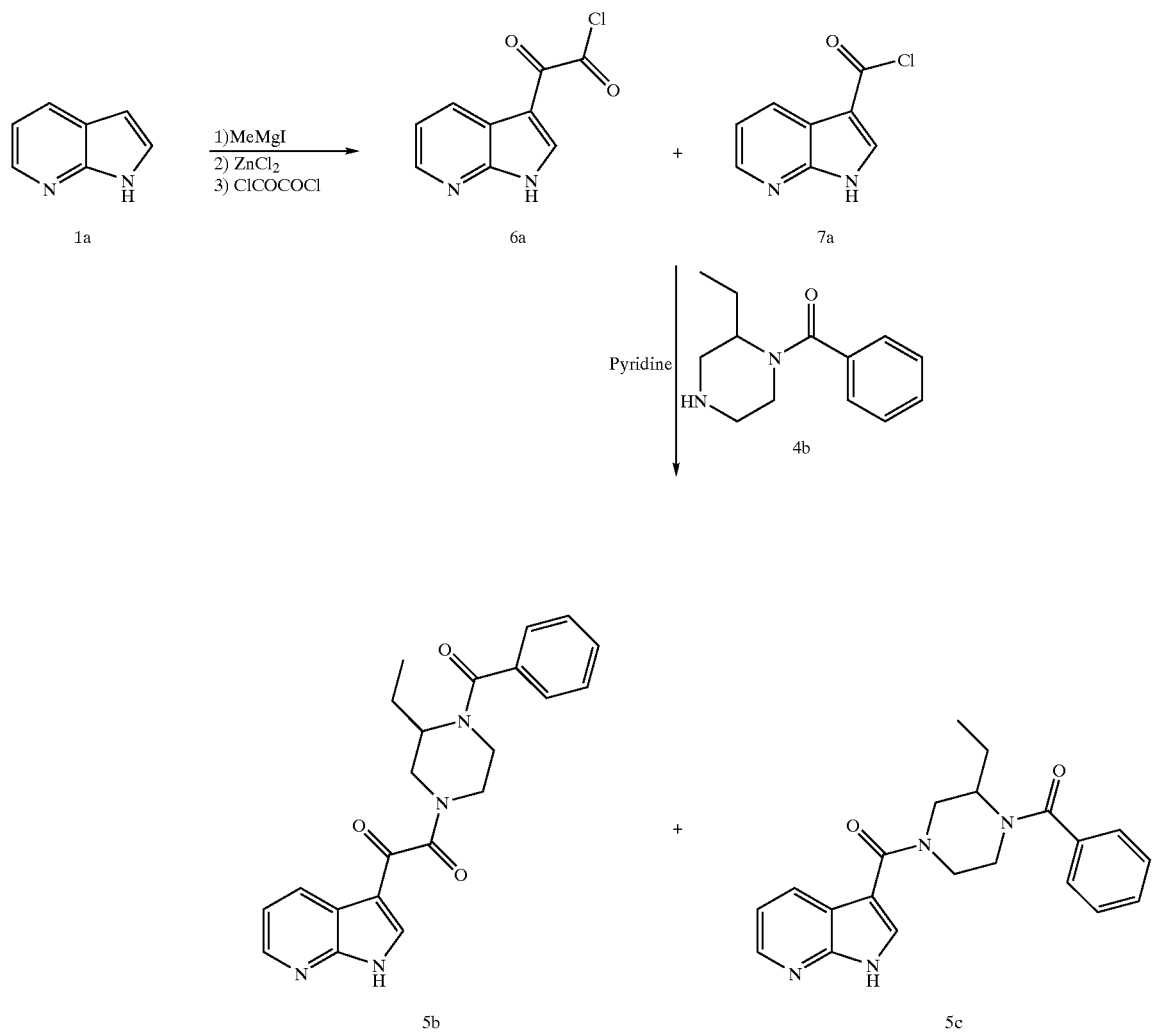

Preparation of N-(benzoyl)-2-ethyl-N'-[(7-azaindol-3-yl)-oxoacetyl]-piperazine 5b and N-(benzoyl)-2-ethyl-N'-[(7-azaindol-3-yl)-carbonyl]-piperazine 5c: To a solution of 7-azaindole 1a (1.0 g, 8.5 mmol) in dry diethyl ether (20 ml), 3.1 ml of MeMgI (3.0M in $Et_2O$, 9.3 mmol) was added at room temperature. The resulting mixture was stirred at room temperature for 1 hour before $ZnCl_2$ (1M in ether, 10.2 ml, 10.2 mmol) was added. One hour later, oxalyl chloride (10.7 g, 85 mmol) was injected into the solution cautiously. After the reaction was stirred for 8 hours, solvent and excess oxayl chloride were removed under vaccum to give a residue containing a mixture of 6a and 7a.

After the residue was dissolved in dry $CH_3CN$ (8 ml), mono-benzoylated piperazine 4b (0.25 g, 1.15 mmol) and pyridine (1 g, 12.7 mmol) were added into the solution subsequently. 1 hour later, solvents were removed and residue was purified using Shimadzu automated preparative HPLC System to give compound 5b (20 mg, 0.6%) and compound 5c (16 mg, 0.5%).

Characterization of Compounds 5 with the Following Sub-structure:

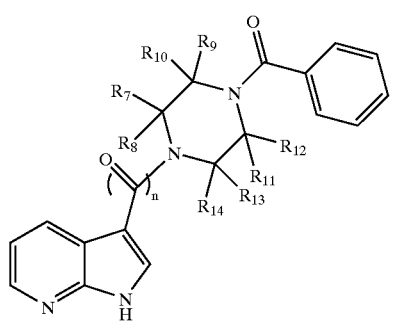

Compound 5a, n=2, $R_{7-13}$=H, $R_{14}$=(R)-Me, (R)-N-(benzoyl)-3-methyl-N'-[(7-azaindol-3-yl)-oxoacetyl]-piperazine: $^1$H NMR (300 MHz, $CD_3OD$) δ 8.57 (d, 1H, J=5.97 Hz), 8.38 (d, 1H, J=4.20 Hz), 8.27 (m, 1H), 7.47 (s, 5H), 7.35 (t, 1H, J=5.13 Hz), 4.75–2.87 (m, 7H), 1.31 (b, 3H); $^{13}$C NMR (75 MHz, CD$_3$OD) δ 185.6, 172.0, 166.3, 148.9, 144.6, 137.0, 134.8, 130.2, 129.9, 128.4, 126.6, 118.6, 118.0, 112.2, 61.3, 50.3, 45.1, 35.5, 14.9, 13.7. MS m/z: (M+H)$^+$ calcd for C$_{21}$H$_{21}$N$_4$O$_3$: 377.16; found 377.18. HPLC retention time: 1.21 minutes (column A).

Compound 5ai, n=2, R$_{7-13}$=H, R$_{14}$=Me, N-(benzoyl)-3-methyl-N'-[(7-azaindol-3-yl)-oxoacetyl]-piperazine: MS m/z: (M+H)$^+$ calcd for C$_{21}$H$_{21}$N$_4$O$_3$: 377.16; found 377.05.

Compound 5b, n=2, R$_{7-8}$=R$_{10-14}$=H, R$_9$=Et, N-(benzoyl)-2-ethyl-N'-[(7-azaindol-3-yl)-oxoacetyl]-piperazine: $^1$H NMR (500 MHz, CD$_3$OD) δ 8.63 (s, 1H), 8.40 (s, 1H), 8.25 (m, 1H), 7.42 (m, 6H), 4.70–2.90 (m, 7H), 1.80–0.60 (m, 5H); $^{13}$C NMR (125 MHz, CD$_3$OD) δ 186.8, 174.2, 168.3, 149.6, 145.4, 138.8, 136.9, 132.6, 131.3, 130.0, 128.0, 120.2, 117.7, 114.1, 58.4, 52.2, 47.5, 44.8, 23.0, 10.9, 10.7. MS m/z: (M+H)$^+$ calcd for C$_{22}$H$_{23}$N$_4$O$_3$: 391.18; found 391.22. HPLC retention time: 1.35 minutes (column A).

Compound 5c, n=1, R$_{7-8}$=R$_{10-14}$=H, R$_9$=Et, N-(benzoyl)-2-ethyl-N'-[(7-azaindol-3-yl)-carbonyl]-piperazine: $^1$H NMR (500 MHz, CD$_3$OD) δ 8.33(m, 2H), 7.87 (s, 1H), 7.47 (m, 5H), 7.33 (m, 1H), 4.74–2.90 (m, 7H), 1.78–0.75 (m, 5H); $^{13}$C NMR (125 MHz, CD$_3$OD) δ 168.0, 164.2, 162.8, 147.0, 142.8, 136.9, 133.1, 132.8, 131.3, 130.4, 130.0, 128.0, 118.4, 110.3, 57.0, 53.4, 46.7, 24.0, 10.7. MS m/z: (M+H)$^+$ calcd for C$_{21}$H$_{23}$N$_4$O$_2$: 363.18; found 363.22. HPLC retention time: 1.14 minutes (column A).

Compound 5d, n=2, R$_{7-14}$=H, N-(benzoyl)-N'-[(7-azaindol-3-yl)-oxoacetyl]-piperazine: $^1$H NMR (500 MHz, CD$_3$OD) δ 8.62 (s, 1H), 8.44 (s, 1H), 8.26 (s, 1H), 7.46 (s, 5H), 7.29 (m, 1H), 3.97–3.31 (m, 8H). MS m/z: (M+H)$^+$ calcd for C$_{20}$H$_{19}$N$_4$O$_3$: 363.15; found 363.24. HPLC retention time: 1.18 minutes (column A).

Compound 5e, n=2, R$_{7-8}$=R$_{10-14}$=H, R$_9$=Me, N-(benzoyl)-2-methyl-N'-[(7-azaindol-3-yl)-oxoacetyl]-piperazine: $^1$H NMR (500 MHz, CD$_3$OD) δ 8.64 (s, 1H), 8.51 (s, 1H), 8.28 (m, 1H), 7.42 (m, 6H), 4.48–2.90 (m, 7H), 1.26 (m, 3H); $^{13}$C NMR (125 MHz, CD$_3$OD) □δ 185.3, 171.4, 166.8, 164.0, 147.9, 143.6, 137.3, 135.3, 131.2, 129.8, 128.4, 126.2, 118.6, 112.4, 49.4, 45.9, 45.6, 45.1, 40.8, 40.4, 14.1. MS m/z: (M+H)$^+$ calcd for C$_{21}$H$_{21}$N$_4$O$_3$: 377.16; found 377.21. HPLC retention time: 1.26 minutes (column A).

Compound 5f, n=2, R$_{7-13}$=H, R$_{14}$=(S)-Me, (S)-N-(benzoyl)-3-methyl-N'-[(7-azaindol-3-yl)-oxoacetyl]-piperazine: $^1$H NMR (500 MHz, CD$_3$OD) δ 8.64 (s, 1H), 8.39 (s, 1H), 8.26 (m, 1H), 7.44 (m, 6H), 4.71–3.79 (m, 7H), 1.26 (m, 3H); $^{13}$C NMR (125 MHz, CD$_3$OD) δ 185.5, 171.9, 166.0, 158.4, 147.6, 143.5, 137.2, 134.8, 131.3, 129.8, 128.3, 126.6, 118.6, 112.4, 50.3, 45.1, 41.2, 40.3, 14.9, 13.7. MS m/z: (M+H)$^+$ calcd for C$_{21}$H$_{21}$N$_4$O$_3$: 377.16; found 377.21. HPLC retention time: 1.25 minutes (column A).

Compound 5g, n=2, R$_{7-13}$=H, R$_{14}$=Et, N-(benzoyl)-3-ethyl-N'-[(7-azaindole-3-yl)-oxoacetyl]-piperazine: $^1$H NMR (500 MHz, CD$_3$OD) δ 8.65 (b, 1H), 8.40 (s, 1H), 8.27 (m, 1H), 7.46 (m, 6H), 4.73–3.00 (m, 7H), 1.80–0.58 (m, 5H); $^{13}$C NMR (125 MHz, CD$_3$OD) δ 187.1, 173.0, 168.0, 149.2, 145.0, 138.8, 136.4, 133.0, 131.4, 129.9, 128.2, 120.2, 114.1, 57.5, 46.0, 43.0, 37.5, 23.0, 10.7. MS m/z: (M+H)$^+$ calcd for C$_{22}$H$_{23}$N$_4$O$_3$: 391.18; found 391.20. HPLC retention time: 1.33 minutes (column A).

Compound 5h, n=2, R$_{7-12}$=H, R$_{13}$=R$_{14}$=Me, N-(benzoyl)-3,3-dimethyl-N'-[(7-azaindol-3-yl)-oxoacetyl]-piperazine: MS m/z: (M+H)$^+$ calcd for C$_{22}$H$_{23}$N$_4$O$_3$: 391.18; found 390.98. HPLC retention time: 1.22 minutes (column A).

Compound 5i, n=2, R$_{7-8}$=R$_{10-13}$=H, R$_9$=R$_{14}$=Me, trans-N(benzoyl)-2,5-dimethyl-N'-[(7-azaindol-3-yl)-oxoacetyl]-piperazine: $^1$H NMR (500 MHz, CD$_3$OD) δ 8.58 (m, 1H), 8.37 (d, 1H, J=15.7 Hz), 8.25 (m, 1H), 7.77 (m, 1H), 7.46 (m, 5H), 5.09–3.16 (m, 6H), 1.30 (m, 6H). MS m/z: (M+H)$^+$ calcd for C$_{22}$H$_{23}$N$_4$O$_3$: 391.18; found 391.11. HPLC retention time: 1.22 minutes (column A).

Compound 5ab, n=2, R$_{7-9}$=R$_{10-13}$=H, R$_{14}$=i-Pr, N-(benzoyl)-3-iso-Propyl-N'-[(7-azaindol-3-yl)-oxoacetyl]-piperazine: MS m/z: (M+H)$^+$ calcd for C$_{23}$H$_{25}$N$_4$O$_3$: 405.19; found 405.22. HPLC retention time: 1.52 minutes (column A).

Compound 5ac, n=2, R$_{7-8}$=R$_{10-14}$=H, R$_9$=i-Pr, N-(benzoyl)-2-iso-Propyl-N'-[(7-azaindol-3-yl)-oxoaetyl]-piperazine: MS m/z: (M+H)$^+$ calcd for C$_{23}$H$_{25}$N$_4$O$_3$: 405.19; found 405.25. HPLC retention time: 1.53 minutes (column A).

Compound 5ad, n=1, R$_{7-8}$=R$_{10-14}$=H, R$_9$=i-Pr, N-(benzoyl)-2-iso-Propyl-N'-[(7-azaindol-3-yl)-carbonyl]-piperazine: MS m/z: (M+H)$^+$ calcd for C$_{22}$H$_{25}$N$_4$O$_2$: 377.20; found 377.23. HPLC retention time: 1.34 minutes (column A).

Compound 5ae, n=2, R$_{7-8}$=R$_{10-14}$=H, R$_9$=Pentyl, trans-N-(benzoyl)-2-Pentyl-N'-[(7-azaindol-3-yl)-oxoacetyl]-piperazine: MS m/z: (M+H)$^+$ calcd for C$_{25}$H$_{29}$N$_4$O$_3$: 433.22; found 433.42. HPLC retention time: 1.74 minutes (column A).

Characterization of Compounds 5 with the Following Sub-structure:

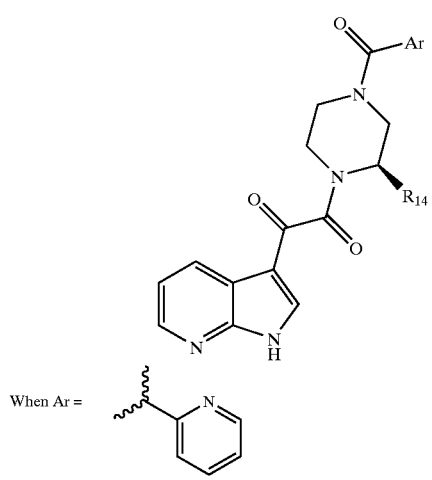

Compound 5j, R$_{14}$=H, N-(pyridin-2-yl)-N'-[(7-azaindol-3-yl)-oxoacetyl]-piperazine: $^1$H NMR (500 MHz, CD$_3$OD) δ 8.65–7.30 (m, 8H), 4.00–3.33 (m, 8H). MS m/z: (M+H)$^+$ calcd for C$_{19}$H$_{18}$N$_5$O$_3$: 364.14; found 364.08. HPLC retention time: 0.97 minutes (column A).

Compound 5k, R$_{14}$=(R)-Me, (R)-N-(pyridin-2-yl)-3-methyl-N'-[(7-azaindol-3-yl)-oxoacetyl]-piperazine: $^1$H NMR (300 MHz, CD$_3$OD) δ 8.67–7.38 (m, 8H), 4.76–3.00 (m, 7H), 1.35 (m, 3H); $^{13}$C NMR (75 MHz, CD$_3$OD) δ 186.0, 168.9, 166.6, 152.9, 148.5, 144.0, 138.7, 137.8, 131.8, 125.6, 124.0, 119.0, 112.9, 51.3, 50.9, 50.7, 46.7, 46.2, 45.7, 42.6, 42.0, 41.8, 40.8, 36.6, 35.7, 15.5, 14.2. MS m/z: (M+H)$^+$ calcd for C$_{20}$H$_{20}$N$_5$O$_3$: 378.16; found 378.14. HPLC retention time: 1.02 minutes (column A).

When Ar = 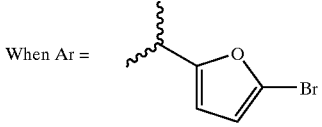

Compound 5l, $R_{14}$=(R)-Me, (R)-N-(5-bromo-furan-2-yl)-3-methyl-N'-[(7-azaindol-3-yl)-oxoacetyl]-piperazine: $^1$H NMR (500 MHz, $CD_3OD$) δ 8.59 (d, 1H, J=9.4 Hz), 8.37 (s, 1H), 8.26 (m, 1H), 7.34 (d, 1H, J=10.1 Hz), 7.06 (s, 1H), 6.59 (s, 1H), 4.56–3.16 (m, 7H), 1.30 (m, 3H); $^{13}$C NMR (125 MHz, $CD_3OD$). δ 187.2, 167.8, 161.0, 150.1, 149.8, 145.8, 138.7, 132.1, 127.0, 120.5, 120.2, 119.8, 114.8, 113.9, 51.8, 47.0, 42.0, 37.0, 16.6, 15.4. MS m/z: $(M+H)^+$ calcd for $C_{19}H_{18}BrN_4O_4$: 445.05; found 445.18. HPLC retention time: 1.35 minutes (column A).

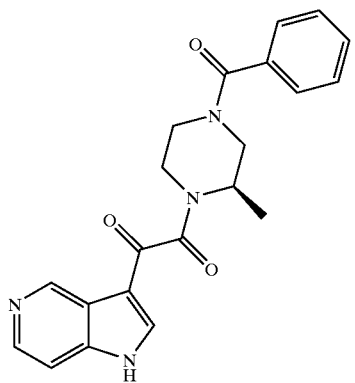

5m

Characterization of Compound 5m:
Compound 5m, (R)-N-(benzoyl)-3-methyl-N'-[(5-azaindol-3-yl)-oxoacetyl]-piperazine: $^1$H NMR (500 MHz, $CD_3OD$) δ 9.62 (b, 1H), 8.72 (m, 1H), 8.61 (d, 1H, J=4.5 Hz), 8.16 (d, 1H, J=5.8 Hz), 7.51 (b, 6H), 4.90–3.10 (m, 7H), 1.35 (b, 3H). MS m/z: $(M+H)^+$ calcd for $C_{21}H_{21}N_4O_3$ 377.16, found 377.15. HPLC retention time: 0.89 minutes (column A).

Characterization of Compounds 5 with the Following Sub-structure:

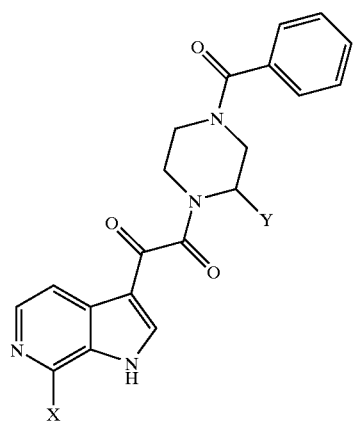

5

Compound 5p, X=H, Y=H, N-(benzoyl)-N'-[(6-azaindol-3-yl)-oxoacetyl-]-piperazine: MS m/z: $(M+H)^+$ calcd for $C_{20}H_{19}N_4O_3$ 363.15, found 363.09. HPLC retention time: 0.96 minutes (column A).

Compound 5q, X=H, Y=Me, N-(benzoyl)-3-Methyl-N'-[(6-azaindol-3-yl)-oxoacetyl]-piperazine: MS m/z: $(M+H)^+$ calcd for $C_{21}H_{21}N_4O_3$ 377.16, found 377.11. HPLC retention time: 0.99 minutes (column A).

Compound 5r, X=H, Y=(R)-Me, (R)-N-(benzoyl)-3-Methyl-N'-[(6-azaindol-3-yl)-oxoacetyl]-piperazine: MS m/z: $(M+H)^+$ calcd for $C_{21}H_{21}N_4O_3$ 377.16, found 377.10. HPLC retention time: 0.99 minutes (column A).

Compound 5s, X=H, Y=(S)-Me, (S)-N-(benzoyl)-3-Methyl-N'-[(6-azaindol-3-yl)-oxoacetyl]-piperazine: MS m/z: $(M+H)^+$ calcd for $C_{21}H_{21}N_4O_3$ 377.16, found 377.10. HPLC retention time: 1.00 minutes (column A).

Compound 5t, X=Cl, Y=H, N-(benzoyl)-N'-[(7-Chloro-6-azaindol3-yl)-oxoacetyl]-piperazine: MS m/z: $(M+H)^+$ calcd for $C_{20}H_{18}ClN_4O_3$ 397.11, found 397.26. HPLC retention time: 1.60 minutes (column B).

Compound 5u, X=Cl, Y=(R)-Me, (R)-N-(benzoyl)-3-Methyl-N'-[(7-Chloro-6-azaindol-3-yl)-oxoacetyl]-piperazine: MS m/z: $(M+H)^+$ calcd for $C_{21}H_{20}ClN_4O_3$ 411.12, found 411.16. HPLC retention time: 1.43 minutes (column A).

Compound 5v, X=OMe, Y=(R)-Me, (R)-N-(benzoyl)-3-Methyl-N'-[(7-Methoxy-6-azaindol-3-yl)-oxoacetyl]-piperazine: MS m/z: $(M+H)^+$ calcd for $C_{21}H_{20}ClN_4O_3$ 407.17, found 407.13. HPLC retention time: 1.31 minutes (column A).

Characterization of Compounds 5 with the Following Sub-structure:

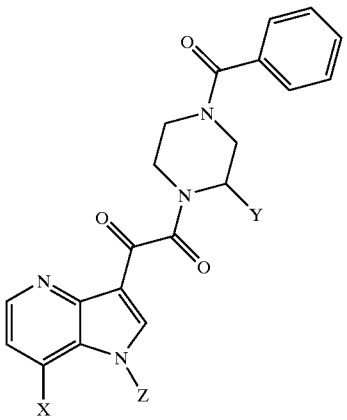

Compound 5w, X=H, Y=(R)-Me, Z=H, (R)-N-(benzoyl)-3-Methyl-N'-[(4-azaindol-3-yl)-oxoacetyl]-piperazine: MS m/z: $(M+H)^+$ calcd for $C_{21}H_{21}N_4O_3$ 377.16, found 377.14. HPLC retention time: 0.96 minutes (column A).

Compound 5x, X=$CH_3$, Y=(R)-Me, Z=H, (R)-N-(benzoyl)-3-Methyl-N'-[(7-Methyl-4-azaindol-3-yl)-oxoacetyl]-piperazine: MS m/z: $(M+H)^+$ calcd for $C_{21}H_{21}N_4O_3$ 391.18, found 391.15 HPLC retention time: 1.15 minutes (column A).

Compound 5y, X=Cl, Y=(R)-Me, Z=H, (R)-N-(benzoyl)-3-Methyl-N'-[(7-Chloro-4-azaindol-3-yl)-oxoacetyl]-piperazine: MS m/z: $(M+H)^+$ calcd for $C_{21}H_{20}ClN_4O_3$ 411.12, found 411.04. HPLC retention time: 1.10 minutes (column A).

Compound 5z, X=OMe, Y=(R)-Me, Z=Me, (R)-N-(benzoyl)-3-Methyl-N'-[(7-Methoxy-1-methyl-4-azaindol-3-yl)-oxoacetyl]-piperazine: MS m/z: $(M+H)^+$ calcd for $C_{23}H_{25}N_4O_4$: 421.19, found 421.05. HPLC retention time: 1.06 minutes (column A).

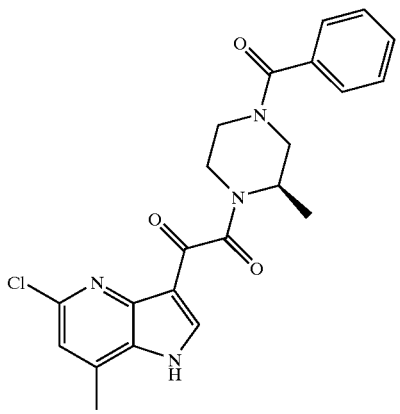

5ak

Compound 5ak, (R)-N-(benzoyl)-3-Methyl-N'-[(5-Chloro-7-methyl-4-azaindol-3-yl)-oxoacetyl]-piperazine: MS m/z: (M+H)$^+$ calcd for $C_{22}H_{22}ClN_4O_3$ 425.24, found 425.04. HPLC retention time: 1.72 minutes (column B).

Typical Procedure for Preparation of Compounds in Scheme 5,6 and 7

1) N-Oxide Formation (Equation 1, Scheme 5)

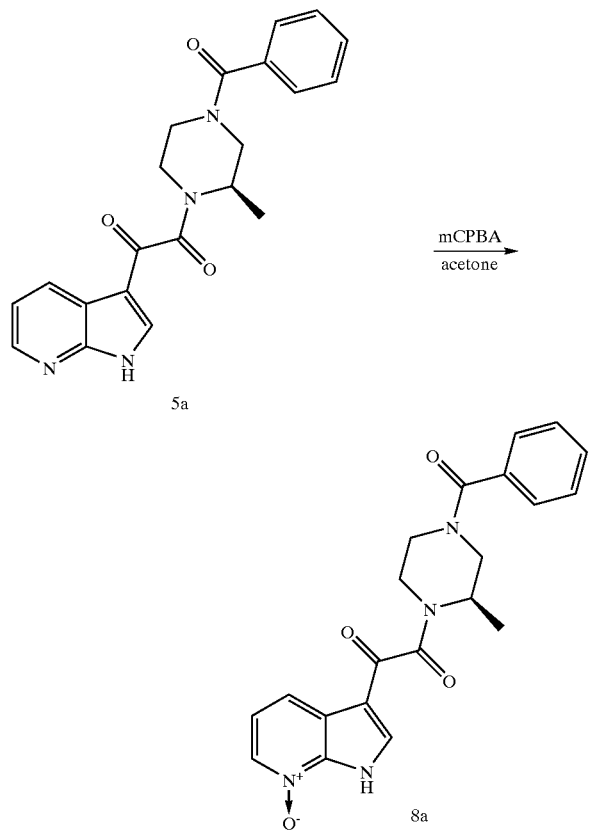

Preparation of (R)-N-(benzoyl)-3-methyl-N'-[(7-oxide-7-azaindol-3-yl)-oxoacetyl]-piperazine 8a: 10 g of 7-azaindole piperazine diamide 5a (26.6 mmol) was dissolved in 250 ml acetone. 9.17 g of mCPBA (53.1 mmol) was then added into the solution. Product 8a precipitated out from the solution as a white solid after 8 hours and was collected via filtration. After drying under vacuum, 9.5 g of compound 8a was obtained in 91% yield. No further purification was needed.

Characterization of Compound 8 with the Following Sub-structure:

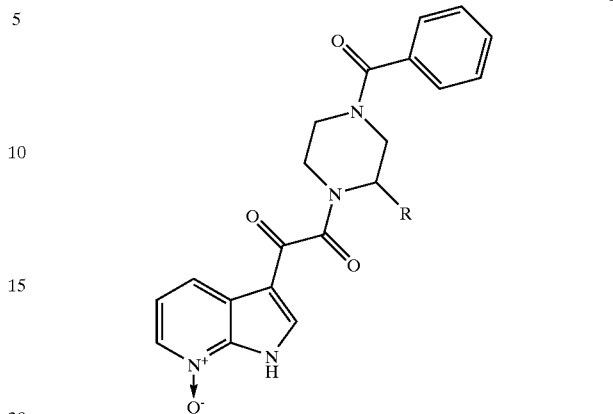

Compound 8a, R=(R)-Me, (R)-N-(benzoyl)-3-methyl-N'-[(7-oxide7-azaindol-3-yl)-oxoacetyl]-piperazine: $^1$H NMR (300 MHz, DMSO-d$_6$) δ 8.30 (d, 1H, J=12.2 Hz), 8.26 (d, 1H, J=10.1 Hz), 8.00 (d, 1H, J=7.41 Hz), 7.41 (s, 5H), 7.29 (m, 1H), 4.57–2.80 (m, 7H), 1.19 (b, 3H); $^{13}$C NMR (75 MHz, DMSO-d$_6$) δ 186.2, 170.0, 165.0, 139.5, 136.9, 136.7, 135.5, 133.5, 129.7, 128.5, 126.9, 121.6, 119.9, 113.6, 49.4, 44.3, 15.9, 14.8. MS m/z: (M+H)$^+$ calcd for $C_{21}H_{21}N_4O_4$: 393.16; found 393.16. HPLC retention time: 1.05 minutes (column A).

Compound 8e, R=H, N-(benzoyl)-N'-[(7-oxide-7-azaindol-3-yl)-oxoacetyl]-piperazine: MS m/z: (M+H)$^+$ calcd for $C_{20}H_{19}N_4O_4$: 379.14; found 379.02. HPLC retention time: 1.15 minutes (column A).

Compound 8c, R=(S)-Me, (S)-N-(benzoyl)-3-methyl-N'-[(7-oxide-7-azaindol-3-yl)-oxoacetyl]-piperazine: MS m/z: (M+H)$^+$ calcd for $C_{21}H_{21}N_4O_4$: 393.16; found 393.05.

Compound 8d, R=Me, N-(benzoyl)-3-methyl-N'-[(7-oxide-7azaindol-3-yl)-oxoacetyl]-piperazine: MS m/z: (M+H)$^+$ calcd for $C_{21}H_{21}N_4O_4$: 393.16; found 393.05.

Characterization of Compound 8b:

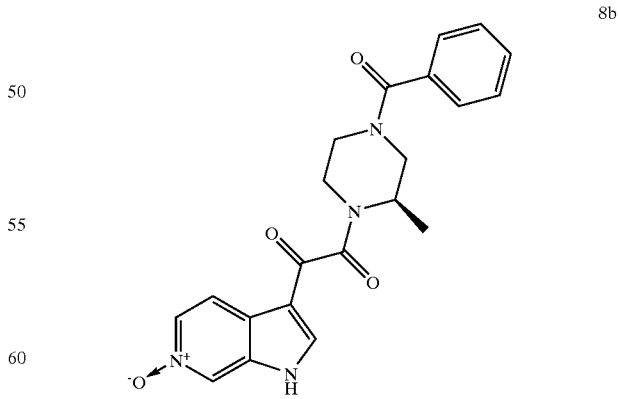

Compound 8b, (R)-N-(benzoyl)-3-methyl-N'-[(6-oxide-6-azaindol-3-yl)-oxoacetyl]-piperazine: MS m/z: (M+H)$^+$ calcd for $C_{21}H_{21}N_4O_4$: 393.16; found 393.08. HPLC retention time: 1.06 minutes (column A).

2) Chlorination (Equation 2, Scheme 5)

3) Nitration of N-Oxide (Equation 10, Scheme 6)

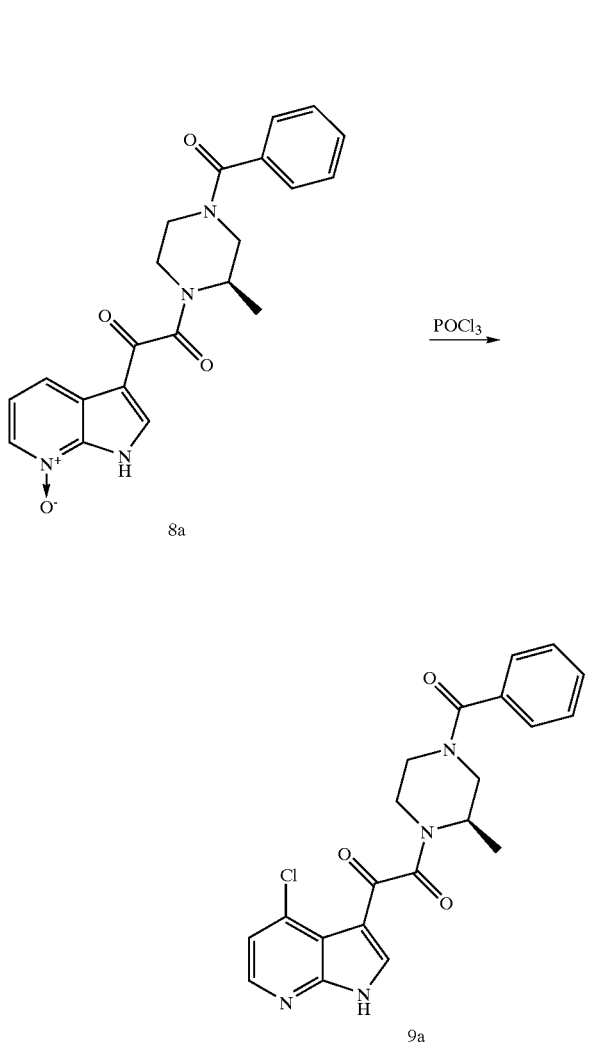

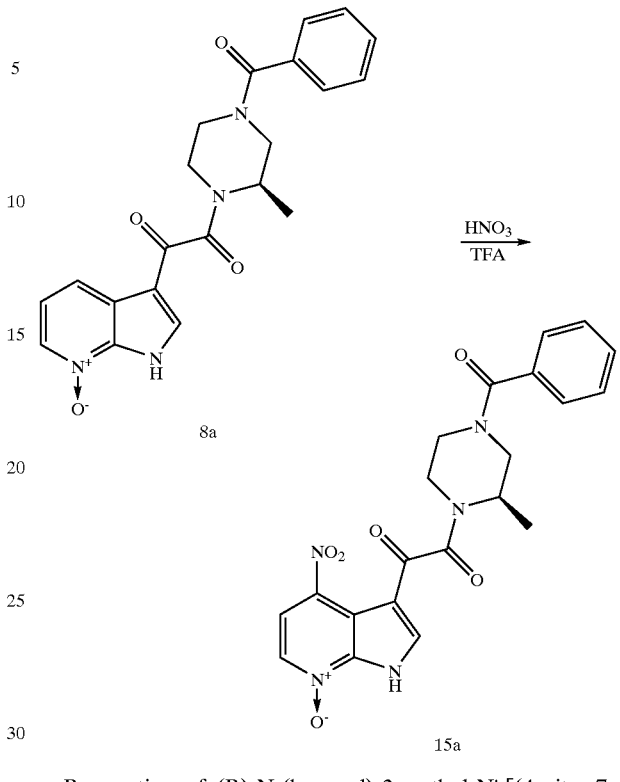

Preparation of (R)-N-(benzoyl)-3-methyl-N'-[(4-nitro-7-oxide-7-azaindol-3-yl)-oxoacetyl]-piperazine 15a: N-oxide 8a (10.8 g, 27.6 mmol) was dissolved in 200 ml of trifluoroacetic acid and 20 ml of fuming nitric acid. The reaction mixture was stirred for 8 hours and quenched with methanol. After filtration, the filtrate was concentrated under vacuum to give crude product 15a as a brown solid, which was carried to the next step without further purification. A small amount of crude product was purified using a Shimadzu automated preparative HPLC System to give compound 3 mg of compound 15a.

Characterization of Compound 15 with the Following Sub-structure:

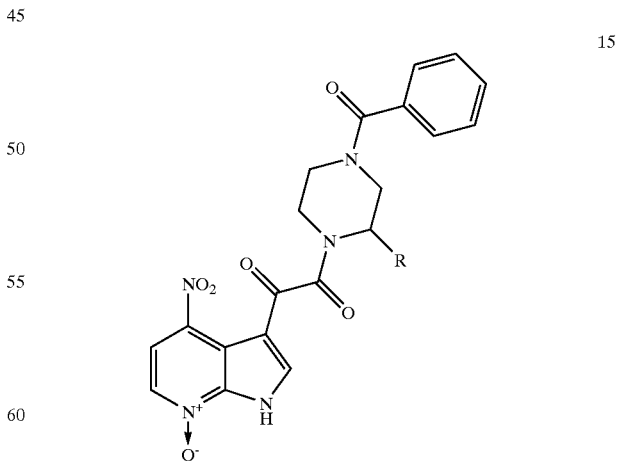

Preparation of (R)-N-(benzoyl)-3-methyl-N'-[(4-chloro-7-azaindol-3-yl)-oxoacetyl]-piperazine 9a: 55 mg of 7-azaindole piperazine diamide N-Oxide (0.14 mmol) 8a was dissolved in 5 ml of POCl$_3$. The reaction mixture was heated at 60° C. for 4 hours. After cooling, the mixture was poured into ice cooled saturated NaHCO$_3$ solution and the aqueous phase was extracted with EtOAc (3×50 ml). The combined organic layer was dried over MgSO$_4$ and concentrated under vacuum. The crude product was purified using a Shimadzu automated preparative HPLC System to give compound 9a (15 mg, 26%).

Characterization of Compound 9a:

Compound 9a, (R)-N-(benzoyl)-3-methyl-N'-[(4-chloro-7-azaindol-3-yl)-oxoacetyl]-piperazine: $^1$H NMR (500 MHz, DMSO-d$_6$) δ 13.27 (b, 1H), 8.46 (m, 2H), 7.43 (m, 6H), 5.00–2.80 (m, 7H), 1.23 (b, 3H). MS m/z: (M+H)$^+$ calcd for C$_{21}$H$_{20}$ClN$_4$O$_3$: 411.12; found 411.09. HPLC retention time: 1.32 minutes (column A).

Compound 15a, R=(R)-Me, (R)-N-(benzoyl)-3-methyl-N'-[(4-nitro-7-oxide-7-azaindol-3-yl)-oxoacetyl]-piperazine: MS m/z: (M+H)$^+$ calcd for C$_{21}$H$_{20}$N$_5$O$_6$: 438.14; found 438.07. HPLC retention time: 1.18 minutes (column A).

Compound 15b, R=(S)-Me, (S)-N-(benzoyl)-3-methyl-N'-[(4-nitro-7-oxide-7-azaindol-3-yl)-oxoacetyl]-piperazine: MS m/z: (M+H)+ calcd for $C_{21}H_{20}N_5O_6$: 438.14; found 438.02. HPLC retention time: 1.18 minutes (column A).

Compound 15c, R=Me, N-(benzoyl)-3-methyl-N'-[(4-nitro-7-oxide-7-azaindol-3-yl)-oxoacety]-piperazine: MS m/z: (M+H)+ calcd for $C_{21}H_{20}N_5O_6$: 438.14; found 438.02. HPLC retention time: 1.18 minutes (column A).

4) Fluorination (Equation 5, Scheme 3)

5) Alkylation and Arylation (Equation 4, Scheme 5)

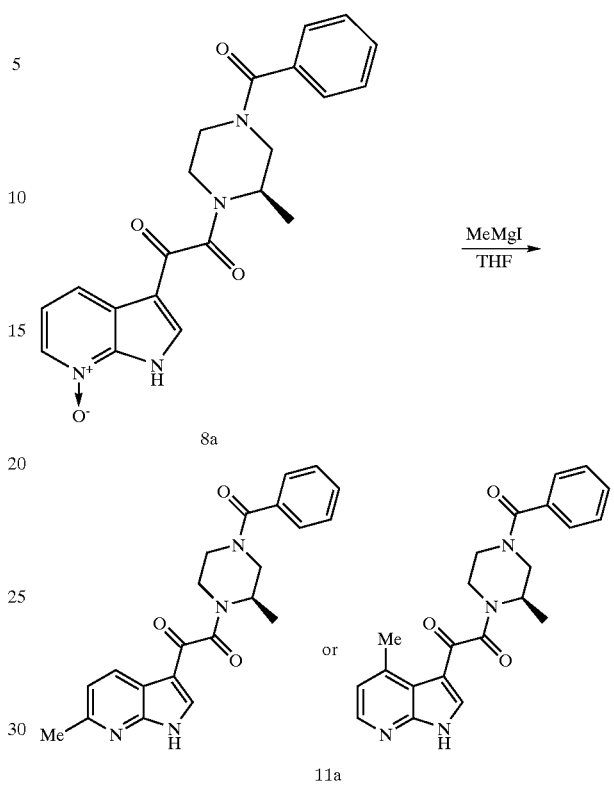

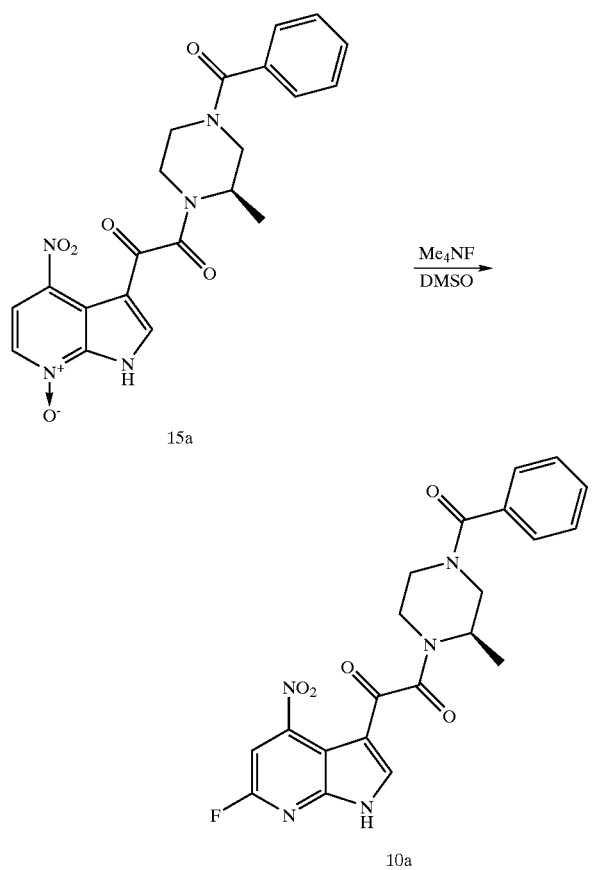

Preparation of (R)-N-(benzoyl)-3-methyl-N'-[(4-nitro-6-fluoro-7-azaindol-3-yl)-oxoacetyl]-piperazine 10a: 20 mg of crude 4-nitro-7-azaindole piperazine diamide N-oxide 15a and an excess of Me₄NF (300 mg) were dissolved in 5 ml of DMSO-d₆. The reaction mixture was heated at 100° C. for 8 hours. After cooling, DMSO-d₆ was removed by blowing nitrogen. The residue was partitioned between ethyl acetate (10 ml) and 2N NaOH solution (10 ml). The aqueous phase was extracted with EtOAc (2×10 ml). The organic layers were combined and concentrated under vacuum to give a residue, which was further purified using a Shimadzu automated preparative HPLC System to give compound of 10a (8.3 mg).

Characterization of Compound 10a:

Compound 10a: (R)-N-(benzoyl)-3-methyl-N'-[(4-nitro-6-fluoro-7-azaindol-3-yl)-oxoacetyl]-piperazine: ¹H NMR (300 MHz, acetone-d₆) δ 8.44 (d, 1H, J=8.24 Hz), 7.47 (s, 6H), 4.80–3.00 (m, 7H), 1.29 (b, 3H). MS m/z: (M+H)+ calcd for $C_{21}H_{19}FN_5O_5$: 440.14; found 440.14. HPLC retention time: 1.40 minutes (column B).

Preparation of (R)-N-(benzoyl)-3-methyl-N'-[(4 or 6)-methyl-7-azaindol-3-yl)-oxoacetyl]-piperazine 11a: An excess of MeMgI (3M in THF, 0.21 ml, 0.63 mmol) was added into a solution of 7-azaindole piperazine diamide N-oxide 8a (25 mg, 0.064 mmol). The reaction mixture was stirred at room temperature and then quenched with methanol. The solvents were removed under vacuum, the residue was diluted with methanol and purified using a Shimadzu automated preparative HPLC System to give compound 11a (6.7 mg, 27%).

Characterization of Compounds 11 with the Following Sub-structure:

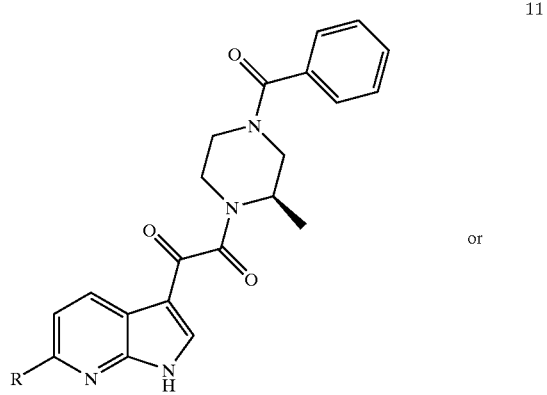

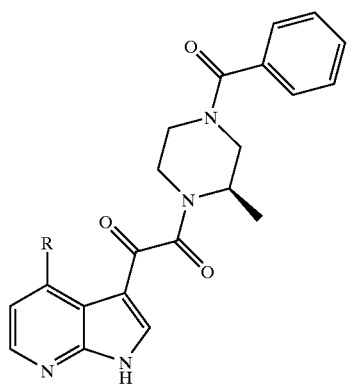

Compound 11a: R=Me, (R)-N-(benzoyl)-3-methyl-N'-[(4 or 6)-methyl-7-azaindol-3-yl)-oxoacetyl]-piperazine: MS m/z: (M+H)+ calcd for $C_{22}H_{23}N_4O_3$: 391.18; found 391.17. HPLC retention time: 1.35 minutes (column B).

Compound 11b: R=Ph, (R)-N-(benzoyl)-3-methyl-N'-[(4 or 6)-phenyl-7-azaindol-3-yl)-oxoacetyl]-perazine: MS m/z: (M+H)+ calcd for $C_{27}H_{25}N_4O_3$: 453.19; found 454.20. HPLC retention time: 1.46 minutes (column B).

Compound 11c, R=CH=CH2, (R)-N-(benzoyl)-3-methyl-N'-[(4 or 6)-vinyl-7-azaindol-3-yl)-oxoacetyl]-piperazine: MS m/z: (M+Na)+ calcd for $C_{23}H_{22}N_4NaO_3$: 425.16; found 425.23. HPLC retention time: 1.12 minutes (column A).

6) Nitrile Substitution and Chlorination (Equation 5, Scheme 5)

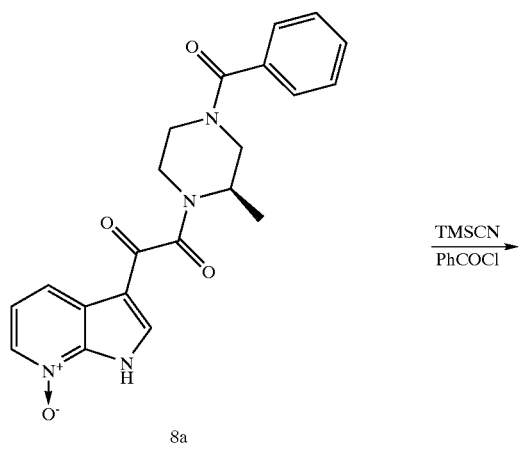

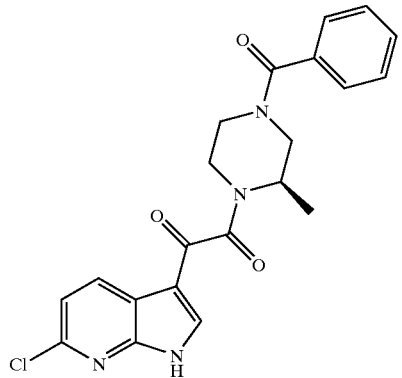

9b

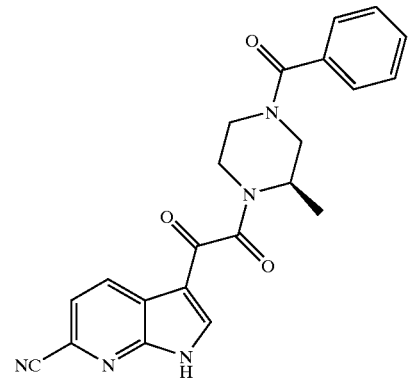

12a

Preparation of (R)-N-(benzoyl)-3-methyl-N'-[(6-chloro-7-azaindol-3-yl)-oxoacetyl]-piperazine 9b and (R)-N-(benzoyl)-3-methyl-N'-[(6-cyano-7-azaindol-3-yl)-oxoacetyl]-piperazine 12a: N-oxide 8a (0.20 g, 0.51 mmol) was suspended in 20 ml of dry THF, to which TMSCN (0.3 g, 3.0 mmol) and BzCl (0.28 g, 2.0 mmol) were added. The reaction mixture was stirred at room temperature for 2 hours, and then heated at reflux for 5 hours. After cooling, the mixture was poured into 100 ml of saturated $NaHCO_3$ and the aqueous phase extracted with EtOAc (3×50 ml). The organic phase was combined and concentrated under vacuum to give a residue, which was diluted with methanol and purified using a Shimadzu automated preparative HPLC System to give compound 12a (42 mg, 20%) and compound 9b (23 mg, 11%).

Characterization of Compounds 9b and 12a:

Compound 9b, (R)-N-(benzoyl)-3-methyl-N'-[(6-chloro-7-azaindol3-yl)-oxoacetyl]-piperazine: $^1$H NMR (500 MHz, DMSO-$d_6$) δ 8.39 (m, 2H), 7.42 (m, 6H), 5.00–2.80 (m, 7H), 1.19 (b, 3H); $^{13}$C NMR (125 MHz, DMSO-$d_6$). δ 185.8, 170.0, 165.1, 147.9, 145.1, 137.4, 135.4, 132.2, 129.5, 128.3, 126.8, 118.6, 116.1, 111.8, 49.3, 47.2, 44.2, 15.6,14.5. MS m/z: (M+H)+ calcd for $C_{21}H_{20}ClN_4O_3$: 411.12; found 411.09. HPLC retention time: 1.43 minutes (column A).

Compound 12a, (R)-N-(benzoyl)-3-methyl-N'-[(6-cyano-7-azaindol3-yl)-oxoacetyl]-piperazine: $^1$H NMR (500 MHz, DMSO-$d_6$) δ 8.67 (m, 2H), 7.86 (s, 1H), 7.42 (m, 5H), 4.80–2.80 (m, 7H), 1.22 (b, 3H); $^{13}$C NMR (125 MHz, DMSO-$d_6$) δ 185.7, 170.0, 164.8, 148.5, 140.9, 135.3, 130.3, 129.5, 128.3, 126.8, 126.2, 123.0, 120.4, 118.0, 111.8, 49.4, 47.3, 44.2, 15.6, 14.5. MS m/z: (M+H)+ calcd for $C_{22}H_{20}N_5O_3$: 402.16; found 402.13. HPLC retention time: 1.29 minutes (column A).

7) Hydroxylation (Equation 6, Scheme 5)

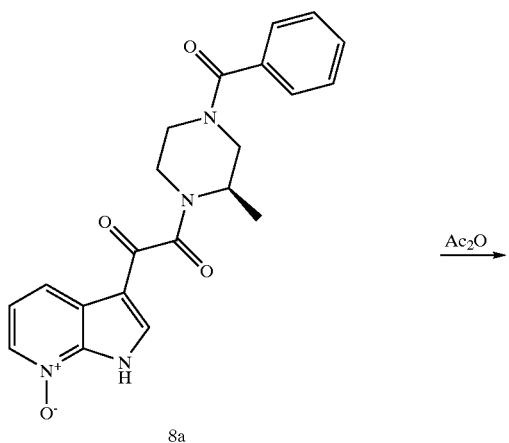

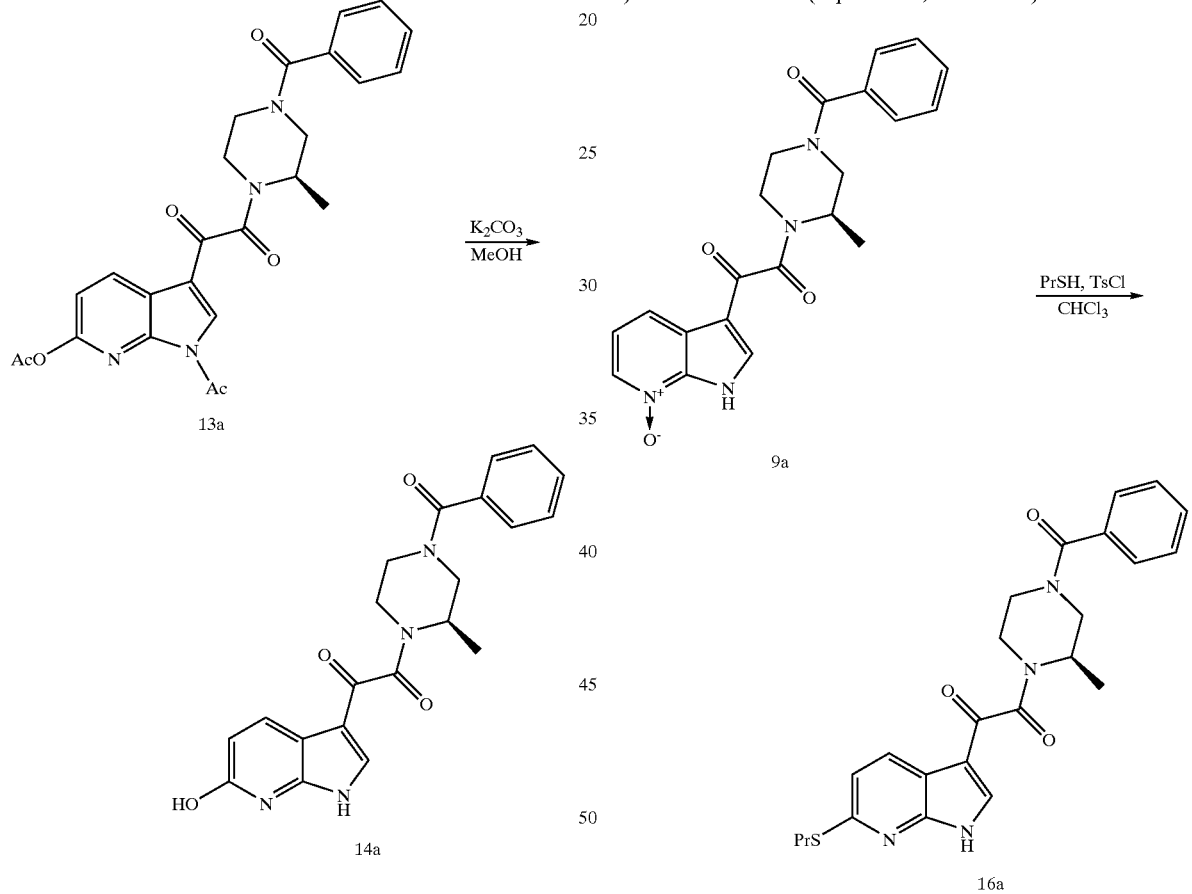

Preparation of (R)-N-(benzoyl)-3-methyl-N'-[(1-acetyl-6-acetoxy-7-azaindol-3-yl)-oxoacetyl]-piperazine 13a: 20 mg of 7-azaindole piperazine diamide N-oxide 8a was dissolved in 5 ml of acetic anhydride (Ac$_2$O). The reaction mixture was heated at reflux for 8 hours. After cooling, the solvents were removed under vacuum to give product 13a, which was pure enough for further reactions.

Characterization of Compound 13a:

Compound 13a, (R)-N-(benzoyl)-3-methyl-N'-[(1-acetyl-6-acetoxy-7-azaindol-3-yl)-oxoacetyl]-piperazine: $^1$H NMR (300 MHz, acetone-d$_6$) δ 8.67 (m, 2H), 7.47 (s, 5H), 7.27 (d, 1H, J=8.34 Hz), 4.90–2.80 (m, 7H), 2.09 (s, 6H), 1.30 (b, 3H); $^{13}$C NMR (75 MHz, acetone-d$_6$) δ 187.0, 170.8, 169.0, 168.6, 164.9, 155.3, 136.5, 134.7, 134.2, 133.2, 130.0, 129.8, 127.5, 118.9, 115.4, 113.8, 50.3, 45.4, 41.3, 36.3, 25.5, 20.5, 16.0, 14.8. MS m/z: (M+Na)$^+$ calcd for C$_{25}$H$_{24}$N$_4$O$_6$Na: 499.16; found 499.15. HPLC retention time: 1.46 minutes (column B).

Preparation of (R)-N-(benzoyl)-3-methyl-N'-[(6-hydroxyl-7-azaindol-3-yl)-oxoacetyl]-piperazine 14a: The crude compound 13a and an excess of K$_2$CO$_3$ (100 mg) were mixed in MeOH and H$_2$O (1:1). The reaction mixture was stirred for 8 hours. The MeOH was removed under vacuum, the aqueous phase extracted with EtOAc (3×10 ml) and the organic layers combined and concentrated. The crude product was purified using a Shimadzu automated preparative HPLC System to give compound 1 mg of 14a (5% from compound 8a).

Characterization of Compound 14a:

Compound 1 4a, (R)-N-(benzoyl)-3-methyl-N'-[(6-hydroxyl-7-azaindol-3-yl)-oxoacetyl]-piperazine: MS m/z: (M+H)$^+$ calcd for C$_{21}$H$_{21}$N$_4$O$_4$: 393.16; found 393.12. HPLC retention time: 1.13 minutes (column A).

8) Thiol Formation (Equation 7, Scheme 5)

Preparation of (R)-N-(benzoyl)-3-methyl-N'-[(6-propylthio-7-azaindol-3-yl)-oxoacetyl]-piperazine 17f: To an solution of 100 mg of compound 9a in 10 ml of CHCl$_3$ was added TsCl (63 mg), and the solution was stirred for 5 minutes. Then, 2 ml of propylthiol was added and the reaction mixture was stirred for 8 hours. After concentration, the crude product was purified using a Shimadzu automated preparative HPLC System to give compound 1.4 mg of 17f.

Characterization of Compound 17f:

Compound 17f, (R)-N-(benzoyl)-3-methyl-N'-[(6-propylthiol-7-azaindol-3-yl)-oxoacetyl]-piperazine: MS m/z: (M+H)$^+$ calcd for C$_{24}$H$_{27}$N$_4$O$_3$S: 451.18; found 451.09. HPLC retention time: 1.45 minutes (column A).

9) Displacement of Nitro Group (Equation 11, Scheme 6)

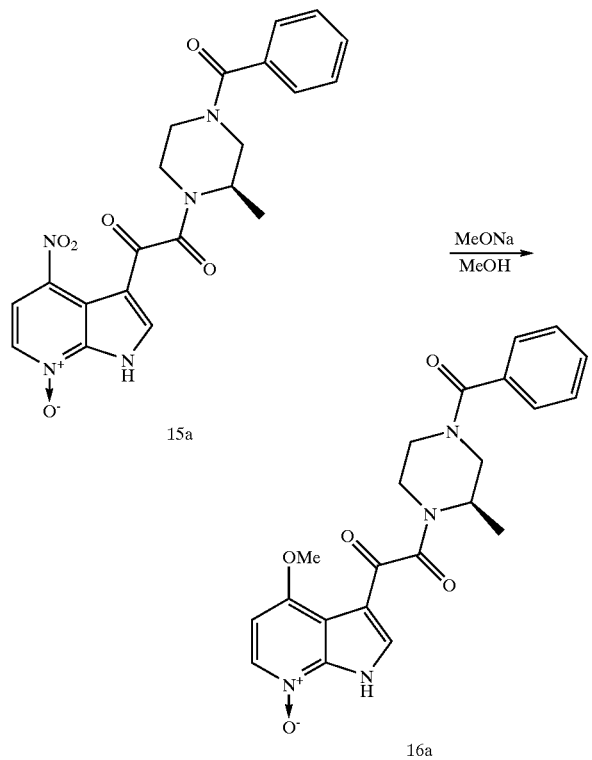

15a

16a

Preparation of (R)-N-(benzoyl)-3-methyl-N'-[(4-methoxy-7-oxide-7-azaindol-3-yl)-oxoacetyl]-piperazine 16a: 100 mg of crude compound 15a from the previous step was dissolved in 6 ml of 0.5M MeONa in MeOH. The reaction mixture was refluxed for 8 hours, and the solvent removed under vacuum to afford a mixture including product 16a and other inorganic salts. This mixture was used in the next step without further purification. A small portion of the crude mixture was purified using a Shimadzu automated preparative HPLC System to give 5 mg of compound 16a.

Characterization of Compounds 16 with the Following Sub-structure:

16

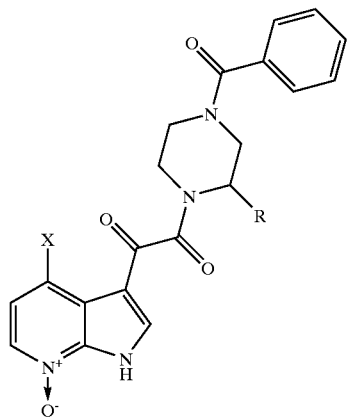

Compound 16a, X=OMe, R=(R)-Me, (R)-N-(benzoyl)-3-methyl-N'-[(4-methoxy-7-oxide-7-azaindol-3-yl)-oxoacetyl]-piperazine: MS m/z: (M+H)$^+$ calcd for $C_{22}H_{23}N_4O_5$ 423.17, found 423.04. HPLC retention time: 0.97 minutes (column A).

Compound 16f, X=OMe, R=(S)-Me, (S)-N-(benzoyl)-3-methylN'-[(4-methoxy-7-oxide-7-azaindol-3-yl)-oxoacetyl]-piperazine: MS m/z: (M+H)$^+$ calcd for $C_{22}H_{23}N_4O_5$ 423.17, found 423.02.

Compound 16g, X=OMe, R=Me, N-(benzoyl)-3-methyl-N'-[(4-methoxy-7-oxide-7-azaindol-3-yl)-oxoacetyl]-piperazine: MS m/z: (M+H)$^+$ calcd for $C_{22}H_{23}N_4O_5$ 423.17, found 423.03.

Compound 16b, X=OCH$_2$CF$_3$, R=(R)-Me, (R)-N-(benzoyl)-3-methyl-N'-[(4-(2,2,2-trifluoroethoxy)-7-oxide-7-azaindol-3-yl)-oxoacetyl]-piperazine: $^1$H NMR (500 MHz, CD$_3$OD) δ 8.44 (b, 1H), 8.30 (m, 1H), 7.50 (b, 5H), 7.14 (b, 1H), 4.90–3.10 (m, 9H), 1.30 (m, 3H). MS m/z: (M+H)$^+$ calcd for $C_{23}H_{22}F_3N_4O_5$: 491.15; found 491.16. HPLC retention time: 1.17 minutes (column A).

Compound 16c, X=OCH(CH$_3$)$_2$, R=(R)-Me, (R)-N-(benzoyl)-3-methyl-N'-[(4-(1-methylethoxy)-7-oxide-7-azaindol-3-yl)-oxoacetyl]-piperazine: $^1$H NMR (500 MHz, CD$_3$OD) δ 8.48 (s, 1H), 8.24 (m, 1H), 7.46 (m, 5H), 7.13 (s, 1H), 5.03–3.00 (m, 8H), 1.49–1.15 (m, 9H). MS m/z: (M+H)$^+$ calcd for $C_{24}H_{27}N_4O_5$: 451.20; found 451.21. HPLC retention time: 1.14 minutes (column A).

Compound 16d, X=OCH$_2$CH$_3$, R=(R)-Me, (R)-N-(benzoyl)-3-methyl-N'-[(4-ethoxy-7-oxide-7-azaindol-3-yl)-oxoacetyl]-piperazine: MS m/z: (M+H)$^+$ calcd for $C_{23}H_{25}N_4O_5$: 437.18; found 437.13. HPLC retention time: 1.08 minutes (column A).

Compound 16e X=SCH$_2$CH$_2$CH$_3$, R=(R)-Me, (R)-N-(benzoyl)3-methyl-N'-[(4-propylthio-7-oxide-7-azaindol-3-yl)-oxoacetyl]-piperazine: $^1$H NMR (500 MHz, CD$_3$OD) δ 8.24 (m, 2H), 7.45 (m, 5H), 7.25 (s, 1H), 4.90–3.00 (m, 9H), 1.81 (b, 2H), 1.30 (m, 6H). MS m/z: (M+H)$^+$ calcd for $C_{24}H_{27}N_4O_4S$: 467.18; found 467.14. HPLC retention time: 1.30 minutes (column A).

Compound 16h, X=NHMe, R=(R)-Me, (R)-N-(benzoyl)-3-methyl-N'-[(4-methylamino-7-oxide-7-azaindol-3-yl)-oxoacetyl]-piperazine: MS m/z: (M+H)$^+$ calcd for $C_{22}H_{24}N_5O_4$: 422.18; found 422.09. HPLC retention time: 1.19 minutes (column A).

10) Reduction of N-Oxide (Equation 12, Scheme 6)

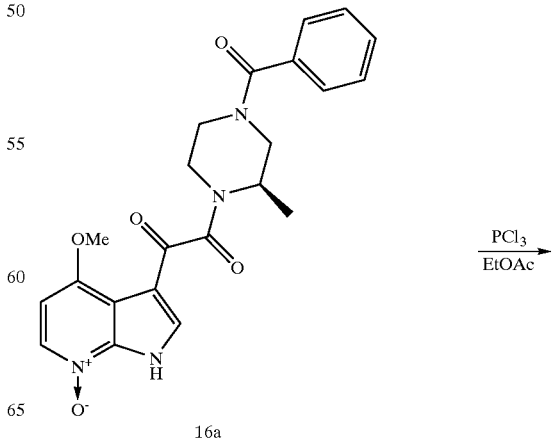

16a

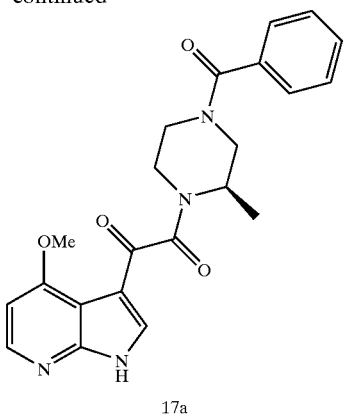

17a

Preparation of (R)-N-(benzoyl)-3-methyl-N'-[(4-methoxy-7-azaindole-3-yl)-oxoacetyl]-piperazine 17a: 48 mg of crude 16a was suspended in 30 ml of ethyl acetate at room temperature. 1 ml of PCl₃ was added and the reaction was mixture stirred for 8 hours. The reaction mixture was poured into ice cooled 2N NaOH solution with caution. After separating the organic layer, the aqueous phase was extracted with EtOAc (6×80 ml). The organic layers were combined, and concentrated in vacuo to give a residue which was purified using a Shimadzu automated preparative HPLC System to give 38 mg of compound 17a.

Characterization of Compounds 17 with the Following Sub-structure:

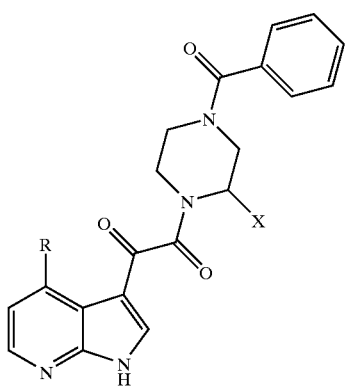

17

Compound 17a, R=Ome, X=(R)-Me, (R)-N-(benzoyl)-3-methyl-N'-[(4-methoxy-7-azaindol-3-yl)-oxoacetyl]-piperazine: $^1$H NMR (300 MHz, CD$_3$OD) δ 8.24 (d, 1H, J=5.7 Hz), 8.21 (m, 1H), 7.47 (s, 5H), 6.90 (d, 1H, J=5.7 Hz), 4.71–3.13 (m, 10H), 1.26 (b, 3H); $^{13}$C NMR (75 MHz, CD$_3$OD) δ 185.3, 172.0, 167.2, 161.2, 150.7, 146.6, 135.5, 134.8, 129.9, 128.3, 126.7, 112.8, 106.9, 100.6, 54.9, 50.2, 48.1, 45.1, 14.5, 13.8. MS m/z: (M+H)$^+$ calcd for C$_{22}$H$_{23}$N$_4$O$_4$: 407.17; found 407.19. HPLC retention time: 1.00 minutes (column A).

Compound 17d, R=Ome, X=(S)-Me, (S)-N-(benzoyl)-3-methyl-N'-[(4-methoxy-7-azaindol-3-yl)-oxoacetyl]-piperazine: MS m/z: (M+H)$^+$ calcd for C$_{22}$H$_{23}$N$_4$O$_4$: 407.17; found 407.03.

Compound 17e, R=Ome, X=Me, N-(berizoyl)-3-methyl-N'-[(4-methoxy-7-azaindol-3-yl)-oxoacetyl]-piperazine: MS m/z: (M+H)$^+$ calcd for C$_{22}$H$_{23}$N$_4$O$_4$: 407.17; found 407.03.

Compound 17b, R=OCH$_2$CF$_3$, X=(R)-Me, (R)-N-(benzoyl)-3-methyl-N'-[(4-(2,2,2-trifluoroethoxy)-7-azaindol-3-yl)-oxoacetyl]-piperazine: $^1$H NMR (500 MHz, CD$_3$OD) δ 8.33 (s, 1H), 8.19 (m, 1H), 7.45 (m, 5H), 7.05 (s, 1H), 4.90–3.00 (m, 9H), 1.29 (b, 3H); $^{13}$C NMR (125 MHz, CD$_3$OD) δ 185.7, 174.0, 168.3, 162.0, 151.0, 146.1, 138.5, 136.4, 131.4, 130.0, 128.2, 114.8, 109.5, 103.6, 67.2, 66.9, 52.0, 47.0, 16.4, 15.3. MS m/z: (M+H)$^+$ calcd for C$_{23}$H$_{22}$F$_3$N$_4$O$_4$: 475.16; found 475.23. HPLC retention time: 1.22 minutes (column A).

Compound 17c, R=OCH(CH$_3$)$_2$, X=(R)-Me, (R)-N-(benzoyl)-3-methyl-N'-[(4-(1-methylethoxy)-7-azaindol-3-yl)-oxoacetyl]-piperazine: $^1$H NMR (500 MHz, CD$_3$OD) δ 8.42 (s, 1H), 8.24 (m, 1H), 7.47 (m, 5H), 7.21 (s, 1H), 5.20–3.00 (m, 8H), 1.51 (b, 6H), 1.22 (b, 3H); $^{13}$C NMR (125 MHz, CD$_3$OD) δ 185.4, 173.6, 167.9, 166.1, 145.3, 141.4, 138.2, 136.4, 131.5, 129.7, 128.2, 113.9, 111.4, 104.0, 75.5. 54.4, 53.7, 51.8, 46.9, 22.1, 16.4, 15.3. MS m/z: (M+H)$^+$ calcd for C$_{24}$H$_{27}$N$_4$O$_4$: 435.20; found 435.20. HPLC retention time: 1.15 minutes (column A).

Compound 17m, R=OCH$_2$CH$_3$, X=(R)-Me, (R)-N-(benzoyl)-3-methyl-N'-[(4-ethoxy-7-azaindol-3-yl)-oxoacetyl]-piperazine: MS m/z: (M+H)$^+$ calcd for C$_{23}$H$_{25}$N$_4$O$_4$: 421.19; found 421.13. HPLC retention time: 1.13 minutes (column A).

Compound 17g, R=SCH$_2$CH$_2$CH$_3$, X=(R)-Me, (R)-N-(benzoyl)-3-methyl-N'-[(4-propylthio-7-azaindol-3-yl)-oxoacetyl]-piperazine: MS m/z: (M+H)$^+$ calcd for C$_{24}$H$_{27}$N$_4$O$_4$S: 451.18; found 451.13. HPLC retention time: 1.50 minutes (column A).

Compound 17h, R=NHMe, X=(R)-Me, (R)-N-(benzoyl)-3-methyl-N'-[(4-methylamino-7-azaindol-3-yl)-oxoacetyl]-piperazine: MS m/z: (M+H)$^+$ calcd for C$_{22}$H$_{24}$N$_5$O$_3$: 406.19; found 406.03. HPLC retention time: 1.19 minutes (column A).

Characterization of Compound 18a

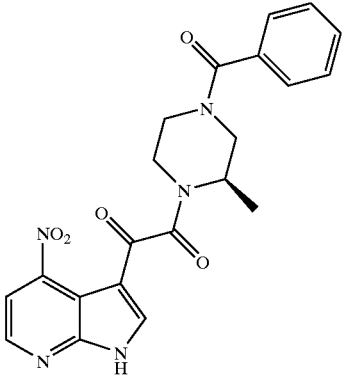

18a

Compound 18a, (R)-N-(benzoyl)-3-methyl-N'-[(4-nitro-7-azaindol-3-yl)-oxoacetyl]-piperazine: $^1$H NMR (300 MHz, CD$_3$OD) δ 8.58 (s, 1H), 8.53 (m, 1H), 7.64 (s, 1H), 7.47 (s, 5H), 4.90–3.00 (m, 7H), 1.30 (b, 3H); $^{13}$C NMR (75 MHz, CD$_3$OD) δ 184.1, 172.1, 165.6, 151.9, 149.6, 145.5, 139.4, 134.8, 129.7, 128.4, 126.7, 111.6, 111.2, 107.4, 53.7, 48.4, 45.9, 15.0, 13.7. MS m/z: (M+H)$^+$ calcd for C$_{21}$H$_{20}$N$_5$O$_5$: 422.15; found 422.09. HPLC retention time: 1.49 minutes (column B).

11) Reduction of Nitro to Hydoxylamine Group (Equation 14, Scheme 6)

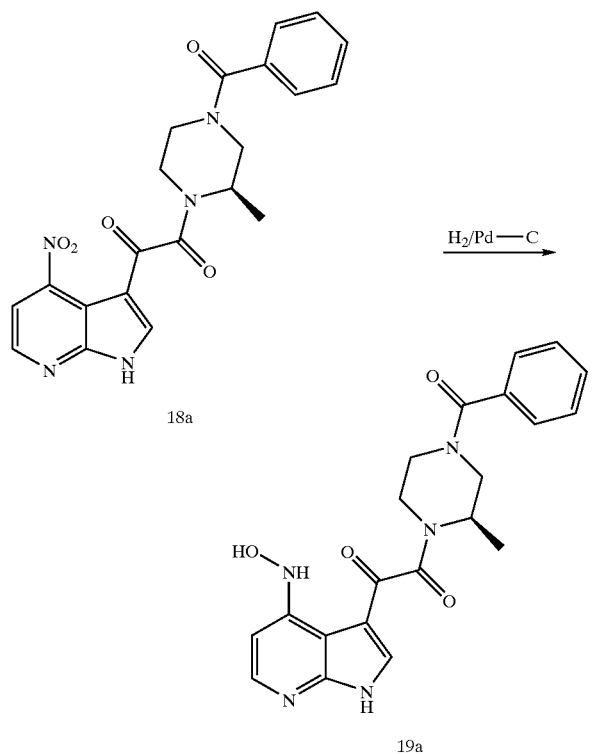

Preparation of (R)-N-(benzoyl)-3-methyl-N'-[(4-hydroxylamino-7-azaindole-3-yl)-oxoacetyl]-piperazine 19a: 10 mg of Pd (10% on activated carbon) was added to a solution of compound 18a (48 mg, 0.11 mmol) in methanol (10 ml) under an atmosphere of hydrogen. The reaction mixture was stirred for 8 hours at room temperature. After filtration, the filtrate was concentrated in vacuo to give a residue which was purified using a Shimadzu automated preparative HPLC System to give compound 19a (7.9 mg, 17%).

Characterization of Compound 19a:

Compound 19a, (R)-N-(benzoyl)-3-methyl-N'-[(4-hydroxylamino-7-azaindol-3-yl)-oxoacetyl]-piperazine: MS m/z: (M+H)$^+$ calcd for $C_{21}H_{22}N_5O_4$: 408.17; found 408.21. HPLC retention time: 1.03 minutes (column A).

12) Reduction of Nitro to Amine Group (Equation 15, Scheme 6)

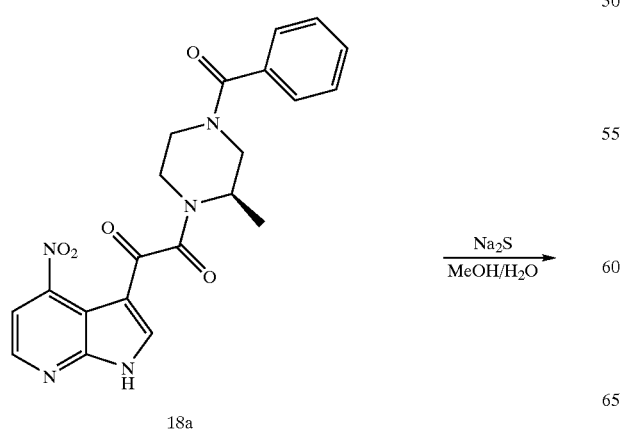

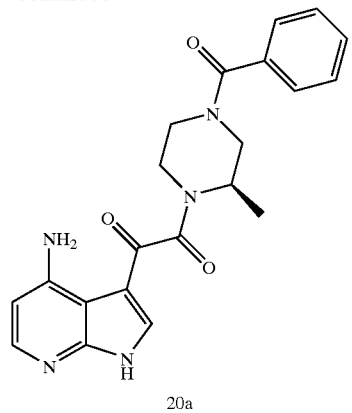

Preparation of (R)-N-(benzoyl)-3-methyl-N'-[(4-amino-7-azaindol-3-yl)-oxoacetyl]-piperazine 20a: 114 mg of Na$_2$S.2H$_2$O (1 mmol) was added to a solution of compound 18a (20 mg, 0.048 mmol) in MeOH (5 ml) and H$_2$O (5 ml). The reaction mixture was heated at reflux for 8 hours. After cooling, the reaction mixture was concentrated in vacuo to give a residue which was purified using a Shimadzu automated preparative HPLC System to give 4 mg of compound 20a (21.3%).

Characterization of Compound 20a:

Compound 20a, (R)-N-(benzoyl)-3-methyl-N'-[(4-amino-7-azaindol-3-yl)-oxoacetyl]-piperazine: $^1$H NMR (500 MHz, CD$_3$OD) δ 8.16 (m, 1H), 8.01(d, 1H, J=8.1 Hz), 7.47 (m, 5H), 6.66 (s, 1H), 4.90–3.00 (m, 7H), 1.30 (b, 3H). MS m/z: (M+H)$^+$ calcd for $C_{21}H_{22}N_5O_3$: 392.17; found 392.14. HPLC retention time: 0.96 minutes (column A).

13) Alkylation of the Nitrogen Atom at Position 1 (Equation 16, Scheme 7)

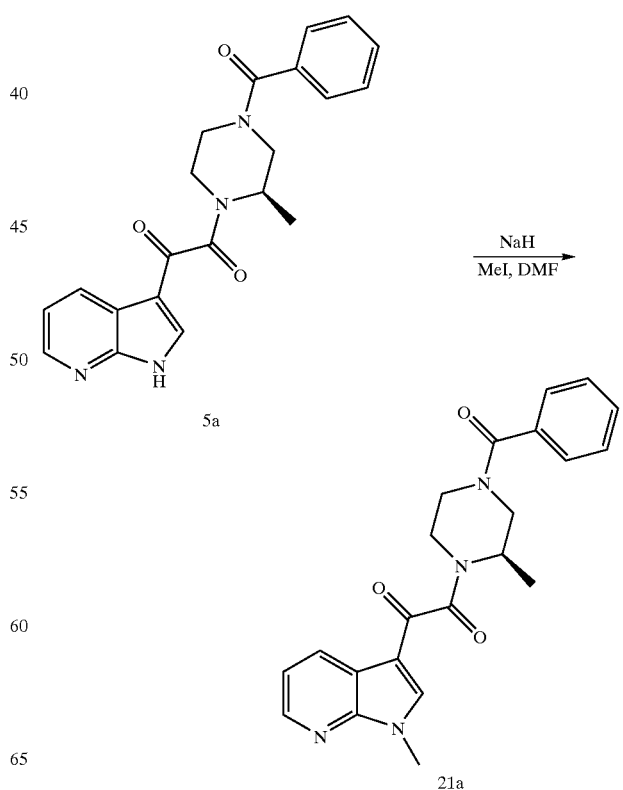

Preparation of (R)-N-(benzoyl)-3-methyl-N'-[(1-methyl-7-azaindol-3-yl)-oxoacetyl]-piperazine 21a: NaH (2 mg, 60% pure, 0.05 mmol) was added to a solution of compound 5a (10 mg, 0.027 mmol) in DMF. After 30 minutes, MeI (5 mg, 0.035 mmol) was injected into the mixture via syringe. The reaction mixture was stirred for 8 hours at room temperature and quenched with methanol. The mixture was partitioned between ethyl acetate (2 ml) and $H_2O$ (2 ml). The aqueous phase was extracted with EtOAc (3×2 ml). The organic layers were combined, dried over anhydrous $MgSO_4$ and concentrated in vacuo to give a crude product which was purified using a Shimadzu automated preparative HPLC System to give compound 21a (2.5 mg, 24%).

Characterization of compound 21 with the following sub-structure:

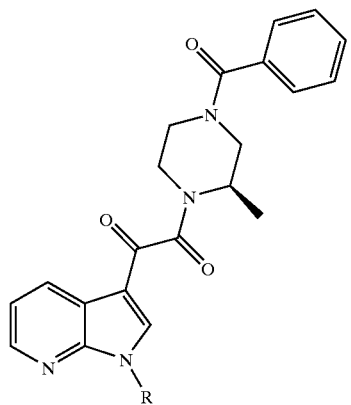

21

Compound 21a, R=Me, (R)-N-(benzoyl)-3-methyl-N'-[(1-methyl-7-azaindol-3-yl)-oxoacetyl]-piperazine: $^1$H NMR (500 MHz, $CD_3OD$) δ 8.56 (b, 1H), 8.42 (s, 1H), 8.30 (m, 1H), 7.47 (m, 6H), 4.90–3.00 (m, 7H), 3.96 (s, 3H), 1.28 (b, 3H). MS m/z: $(M+Na)^+$ calcd for $C_{22}H_{22}N_4O_3Na$: 413.16; found 413.15. HPLC retention time: 1.47 minutes (column B).

Compound 21b, R=$CH_2$—CH=$CH_2$, (R)-N-(benzoyl)-3-methyl-N'-[(1-allyl-7-azaindol-3-yl)-oxoacetyl]-piperazine: $^1$H NMR (500 MHz, $CD_3OD$) δ 8.37 (m, 3H), 7.44 (m, 6H), 6.08 (m, 1H), 5.22–3.06 (m, 11H), 1.27 (m, 3H); $^{13}$C NMR (75 MHz, $CD_3OD$) δ 184.2, 184.1, 170.8, 165.0, 146.7, 143.5, 137.9, 133.8, 131.4, 129.2, 128.8, 127.3, 125.6, 117.9, 117.4, 116.3, 110.3, 50.4, 49.7, 49.1, 45.7, 44.0, 41.0, 39.6, 34.8, 14.0, 12.8, . MS m/z: $(M+H)^+$ calcd for $C_{24}H_{25}N_4O_3$: 417.19; found 417.11. HPLC retention time: 1.43 minutes (column A).

14) Group Transfer Reactions from Halide (Equation 18, Scheme 8)

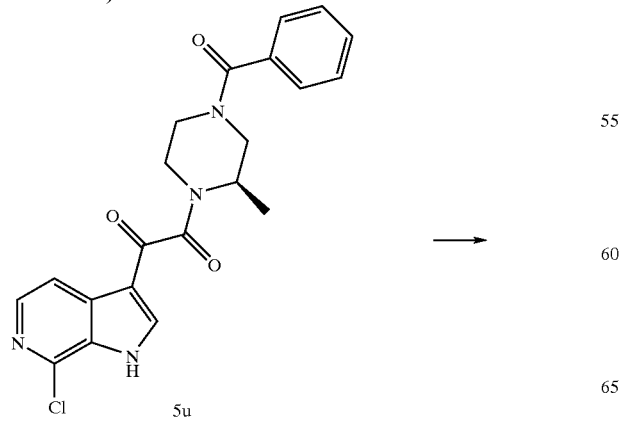

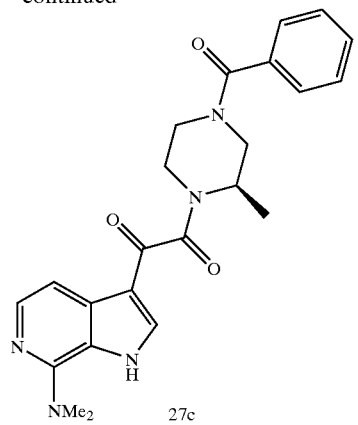

27c

Preparation of (R)-N-(benzoyl)-3-methyl-N'-[(7-dimethylamino-6-azaindol-3-yl)-oxoacetyl]-piperazine 27c: A mixture of compound 5u (50 mg) and 4 ml of dimethylamine (40% in water) was heated to 150° C. in sealed tube for 18 hours. The solvents were then removed under vaccum and the residue was purified using Shimadzu automated preparative HPLC System to give 10 mg of compound 27c.

Characterization of Compound 27c:
Compound 27c, (R)-N-(benzoyl)-3-methyl-N'-[(7-dimethylamino-6-azaindol-3-yl)-oxoacetyl]-piperazine: MS m/z: $(M+H)^+$ calcd for $C_{23}H_{26}N_5O_3$ 420.20, found 420.16. HPLC retention time: 1.13 minutes (column A).

15) Modification of Benzoyl Moiety (Equation 26, Schem 11)

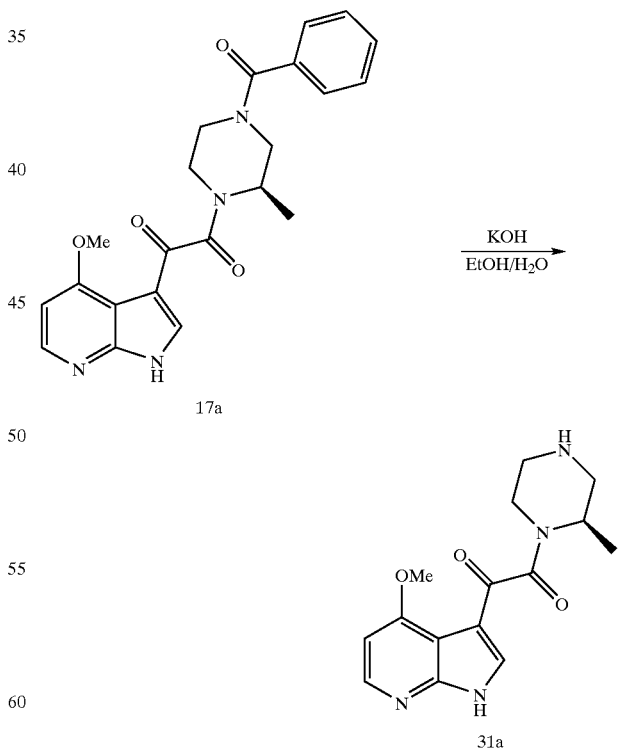

Hydrolysis of benzoyl amide, preparation of (R)-2-methyl-N-[(4-methoxy-7-azaindol-3-yl)-oxoacetyl]-piperazine 31a: Compound 17a (0.9 g) and KOH (2.0 g) were mixed in a solution of EtOH (15 ml) and water (15 ml).

The reaction was refluxed for 48 hours. Solvents were removed under vaccum and the resulting residue was purified by silica gel column chromatography (EtOAc/Et$_3$N= 100:1 to 3:1) to afford 0.6 g of compound 31a.

Characterization of Compound 31a:

Compound 31a, (R)-2-methyl-N-[(4-methoxy-7-azaindol-3-yl)-oxoacetyl]-piperazine: MS m/z: (M+H)$^+$ calcd for C$_{15}$H$_{19}$N$_4$O$_3$ 303.15, found 303.09. HPLC retention time: 0.29 minutes (column A).

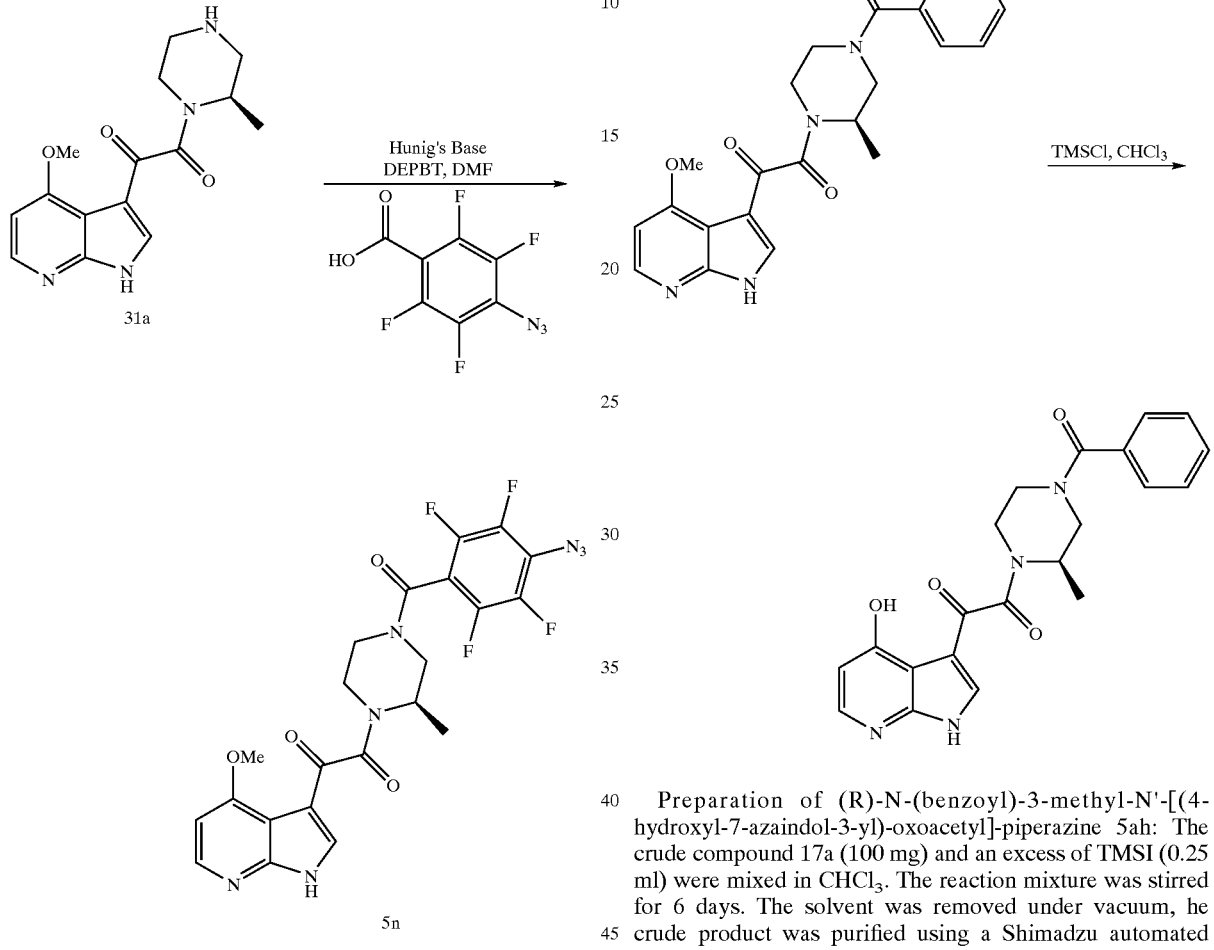

Diamide formation: Preparation of (R)-N-(4-azido-2,3,5,6-tetra-fluorobenzoyl)-3-methyl-N'-[(4-methoxy-7-azaindol-3-yl)-oxoacetyl]-piperazine 5n: Amine 31a (0.15 g), 4-azido-2,3,5,6-tetrafluorobenzoic acid (0.12 g), 3-(diethoxyphosphoryloxy)-1,2,3-benzotriazin-4(3H)-one (DEPBT) (0.15 g) and Hunig's Base (0.5 ml) were combined in 5 ml of DMF. The mixture was stirred at room temperature for 8 hours. Solvents were then removed under vaccum and the residue was purified using Shimadzu automated preparative HPLC System to give 10 mg of compound 5n.

Characterization of Compound 5n:

Compound 5n, (R)-N-(4-azido-2,3,5,6-tetra-fluorobenzoyl)-3-methyl-N'-[(4-methoxy-7-azaindol-3-yl)-oxoacetyl]-piperazine: MS m/z: (M+H)$^+$ calcd for C$_{22}$H$_{18}$F$_4$N$_7$O$_4$ 520.14, found 520.05. HPLC retention time: 1.42 minutes (column A).

Compound 5af, Ar=4,5-dibromophenyl, (R)-N-(3,5-dibromobenzyl)-3-methyl-N'-[(4-methoxy-7-azaindol-3-yl)-oxoacetyl]-piperazine: MS m/z. (M+H)$^+$ calcd for C$_{22}$H$_{21}$Br$_2$N$_4$O$_4$ 562.99, found 562.99. HPLC retention time: 1.54 minutes (column A).

Compound 5ag, Ar=4-[3-(trifluoromethyl)-3H-diazirin-3-yl]phenyl, (R)-N-[4-(3-(trifluoromethyl)-3H-diazirin-3-yl)benzyl]-3-methyl-N'-[(4-methoxy-7-azaindol-3-yl)-oxoacetyl]-piperazine: MS m/z: (M+H)$^+$ calcd for C$_{24}$H$_{22}$F$_3$N$_6$O$_4$ 515.17, found 515.02. HPLC retention time: 1.55 minutes (column A).

New Equation:

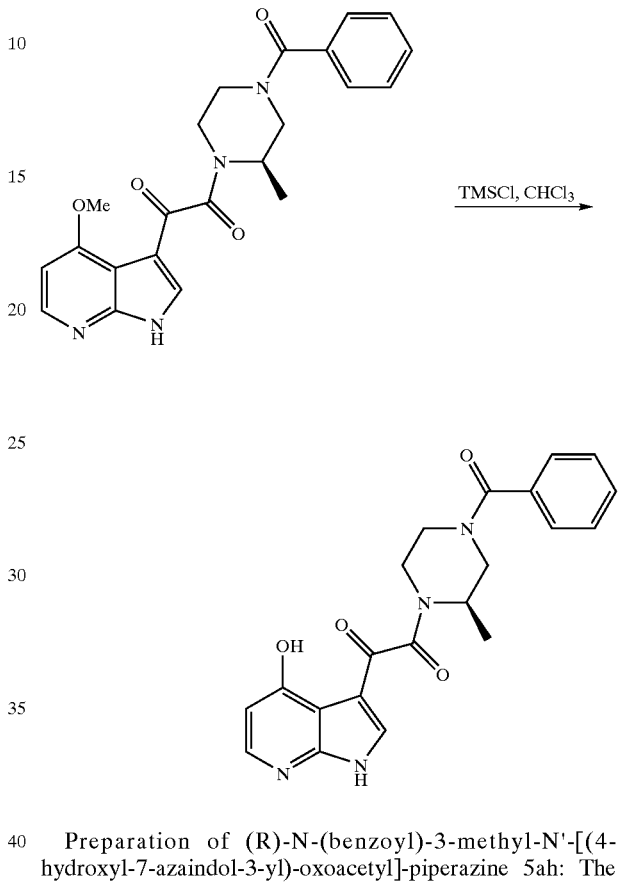

Preparation of (R)-N-(benzoyl)-3-methyl-N'-[(4-hydroxyl-7-azaindol-3-yl)-oxoacetyl]-piperazine 5ah: The crude compound 17a (100 mg) and an excess of TMSI (0.25 ml) were mixed in CHCl$_3$. The reaction mixture was stirred for 6 days. The solvent was removed under vacuum, he crude product was purified using a Shimadzu automated preparative HPLC System to give compound 4.4 mg of 5ah.

Characterization of Compound 5ah:

Compound 5ah, (R)-N-(benzoyl)-3-methyl-N'-[(4-hydroxyl-7-azaindol-3-yl)-oxoacetyl]-piperazine: MS m/z: (M+H)$^+$ calcd for C$_{21}$H$_{21}$N$_4$O$_4$: 393.16; found 393.11. HPLC retention time: 1.46 minutes (column B).

Alternate Procedures Useful for the Synthesis of Compound 39

Preparation of 5,7-dibromo-4-methoxy-6-azaindole 36; Vinylmagnesium bromide (0.85 M in THF, 97.7 mL, 83.0 mmol) was added over 30 min. to a stirring solution of 2,6-dibromo-3-methoxy-5-nitropyridine (7.4 g, 23.7 mmol) in THF (160 mL) at −75° C. The sol tion was stirred 1 h at −75° C., overnight at −20° C. recooled to −75° C. and quenched with saturated aqueous NH$_4$Cl (~100 mL). The reaction mixture was allowed to warm to rt, washed with brine (~100 mL) and extracted with Et$_2$O (150 mL) and CH$_2$Cl$_2$ (2×100 mL). The combined organi were dried (MgSO$_4$), filtered and concentrated. The residue was purified by flash column chromatography (SiO$_2$, 3:1 hexanes/ EtOAc) to yield 5,7-dibromo-4-methoxy-6-azaindole 36 (1.10 g, 3.60 mmol, 15%) as a pale yellow solid.

Characterization of 36: $^1$H NMR (500 MHz, CDCl$_3$) δ 8.73 (br s, 1H), 7.41 (dd, J=3.1, 2.8 Hz, 1H), 6.69 (d, J=3.1, 2.2 Hz, 1H), 4.13 (s, 3H); $^{13}$C NMR (125 MHz, CDCl$_3$) δ 146.6, 133.7, 128.8, 127.5, 120.2, 115.6, 101.9, 60.7. MS m/z (M+H)$^+$ calcd for C$_8$H$_7$Br$_2$N$_2$O: 304.88; found 304.88. HPLC retention time: 1.31 minutes (column A).

Preparation of 4-methoxy-6-azaindole 37; A solution of 5,7-Dibromo-4-methoxy-6-azaindole 36 (680 mg, 2.22 mmol), 5% Pd/C (350 mg, 0.17 mmol) and hydrazine (2.5 mL, 80 mmol) in EtOH was heated at reflux for 1 h. The reaction mixture was allowed to cool t rt, filtered through celite and the filtrate concentrated. Aqueous NH$_4$OH (11% in H$_2$O, 45 mL) was added to the residue and the solution was extracted with CH$_2$Cl$_2$ (3×30 mL). The combined o anics were dried (MgSO$_4$), filtered and concentrated to yield 4-methoxy-6-azaindole 37 (290 mg, 1.95 mmol, 88%) as an orange solid.

Characterization of 37: $^1$H NMR (500 MHz, CDCl$_3$) δ 8.61 (br s, 1H), 8.52 (s, 1H), 7.88 (s, 1H), 7.30 (d, J=2.9 Hz, 1H), 6.69 (d, J=2.9 Hz, 1H), 4.03 (s, 3H). MS m/z (M+H)$^+$ calcd for C$_8$H$_9$N$_2$O: 149.06; found 148.99. HPLC retention time: 0.61 minutes (column A).

Preparation of 38: Aluminum trichloride (67 mg, 0.50 mmol) was added to a solution of 4-methoxy-6-azaindole (15 mg, 0.10 mmol) in CH$_2$Cl$_2$ (2 mL) and stirred at rt for 30 min. Methyl chlorooxacetate (0.020 mL, 0.21 mmol) was added and the reaction mixture was stirred overnight. The reaction was quenched with MeOH (0.20 mL), stirred 5 h and filtered (flushing with CH$_2$Cl$_2$). The filtrate was washed with saturated aqueous NH$_4$OAc (2×10 mL) and H$_2$O (10 mL) and concentrated to yield 38 (5 mg) as a yellow solid.

Characterization of 38: $^1$H NMR (500 MHz, CDCl$_3$) δ 8.65 (s, 1H), 8.36 (s, 1H), 8.02 (s, 1H), 4.03 (s, 3H), 3.96 (s, 3H). MS m/z (M+H)$^+$ calcd for C$_{11}$H$_{10}$N$_2$O$_4$: 235.06; found 234.96. HPLC retention time: 0.63 minutes (column A).

Preparation of N-benzoyl-N'-[(2-carboxaldehyde-pyrrole-4-yl)-oxoacetyl]-piperazine 41: A solution of ethyl 4-oxoacetyl-2-pyrrolecarboxaldehyde 40 (17.0 g, 87.1 mmol) in 25 mL of KOH (3.56 M in H$_2$O, 88.8 mmol) and EtOH (400 mL) was stirred 2 h. The white precipitate that formed was collected by filtration, washed with EtOH (~30 mL) and Et$_2$O (~30 mL) and dried under high vacuum to yield 15.9 g of potassium 2-pyrrolecarboxaldehyde-4-oxoacetate as a white solid that was used without further purification. A solution of potassium 2-pyrrolecarboxaldehyde-4-oxoacetate (3.96 g, 19.3 mmol), N-benzoyliperazine hydrochloride (4.54 g, 19.7 mmol), 3-(diethoxyphosphoryloxy)-1,2,3-benzotriazin-4(3H)-one (5.88 g, 19.7 mmol) and triethylamine (3.2 mL, 23 mmol) in DMF (50 mL) was stirred 1d. The reaction mixture was filtered into H$_2$O (300 mL), extracted with CH$_2$Cl$_2$ (3×200 mL) and the combined organics were concentrated on a rotary evaporator to remove the CH$_2$Cl$_2$. The crude material (still in DMF) was then diluted with H$_2$O (200 mL) and allowed to recrystallize for 48 h. The solid was then collected by filtration and dried under high vacuum (P$_2$O$_5$) to yield N-benzoyl-N'-[(2-carboxaldehyde-pyrrole-4-yl)-oxoacetyl]-piperazine 41 (3.3 g, 9.7 mmol, 45% over two steps) as a light yellow solid. No further purification was required.

Characterization of 41: $^1$H NMR (500 MHz, CDCl$_3$) δ 9.79 (s, 1H), 9.63 (s, 1H), 7.82 (s, 1H), 7.51–7.34 (m, 6H), 4.05–3.35 (m, 8H). MS m/z (M+H)$^+$ calcd for C$_{18}$H$_{18}$N$_3$O$_4$: 340.12; found 340.11. HPLC retention time: 1.04 minutes (column A).

Preparation of 42: N-benzoyl-N'-[(2-carboxaldehyde-pyrrole-4-yl)-oxoacetyl]-piperazine 41 (3.3 g, 9.7 mmol) was stirred as a slurry in EtOH (100 mL) for 15 min., cooled to 0° C. and then reacted with glycine methyl ester hydrochloride (3.66 g, 29.2 mmol), triethylamine (1.50 mL, 11 mmol) and sodium cyanoborohydride (672 mg, 10.7 mmol). The reaction mixture was allowed to warm to rt, stirred 24 h and poured into ice (~400 mL). The solution was extracted with EtOAc (3×300 mL) and the combined organics were washed with brine (300 mL), dried (MgSO$_4$) and concentrated under reduced pressure. The residue was purified by preparative thin layer chromatography (SiO$_2$, 9:1 EtOAc/MeOH, R$_f$=0.2) to yield 42 (2.4 g, 5.8 mmol, 60%) as a white solid.

Characterization of 42: $^1$H NMR (500 MHz, CDCl$_3$) δ 9.33 (s, 1H), 7.49 (s, 1H), 7.58–7.32 (m, 5H), 6.50 (s, 1H), 3.90–3.35 (m, 8H), 3.81 (s, 2H), 3.74 (s, 3H), 3.40 (s, 2H). MS m/z (M+H)$^+$ calcd for C$_{21}$H$_{25}$N$_4$O$_5$: 413.17; found 413.17. HPLC retention time: 0.84 minutes (column A).

Preparation of 43: Methyl ester 42 (485 mg, 1.17 mmol) and K$_2$CO$_3$ (325 mg, 2.35 mmol) in MeOH (6 mL) and H$_2$O (6 mL) were stirred at rt for 3 h. The reaction mixture was then quenched with concentrated HCl (0.40 mL) and concentrated under high vacuum. Part of the solid residue (200 mg, 0.37 mmol) was added to a stirring solution of P$_2$O$_5$ (400 mg, 1.4 mmol) in methanesulfonic acid (4.0 g, 42 mmol) (which had already been stirred together at 110° C. for 45 min.) at 110° C. and stirred for 15 min. The reaction mixture was poured over crushed ice (~20 g), stirred 1 h, basified with K$_2$CO$_3$ (5.0 g, 38 mmol), diluted with CH$_2$Cl$_2$ (20 mL), and benzoyl chloride (1.0 mL, 8.5 mmol) and stirred 1 h. The reaction mixture was extracted with CH$_2$Cl$_2$ (3×20 mL) and the combined organics were dried (Na$_2$SO$_4$) and concentrated under reduced pressure. The residue was purified by preparative thin layer chromatography (SiO$_2$, EtOAc, R$_f$=0.5) to yield 43 (101 mg g, 0.21 mmol, 57%) as an off white solid.

Characterization of 43: MS m/z (M+H)$^+$ calcd for C$_{27}$H$_{24}$N$_4$O$_5$: 485.17; found 485.07. HPLC retention time: 1.15 minutes (column A).

Preparation of 39. R=OMe, N-(benzoyl)-N'-[(4-methoxy-6-azaindole-3-yl)-oxoacetyl]-piperazine:

In a flask affixed with a Dean-Stark trap, p-toluenesulfonic acid hydrate (55 mg, 0.29 mmol) and benzene (5 mL) were heated to reflux for 1 h. The solution was cooled to rt and reacted with 2,2-dimehoxypropane (0.10 mL, 0.81 mmol) and 43 (46 mg, 0.095 mmol). The reaction mixture was stirred 1 h, diluted with CH$_2$Cl$_2$ (2 mL), stirred 30 min. and then oxidized with tetrachlorobenzoquinone (150 mg, 0.61 mmol) and stirred overnight. The reaction mixture was poured into 5% aqueous NaOH (20 mL) and extracted with CH$_2$Cl$_2$ (3×25 mL). The combined organics were dried (Na$_2$SO$_4$) and concentrated under reduced pressure. The residue was subjected to preparative thin layer chromatography (Et$_2$O), the baseline material was extracted and resubjected to preparative thin layer chromatography (SiO$_2$, 9:1 EtOAc/MeOH, R$_f$=0.15) to yield 39 (3 mg, 0.008 mmol, 6%) as a white solid.

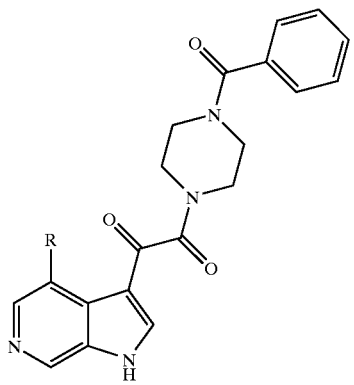

Compound 39, R=OMe, N-(benzoyl)-3-methyl-N'-[(4-methoxy-6-azaindol-3-yl)-oxoacetyl]-piperazine:

Characterization of 39: $^1$H NMR (500 MHz, CD$_3$OD) δ 8.49 (s, 1H), 8.35 (s, 1H), 7.98 (s, 1H), 7.53–7.38 (m, 5H), 4.02 (s, 3H), 3.97–3.42 (m, 8H). MS m/z(M+H)$^+$ calcd for C$_{21}$H$_{23}$N$_4$O$_5$: 393.15; found 393.13. HPLC retention time: 0.85 minutes (column A).

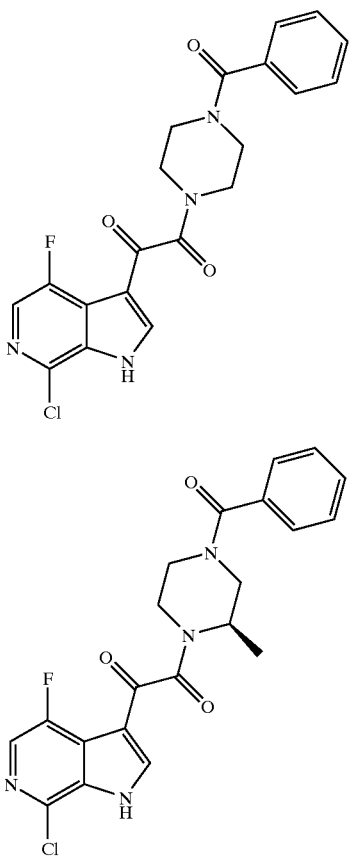

Preparation of 5av N-(benzoyl)-N'-[(4-fluoro-7-chloro-6-azaindol-3-yl)-oxoacetyl]-piperazine and 5 av'(R)-N-(benzoyl)-3-methyl-N'-[(4-fluoro-7-chloro-6-azaindol-3-yi)-oxoacetyl]-piperazine It should be noted that 2-chloro-5-fluoro-3-nitro pyridine may be prepared by the method in example 5B of reference 59 Marfat et.al. The scheme below provides some details which enhance the yields of this route. The Bartoli chemistry in Scheme 1 was used to prepare the aza indole 1zz which is also detailed below.

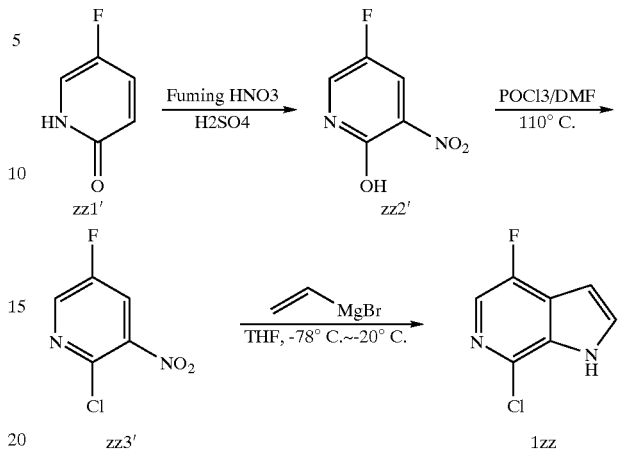

Compound zz1' (1.2 g, 0.01 mol) was dissolved in 2.7 ml of sulphuric acid at room temperature. Premixed fuming nitric acid (1 ml) and sulphuric acid was added dropwise at 5–10° C. to the solution of compound zz1'. The reaction mixture was heated to 85° C. for 1 hr, then cooled to room temperature and poured into ice (20 g). The yellow solid product zz2' was collected by filtration, washed with water and dried in air to yield 1.01 g of compound zz2'.

Compound zz2' (500 mg, 3.16 mmol) was dissolved in Phosphorus oxychloride (1.7 ml, 18.9 mmol) and DMF (Cat) at room temperature. The reaction was heated to 110° C. for 5 hr. The excess POCl3 was removed in vacuo. The residue was chromatographed on silica gel (CHCl3, 100%) to afford 176 mg of product zz3'.

Compound zz3' (140 mg, 0.79 mmol) was dissolved in THF (5 ml) and cooled to -78° C. under N2. Vinyl magnesium bromide (1.0M in ether, 1.2 ml) was added dropwise. After the addition was completed, the reaction mixture was kept at -20° C. for about 15 hr. The reaction was then quenched with saturated NH4Cl, extracted with EtOAc. The combined organic layer was washed with brine, dried over MgSO4, concentrated and chromatographed to afford about 130 mg of compound 1zz.

The chemistry in Scheme 3 provided the derivatives which corresponds to general formula 5 and has a 6-aza ring and R$_2$=F and R$_4$=Cl. In particular, reaction of 2-chloro-5-fluoro-3-nitro pyridine with 3 equivalents of vinyl Magnesium bromide using the typical conditions described herein will provide 4-fluoro-7-chloro-6-azaindole in high yield. Addition of this compound to a solution of aluminum trichloride in dichloromethane stirring at ambident temperature followed 30 minutes later with chloromethyl or chloroethyl oxalate provided an ester. Hydrolysis with KOH as in the standard procedures herein provided an acid salt which reacted with piperazines 4 (for example 1-benzoyl piperazine) in the presence of DEPBT under the standard conditions described herein to provide the compound 5 described just above. The compound with the benzoyl piperazine is N-(benzoyl)-N'-[(4-fluoro-7-chloro-6-azaindol-3-yl)-oxoacetyl]-piperazine and is compound 5av. The compound with the (R)-methyl benzoyl piperazine is 5 av'(R)-N-(benzoyl)-3-methyl-N'-[(4-fluoro-7-chloro-6-azaindol-3-yl)-oxoacetyl]-piperazine and is compound 5av'

Characterization of 5av N-(benzoyl)-N'-[(4-fluoro-7-chloro-6-azaindole-3-yl)-oxoacetyl]-piperazine and 5 av' (R)-N-(benzoyl)-3-methyl-N'-[(4-fluoro-7-chloro-6-azaindol-3-yl)-oxoacetyl]-piperazine

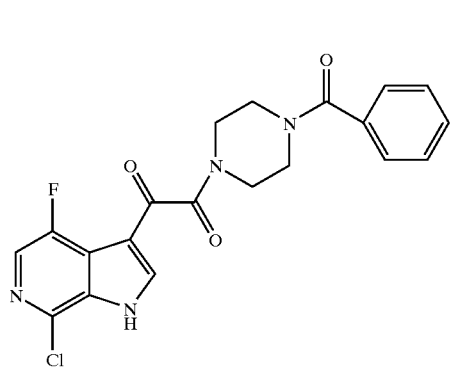

5av $^1$H NMR (500 MHz, CD3OD): 8.40 (s, 1H), 8.04 (s, 1H), 7.46 (bs, 5H), 3.80~3.50 (m, 8H).
LC/MS: (ES+) m/z (M+H)$^+$=415, RT=1.247.

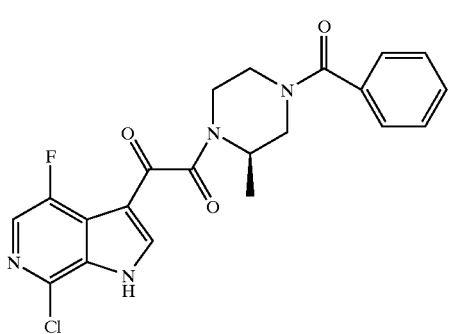

5av'

$^1$H NMR (500 MHz, CD3OD): 8.42 (s, 1/2H), 8.37 (s, 1/2H), 8.03 (s, 1H), 7.71~7.45 (m, 5H), 4.72~3.05 (m, 7H), 1.45~1.28 (m, 3H).
LC/MS: (ES+) m/z (M+H)$^+$=429, RT=1.297.
LC/MS Column: YMC ODS-A C18 S7 3.0×50 mm. Start % B=0, Final % B=100, Gradient Time=2 mln, Flow rate=5 ml/min. Wavelength=220 nm. Solvent A=10% MeOH—90% H2O—0.1% TFA. Solvent B=90% MeOH—10% H2O—0.1% TFA.

Similarly compounds 5ay, 5az, 5abc and 5abd can be made:

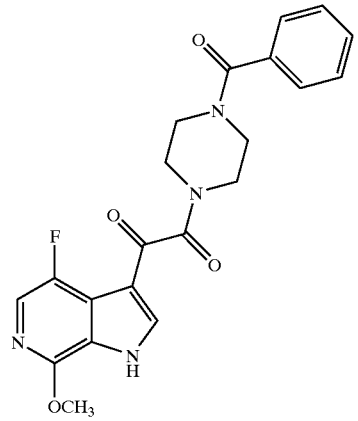

5ay

5ay N-(benzoyl)-N'-[(4-fluoro-7-methoxy-6-azaindol-3-yl)-oxoacetyl]-piperazine

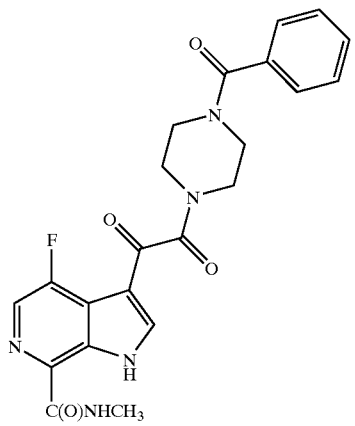

5az

5az N-(benzoyl)-N'-[(4-fluoro-7-(N-methyl-carboxamido)-6-azaindol-3-yl)-oxoacetyl]-piperazine.

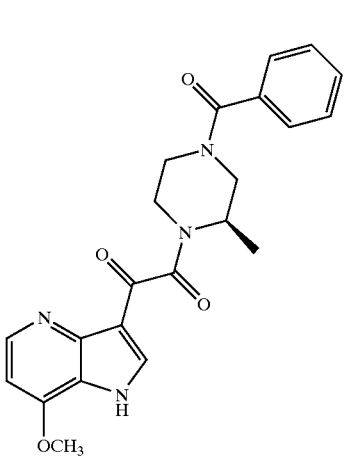

5abc

5abc(R)-N-(benzoyl)-3-methyl-N'-[(7-methoxy-4-azaindol-3-yl)-oxoacetyl]-piperazine

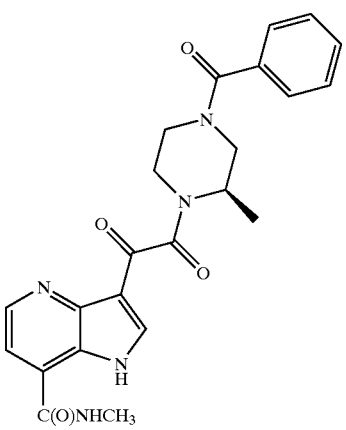

5abd

5abd (R)-N-(benzoyl)-3-methyl-N'-[(7-(N-methyl-carboxamido)-4-azaindol-3-yl)-oxoacetyl]-piperazine.

Compounds 5an, 5ao and 5ap are described below.

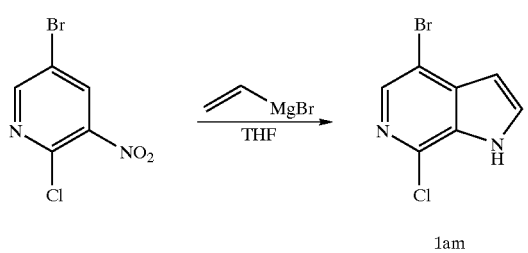

1am

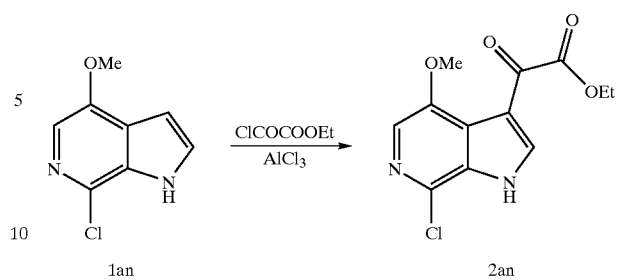

1an 2an

Compound 1am, 4-bromo-7-chloro-6-azaindole (yellow solid) was prepared by the same method used for azaindole 1e but the starting material employed was 5-bromo-2-chloro-3-nitropyridine. (available from Aldrich, Co.). MS m/z: (M+H)$^+$ calcd for $C_7H_5BrClN_2$: 230.93; found 231.15. HPLC retention time: 1.62 minutes (column B).

Compound 2an, Ethyl (7-chloro-4-methoxy-6-azaindol-3-yl)-oxoacetate was prepared by the same method used for compound 2b but the starting material employed was 4-methoxy-7-chloro-6-azaindole. The compound was purified by silica gel chromotography using 2:3 EtOAc: hexane as the eluent to give a yellow oil. MS m/z: (M+H)$^+$ calcd for $C_{12}H_{12}ClN_2O_4$: 283.05; found 283.22. HPLC retention time: 1.37 minutes (column B).

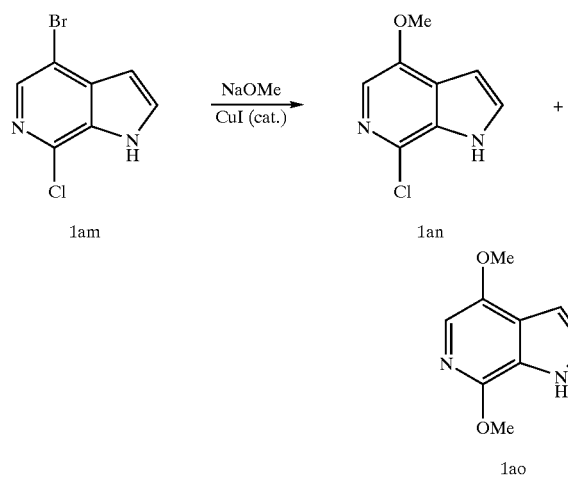

1am 1an

1ao

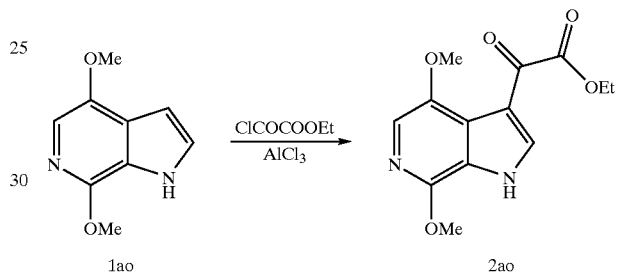

1ao 2ao

Compound 1an, 4-methoxy-7-chloro-6-azaindole and compound 1ao, 4,7-dimethoxy-6-azaindole: A mixture of 4-bromo-7-chloro-6-azaindole (1 g), CuI (0.65 g) and NaOMe (4 ml, 25%) in MeOH (16 ml) was heated at 110–120° C. for 16 hours in a sealed tube. After cooling to ambient temperature, the reaction mixture was neutralized with 1N HCl to achieve pH7. The aqueous solution was extracted with EtOAc (3×30 ml). Then the combined organic layer was dried over MgSO$_4$ and concentrated in vacuo to afford a residue, which was purified by silica gel (50 g) chromatography using 1:7 EtOAc: hexane as the eluent. (Column dimension: 20 mm×30 cm) to give 0.3 g of 4-methoxy-7-chloro-6-azaindole (white solid) and 0.1 g of 4,7-dimethoxy-6-azaindole (white solid).

Compound 1an, 4-methoxy-7-chloro-6-azaindole. MS m/z: (M+H)$^+$ calcd for $C_8H_8ClN_2O$: 183.03; found 183.09. HPLC retention time: 1.02 minutes (column B).

Compound 1ao, 4,7-dimethoxy-6-azaindole. $^1$H NMR (500 MHz, CDCl$_3$) δ 7.28 (m, 2H), 6.63 (m, 1H), 4.14 (s, 3H), 3.95 (s, 3H). MS m/z: (M+H)$^+$ calcd for $C_9H_{11}N_2O_2$: 179.08; found 179.05. HPLC retention time: 1.36 minutes (column B).

Compound 2ao, Ethyl (4,7-dimethoxy-6-azaindol-3-yl)-oxoacetate was prepared by the same method as used for compound 2b but the starting material employed was 4,7-dimethoxy-6-azaindole. The compound was purified by silica gel chromatography using 2:3 EtOAc: Hexane as the eluent to give a yellow oil: $^1$H NMR (500 MHz, CDCl$_3$) δ 9.50 (s, 1H), 8.21 (s, 1H), 7.47 (s, 1H), 4.39 (q, 2H, d=7.05 Hz), 4.13 (s, 3H), 3.93 (s, 3H), 1.40 (t, 3H, d=7.2 Hz). MS m/z: (M+H)$^+$ calcd for $C_{13}H_{15}N_2O_5$: 279.10; found 279.16. HPLC retention time: 1.28 minutes (column B).

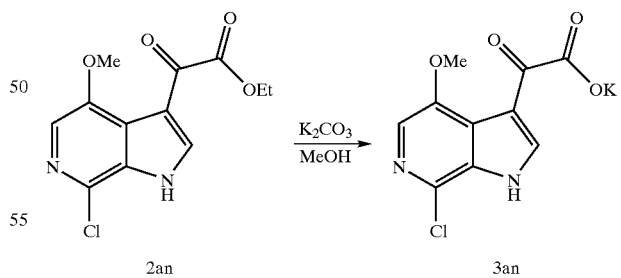

2an 3an

Compound 3an (which was a yellow solid), Potassium (7-chloro-4-methoxy-6-azaindol-3-yl)-oxoacetate was prepared by the same method used to prepare compound 3a except Ethyl (7-chloro-4-methoxy-6-azaindole-3-yl)-oxoacetate was used as the starting material. MS m/z: (M+H)$^+$ of the corresponding acid of compound 3an (M−K+H)$^+$ calcd for $C_{10}H_8ClN_2O_4$: 255.02; found 255.07. HPLC retention time: 0.74 minutes (column A).

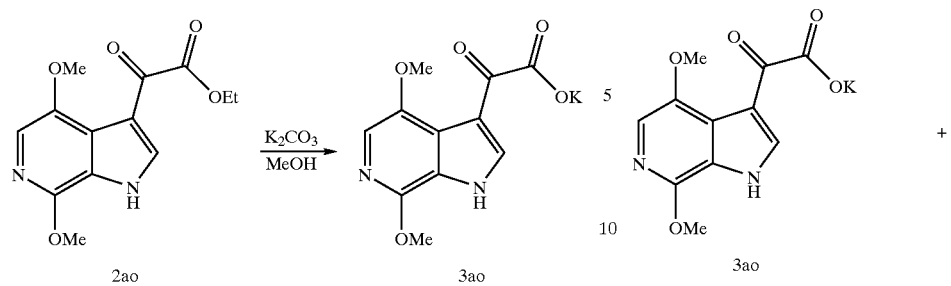

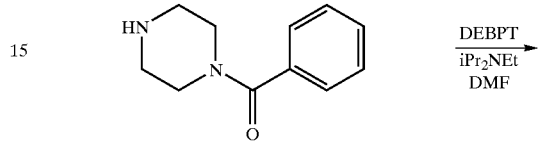

Compound 3ao (which was a yellow solid), Potassium (4,7-dimehoxy-6-azaindol-3-yl)-oxoacetate was prepared by the same method used to prepare compound 3a except Ethyl (4,7-dimethoxy-6-azaindol-3-yl)-oxoacetate was employed as the starting material. MS m/z: (M+H)+ of the corresponding acid of compound 3ao (M−K+H)+ calcd for $C_{11}H_{11}N_2O_5$: 251.07; found 251.09. HPLC retention time: 0.69 minutes (column B).

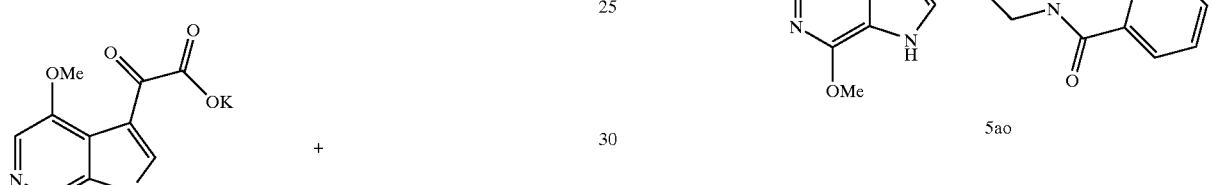

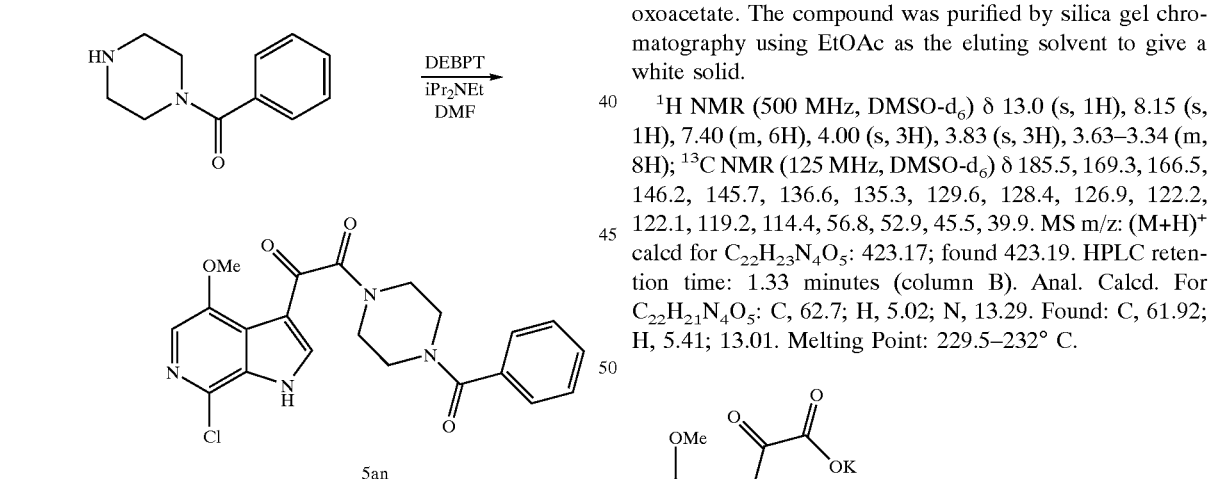

Compound 5an, N-(benzoyl)-N'-[(7-chloro-4-methoxy-6-azaindol-3-yl)-oxoacetyl]-piperazine was prepared by the same method which was used to prepare compound 5a except that Potassium (7-chloro-4-methoxy-6-azaindol-3-yl)-oxoacetate was employed as the starting material to give a white solid. The compound was purified by silica gel chromatography using EtOAc as the eluting solvent. MS m/z: (M+H)+ calcd for $C_{21}H_{20}ClN_4O_4$: 427.12; found 427.12. HPLC retention time: 1.28 minutes (column A).

Compound 5ao, N-(benzoyl)-N'-[(4,7-dimethoxy-6-azaindol-3-yl)-oxoacetyl]-piperazine was prepared by the same method used to prepare compound 5a but the starting material was Potassium (4,7-dimethoxy-6-azaindole-3-yl)-oxoacetate. The compound was purified by silica gel chromatography using EtOAc as the eluting solvent to give a white solid.

$^1$H NMR (500 MHz, DMSO-d$_6$) δ 13.0 (s, 1H), 8.15 (s, 1H), 7.40 (m, 6H), 4.00 (s, 3H), 3.83 (s, 3H), 3.63–3.34 (m, 8H); $^{13}$C NMR (125 MHz, DMSO-d$_6$) δ 185.5, 169.3, 166.5, 146.2, 145.7, 136.6, 135.3, 129.6, 128.4, 126.9, 122.2, 122.1, 119.2, 114.4, 56.8, 52.9, 45.5, 39.9. MS m/z: (M+H)+ calcd for $C_{22}H_{23}N_4O_5$: 423.17; found 423.19. HPLC retention time: 1.33 minutes (column B). Anal. Calcd. For $C_{22}H_{21}N_4O_5$: C, 62.7; H, 5.02; N, 13.29. Found: C, 61.92; H, 5.41; 13.01. Melting Point: 229.5–232° C.

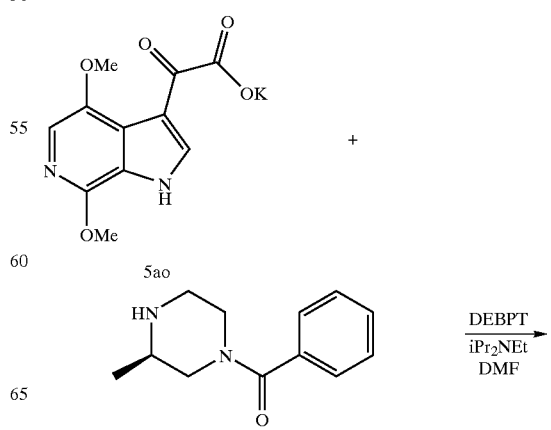

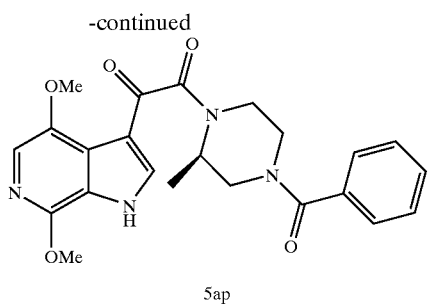

5ap

Compound 5ap, ®-N-(benzoyl)-3-methyl-N'-[(4,7-dimethoxy-6-azaindol-3-yl)-oxoacetyl]-piperazine (white solid) was prepared using the same method used to prepare compound 5a except that Potassium (4,7-dimethoxy-6-azaindol-3-yl)-oxoacetate was used as the starting material. MS m/z: (M+H)$^+$ calcd for $C_{23}H_{25}N_4O_5$: 437.18; found 437.24. HPLC retention time: 1.37 minutes (column B).

The compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating viral infections such as HIV infection and AIDS. The treatment involves administering to a patient in need of such treatment a pharmaceutical composition comprising a pharmaceutical carrier and a therapeutically-effective amount of a compound of the present invention.

The pharmaceutical composition may be in the form of orally-administrable suspensions or tablets; nasal sprays, sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds of this invention can be administered orally to humans in a dosage range of 1 to 100 mg/kg body weight in divided doses. One preferred dosage range is 1 to 10 mg/kg body weight orally in divided doses. Another preferred dosage range is 1 to 20 mg/kg body weight orally in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

| Abbreviations or Alternative Names | |
|---|---|
| TFA | Trifluoroacetic Acid |
| DMF | N,N-Dimethylformamide |
| THF | Tetrahydrofuran |
| MeOH | Methanol |
| Ether | Diethyl Ether |
| DMSO | Dimethyl Sulfoxide |
| EtOAc | Ethyl Acetate |
| Ac | Acetyl |
| Bz | Benzoyl |
| Me | Methyl |
| Et | Ethyl |
| Pr | Propyl |
| Py | Pyridine |
| Hunig's Base | N,N-Diisopropylethylamine |
| DEPBT | 3-(Diethoxyphosphoryloxy)-1,2,3-benzotriazin-4(3H)-one |
| DEPC | diethyl cyanophosphate |
| DMP | 2,2-dimethoxypropane |
| mCPBA | meta-Chloroperbenzoic Acid |
| azaindole | 1H-Pyrrolo-pyridine |
| 4-azaindole | 1H-pyrrolo[3,2-b]pyridine |
| 5-azaindole | 1H-Pyrrolo[3,2-c]pyridine |
| 6-azaindole | 1H-pyrrolo[2,3-c]pyridine |
| 7-azaindole | 1H-Pyrrolo[2,3-b]pyridine |

What is claimed is:
1. A compound having the formula 1

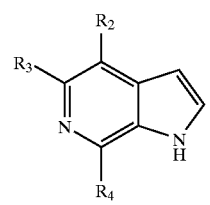

(1)

wherein:
R$_3$ is H; and
R$_2$ is fluoro, chloro, bromo or methoxy; and R$_4$ is chloro, methoxy or —C(O)NHCH$_3$.
2. The compound of claim 1 wherein:
R$_2$ and R$_4$ are each methoxy.

\* \* \* \* \*